US009475761B2

(12) United States Patent
Katagiri et al.

(10) Patent No.: US 9,475,761 B2
(45) Date of Patent: Oct. 25, 2016

(54) METHOD FOR PRODUCING CYANOGEN-HALIDE, CYANATE ESTER COMPOUND AND METHOD FOR PRODUCING THE SAME, AND RESIN COMPOSITION

(71) Applicant: MITSUBISHI GAS CHEMICAL COMPANY, INC., Tokyo (JP)

(72) Inventors: Masayuki Katagiri, Niigata (JP); Yuuichi Sugano, Niigata (JP); Taketo Ikeno, Niigata (JP); Makoto Tsubuku, Niigata (JP); Keita Tokuzumi, Niigata (JP); Kenj Arii, Tokyo (JP); Takashi Kobayashi, Tokyo (JP); Masanobu Sogame, Tokyo (JP); Yoshinori Mabuchi, Tokyo (JP); Yoshihiro Kato, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/436,295

(22) PCT Filed: Oct. 25, 2013

(86) PCT No.: PCT/JP2013/079048

§ 371 (c)(1),
(2) Date: Apr. 16, 2015

(87) PCT Pub. No.: WO2014/065422

PCT Pub. Date: May 1, 2014

(65) Prior Publication Data

US 2015/0299110 A1 Oct. 22, 2015

(30) Foreign Application Priority Data

Oct. 26, 2012 (JP) ................................. 2012-236302
Jan. 8, 2013 (JP) ................................. 2013-001002
Mar. 4, 2013 (JP) ................................. 2013-041491
Mar. 22, 2013 (JP) ................................. 2013-059992

(51) Int. Cl.
*C01C 3/08* (2006.01)
*C07C 261/00* (2006.01)
(Continued)

(52) U.S. Cl.
CPC .............. *C07C 261/02* (2013.01); *B32B 15/09* (2013.01); *B32B 27/36* (2013.01); *C01C 3/004* (2013.01);
(Continued)

(58) Field of Classification Search
CPC ... C07C 261/02; C09J 161/14; C09J 171/00; H05K 1/0346; C08L 2203/20; C08L 71/00; C08L 61/14; C08J 2371/10; C08J 2361/14; C08J 5/24; C08J 5/04; C08G 2190/00; C08G 65/48; C08G 8/28; B32B 2457/08; B32B 2260/046; B32B 27/36; B32B 15/09; C09K 3/10; C01C 3/004
USPC ...... 428/195.1, 458; 423/371, 379; 523/400; 524/104, 594, 611, 87; 525/504, 523, 525/534; 560/301
See application file for complete search history.

(56) References Cited

U.S. PATENT DOCUMENTS 3,755,542 A * 8/1973 Suryanarayana ....... C01C 3/004
423/364
4,748,270 A 5/1988 Murray et al.
(Continued)

FOREIGN PATENT DOCUMENTS

CN 1140706 1/1997
CN 1181763 5/1998
(Continued)

OTHER PUBLICATIONS

Search report from PCT/JP2013/079048, mail date is Jan. 21, 2014.
(Continued)

*Primary Examiner* — David Karst
(74) *Attorney, Agent, or Firm* — Greenblum & Bernstein, P.L.C.

(57) ABSTRACT

A method for efficiently producing a cyanogen halide with suppressed side effects, and a method for producing a high-purity cyanate ester compound at a high yield includes contacting a halogen molecule with an aqueous solution containing hydrogen cyanide and/or a metal cyanide, so that the hydrogen cyanide and/or the metal cyanide is allowed to react with the halogen molecule in the reaction solution to obtain the cyanogen halide, wherein more than 1 mole of the hydrogen cyanide or the metal cyanide is used based on 1 mole of the halogen molecule, and when an amount of substance of an unreacted hydrogen cyanide or an unreacted metal cyanide is defined as mole (A) and an amount of substance of the generated cyanogen halide is defined as mole (B), the reaction is terminated in a state in which (A):(A)+(B) is between 0.00009:1 and 0.2:1.

19 Claims, 7 Drawing Sheets

(51) Int. Cl.

| | |
|---|---|
| *C07C 261/02* | (2006.01) |
| *C01C 3/00* | (2006.01) |
| *B32B 15/09* | (2006.01) |
| *B32B 27/36* | (2006.01) |
| *C08G 8/28* | (2006.01) |
| *C08G 65/48* | (2006.01) |
| *C08J 5/04* | (2006.01) |
| *C08J 5/24* | (2006.01) |
| *C08L 61/14* | (2006.01) |
| *C08L 71/00* | (2006.01) |
| *C09J 161/14* | (2006.01) |
| *C09J 171/00* | (2006.01) |
| *C09K 3/10* | (2006.01) |
| *H05K 1/03* | (2006.01) |

(52) U.S. Cl.
CPC ............... *C08G 8/28* (2013.01); *C08G 65/48* (2013.01); *C08J 5/04* (2013.01); *C08J 5/24* (2013.01); *C08L 61/14* (2013.01); *C08L 71/00* (2013.01); *C09J 161/14* (2013.01); *C09J 171/00* (2013.01); *C09K 3/10* (2013.01); *H05K 1/0346* (2013.01); *B32B 2260/046* (2013.01); *B32B 2457/08* (2013.01); *C08G 2190/00* (2013.01); *C08J 2361/14* (2013.01); *C08J 2371/10* (2013.01); *C08L 2203/20* (2013.01)

(56) References Cited

U.S. PATENT DOCUMENTS

| | | | |
|---|---|---|---|
| 4,751,323 | A | 6/1988 | Woo et al. |
| 4,931,545 | A | 6/1990 | Shimp et al. |
| 5,648,435 | A | 7/1997 | Roth, Jr. et al. |
| 2009/0130488 | A1 | 5/2009 | Sugano et al. |
| 2013/0281640 | A1 | 10/2013 | Tsubuku et al. |
| 2014/0073721 | A1 | 3/2014 | Yaginuma et al. |

FOREIGN PATENT DOCUMENTS

| | | |
|---|---|---|
| CN | 1467238 | 1/2004 |
| CN | 1477136 | 2/2004 |
| CN | 1569822 | 1/2005 |
| CN | 1663946 | 9/2005 |
| CN | 101450808 | 6/2009 |
| CN | 102558471 | 7/2012 |
| CN | 102558472 | 7/2012 |
| EP | 0739879 | 10/1996 |
| JP | 57-27924 | 2/1982 |
| JP | 61-500120 | 1/1986 |
| JP | 62-51891 | 11/1987 |
| JP | 63-373 | 1/1988 |
| JP | 2-34342 | 8/1990 |
| JP | 6-11741 | 2/1994 |
| JP | 6-55814 | 7/1994 |
| JP | 6-271669 | 9/1994 |
| JP | 11-124433 | 5/1999 |
| JP | 3081996 | 6/2000 |
| JP | 200-191776 | 7/2000 |
| JP | 2006-249177 | 9/2006 |
| JP | 4407823 | 11/2009 |
| JP | 2010-180147 | 8/2010 |
| JP | 4654770 | 1/2011 |
| JP | 2011-132167 | 7/2011 |
| JP | 2012-36114 | 2/2012 |
| JP | 5104312 | 10/2012 |
| WO | 2012/057144 | 5/2012 |
| WO | 2012/128313 | 9/2012 |

OTHER PUBLICATIONS

International Preliminary Report on Patentability issued Apr. 28, 2015 in PCT/JP2013/079048 with English Translation.

Chinese Office Action issued in Patent Application No. 201380055999.3, dated May 10, 2016.

Zhu; "Inorganic compound preparation manual"; Chemical Industry Press; Sep. 1, 2006; pp. 799.

\* cited by examiner

METHOD FOR PRODUCING CYANOGEN-HALIDE, CYANATE ESTER COMPOUND AND METHOD FOR PRODUCING THE SAME, AND RESIN COMPOSITION

TECHNICAL FIELD

The present invention relates to a method for producing a cyanogen halide, a cyanate ester compound and a method for producing the same, and a resin composition.

BACKGROUND ART

Conventionally, as methods for producing a cyanate ester compound, a method of allowing a cyanogen halide to react with phenol in the presence of a tertiary amine, a method of allowing a cyanogen halide to react with an alcoholic or phenolic alkaline metal salt, and the like have been known. In addition, it has been known that a cyanogen halide obtained by reacting hydrogen cyanide and/or a metal cyanide with halogen is used to produce a cyanate ester compound.

It has been proposed that, when hydrogen cyanide is reacted with chlorine in a water solvent or when sodium cyanide is reacted with chlorine in an aqueous solution of hydrochloric acid, so as to produce a cyanogen chloride, it is desired to terminate the reaction, such that unreacted hydrogen cyanide (unreacted sodium cyanide) or unreacted chlorine is not allowed to remain in the cyanogen chloride-containing solution, from the viewpoint of the safety of the cyanogen chloride (see, for example, Patent Literatures 1 and 2). However, it is extremely difficult to control the reaction such that neither unreacted hydrogen cyanide (unreacted sodium cyanide) nor unreacted chlorine remains in the reaction system, in order to terminate the reaction.

Moreover, when an aqueous solution of metal cyanide is allowed to react with chlorine in a halogenated hydrocarbon to produce a cyanogen chloride, it has been proposed to use the metal cyanide in an equimolar ratio of the chlorine, or less. For instance, it has been proposed that the molar ratio between a metal cyanide and chlorine is set from 1:1.15 to 1:1 (see, for example, Patent Literatures 3, 4, and 5).

Furthermore, when hydrogen cyanide or a metal cyanide is allowed to react with halogen to produce a cyanogen halide, even if the amounts of the hydrogen cyanide or the metal cyanide and the halogen used (the composition of the added materials) have been determined, the composition of a cyanogen halide-containing solution upon termination of the reaction (the generated cyanogen halide, unreacted halogen, unreacted hydrogen cyanide, unreacted metal cyanide) has not been determined (see, for example, Patent Literatures 1, 2, 3, and 4).

The thus produced cyanate ester compound generates a triazine ring as a result of hardening, and because of high heat resistance and excellent electrical properties, the cyanate ester compound has been widely used as a raw material for various functional polymer materials such as printed circuit boards, sealing materials for electronic components, molding materials, structural composite materials, adhesives, electrical insulating materials, and electrical and electronic components. However, in recent years, with the advancement of performance required in these application fields, various physical properties required for the cyanate ester compound as a functional polymer material have been increased. Examples of such physical properties required include flame retardance, heat resistance, a low coefficiency of thermal expansion, low water-absorbing property, low dielectric constant, low dielectric loss tangent, weather resistance, chemical resistance, and high fracture toughness. Nevertheless, to date, these required performances have not been necessarily satisfied.

For instance, in the field of semiconductor packaging materials, there is a problem that warpage occurs between a semiconductor chip and a substrate material due to a mismatch in coefficiencys of thermal expansion, with the thinning of the substrate. As a means for solving this problem, it has been desired to reduce the coefficiency of thermal expansion of a functional polymer material used as a substrate material and to improve high heat resistance. In addition, from the viewpoint of consideration on human bodies and environment, the use of lead-free solder has been promoted for the soldering of a printed wiring board. Also, from the viewpoint of resistance to a reflow step at a high temperature attended with the lead-free soldering, it has been desired to reduce the coefficiency of thermal expansion of a functional polymer material and to improve high heat resistance.

Moreover, it has also been desired to exclude halogen atoms that are likely to generate halogen gas having a risk of causing environmental contamination during combustion and are also likely to reduce the insulating property of a final product, or phosphorus atoms that are likely to reduce required physical properties other than flame retardance (i.e., heat resistance, moisture resistance, low water-absorbing property, etc.), and to improve the flame retardance of a functional polymer material.

As a simple cyanate ester compound, which is used to produce a hardened product having low thermal expansion and heat resistance, a difunctional cyanatophenyl-based cyanate ester compound (1,1-bis(4-cyanatophenyl)isobutane), in which the hydrogen in a methylene group binding cyanatophenyl groups is replaced by a specific alkyl group, has been proposed (see, for example, Patent Literature 6).

Furthermore, as simple cyanate ester compounds, which are used to produce hardened products having heat resistance and flame retardance, a cyanate ester compound having an aralkyl structure (see, for example, Patent Literature 7), a cyanate ester compound containing an isocyanuric acid skeleton (see Patent Literature 8), a cyanate ester compound containing a triazine skeleton (see, for example, Patent Literature 9), and a difunctional cyanatophenyl-based cyanate ester compound, in which the hydrogen in a methylene group binding cyanatophenyl groups is replaced by a biphenyl group (see, for example, Patent Literature 10), have been proposed. Further, as a mixture of cyanate ester compounds, which is used to produce a hardened product having heat resistance and flame retardance, a combination of a bisphenol A-based cyanate ester compound with a cyanate ester compound containing an imide skeleton (see, for example, Patent Literature 11) has been proposed.

On the other hand, such a cyanate ester compound has been conventionally used as a resin for printed wiring boards with excellent heat resistance. In recent years, high integration and/or miniaturization of semiconductors that are widely used for electronic devices, communication devices, personal computers and the like have been increasingly accelerated. With such high integration and/or miniaturization, laminates for semiconductor packaging, which are used for printed wiring boards, are required to have physical properties at high levels, such as heat resistance, low water-absorbing property, heat resistance upon moisture absorption, and flame retardance.

Examples of a cyanate ester compound widely used as a raw material for printed wiring boards and the like include a bisphenol A-based cyanate ester compound and a resin composition comprising another thermosetting resin or the like. The bisphenol A-based cyanate ester compound has excellent properties such as electrical properties, mechanical properties, and chemical resistance. However, in some cases, this compound is insufficient in terms of low water-absorbing property, heat resistance upon moisture absorption, and flame retardance. Hence, for the purpose of further improving such properties, studies regarding various cyanate ester compounds having different structures have been conducted.

As a resin having a structure that is different from that of the bisphenol A-based cyanate ester compound, a novolac-based cyanate ester compound has been frequently used (see Patent Literature 12). Moreover, prepolymerization of a novolac-based cyanate ester compound and a bisphenol A-based cyanate ester compound has been proposed (see Patent Literature 13).

Furthermore, as a method of improving flame retardance, it has been proposed to use a fluorinated cyanate ester compound, or to mix a cyanate ester compound with a halogen compound or prepolymerize these compounds, so as to allow a resin composition to comprise the halogen compound (see Patent Literatures 14 and 15).

CITATION LIST

Patent Literature

Patent Literature 1: Japanese Patent Publication No. S62-51891
Patent Literature 2: Japanese Patent Publication No. S63-373
Patent Literature 3: Japanese Patent Publication No. H02-34342
Patent Literature 4: Japanese Patent Publication No. H06-11741
Patent Literature 5: Japanese Patent Publication No. H06-55814
Patent Literature 6: International Publication No. WO 2012/057144
Patent Literature 7: Japanese Patent No. 4407823
Patent Literature 8: Japanese Patent No. 4654770
Patent Literature 9: Japanese Patent Laid-Open No. 2012-036114
Patent Literature 10: Japanese Patent No. 5104312
Patent Literature 11: Japanese Patent Laid-Open No. 2010-180147
Patent Literature 12: Japanese Patent Laid-Open No. H11-124433
Patent Literature 13: Japanese Patent Laid-Open No. 2000-191776
Patent Literature 14: Japanese Patent No. 3081996
Patent Literature 15: Japanese Patent Laid-Open No. H06-271669

SUMMARY OF INVENTION

Technical Problem

However, when hydrogen cyanide or a metal cyanide is used in an amount of less than 1 mole based on 1 mole of halogen, namely, when halogen is excessively used with respect to hydrogen cyanide or a metal cyanide, unreacted halogen remains in the reaction system. Thus, there is a problem that, if the obtained cyanogen halide-containing solution is directly used to produce a cyanate ester compound, reaction by-products would be generated from such unreacted halogen, which is hardly removed from the cyanate ester compound even by a washing operation.

On the other hand, when hydrogen cyanide or a metal cyanide is used in an amount excessively larger than 1 mole based on 1 mole of halogen, namely, when hydrogen cyanide or a metal cyanide is excessively used with respect to halogen, a large amount of unreacted hydrogen cyanide or unreacted metal cyanide remains in the reaction system. Thus, there is a problem that, if the obtained cyanogen halide-containing solution is directly used to produce a cyanate ester compound, a cyanogen halide is lost by a reaction of such unreacted hydrogen cyanide or unreacted metal cyanide with the generated cyanogen halide (subgeneration of dicyan), and thus that the efficiency of a reaction of producing a cyanate ester would be significantly reduced (i.e., a significant increase in the amount of a basic compound used).

An aspect of the present invention has been made considering the aforementioned problems, and it is an object of the present invention to provide a method for efficiently producing a cyanogen halide capable of suppressing side reactions in the production of a cyanate ester compound, and a method for producing a high-purity cyanate ester compound at a high yield (hereinafter referred to as a "first object").

On the other hand, there is a problem that, in a difunctional cyanatophenyl-based cyanate ester compound, when the hydrogen in a methylene group binding cyanatophenyl groups is replaced by an alkyl group, the flame retardance of the compound (low degradability at a high temperature) would be reduced. In addition, Patent Literature 6 contains no descriptions regarding flame retardance. Moreover, in all cases of Patent Literatures 7 to 11, a hardened product consisting only of a practicable simple cyanate ester compound comprising all of low thermal expansion, heat resistance and flame retardance at high levels has not yet been obtained.

Another aspect of the present invention has been made considering the aforementioned problem, and it is another object of the present invention to provide a resin composition and the like, which can be used to produce a hardened product having a low coefficient of thermal expansion and also having high flame retardance, low water-absorbing property, heat resistance upon moisture absorption, and heat resistance (hereinafter referred to as a "second object").

Moreover, a novolac-based cyanate ester compound is problematic in that it easily causes insufficient hardness, and in that the obtained hardened product has a high water absorption rate and decreased heat resistance upon moisture absorption. Furthermore, even in a case in which such a novolac-based cyanate ester compound is prepolymerized in order to solve the aforementioned problem, the improvement of the properties of the resulting novolac-based cyanate ester compound, such as water-absorbing property and heat resistance upon moisture absorption, have been still insufficient, although hardness has been improved. Accordingly, it has been desired to further improve low water-absorbing property and heat resistance upon moisture absorption.

Furthermore, when a halogen compound is used, there is a risk that a harmful substance such as dioxin may be generated during combustion. Accordingly, it has been desired to improve flame retardance without comprising such a halogen compound.

A further aspect of the present invention has been made considering the aforementioned problem, and it is a further object of the present invention to provide a hardened product, a prepreg, a laminate, a sealing material, a fiber-reinforced composite material, an adhesive, a resin composite sheet, and a printed wiring board, which have a low coefficient of thermal expansion and also have high flame retardance, low water-absorbing property, heat resistance upon moisture absorption, and heat resistance (hereinafter referred to as a "third object").

Solution to Problem

The present inventors have conducted intensive studies directed towards achieving the aforementioned first object. As a result, the inventors have found that the aforementioned first object can be achieved by determining the amount of hydrogen cyanide or a metal cyanide used in a reaction of the hydrogen cyanide and/or the metal cyanide with a halogen molecule in a predetermined range in a method for producing a cyanogen halide, and by determining the terminal point of the reaction, thereby completing the present invention.

Moreover, the present inventors have conducted intensive studies directed towards achieving the aforementioned second object. As a result, the inventors have found that the aforementioned second object can be achieved by using a predetermined cyanate ester compound, which has been produced using a cyanogen halide obtained by the above described method for producing a cyanogen halide and a hydroxy-substituted aromatic compound, thereby completing the present invention.

Furthermore, the present inventors have conducted intensive studies directed towards achieving the aforementioned third object. As a result, the inventors have found that the aforementioned third object can be achieved by using the above described resin composition, thereby completing the present invention.

Specifically, the present invention is as follows.

[1]
A method for producing a cyanogen halide, which comprises a cyanogen halide-producing step of contacting a halogen molecule with an aqueous solution containing hydrogen cyanide and/or a metal cyanide, so that the hydrogen cyanide and/or the metal cyanide is allowed to react with the halogen molecule in a reaction solution to obtain the cyanogen halide, wherein in the cyanogen halide-producing step, more than 1 mole of the hydrogen cyanide or the metal cyanide is used based on 1 mole of the halogen molecule, and when an amount of substance of an unreacted hydrogen cyanide or an unreacted metal cyanide is defined as mole (A) and an amount of substance of the generated cyanogen halide is defined as mole (B), the reaction is terminated in a state in which (A):(A)+(B) is between 0.00009:1 and 0.2:1.

[2]
The method for producing the cyanogen halide according to [1] described above, wherein, in the cyanogen halide-producing step, a pH of the reaction solution is less than 7.

[3]
The method for producing the cyanogen halide according to [1] or [2] described above, wherein the hydrogen cyanide has previously been obtained by a reaction of a metal cyanide with an acid.

[4]
The method for producing the cyanogen halide according to any one of [1] to [3] described above, wherein, in the cyanogen halide-producing step, a reaction temperature is $-10°$ C. to $5°$ C.

[5]
The method for producing the cyanogen halide according to any one of [1] to [4] described above, wherein a total content of the hydrogen cyanide and/or the metal cyanide in the aqueous solution is 2% to 20% by mass based on 100% by mass of the aqueous solution.

[6]
The method for producing the cyanogen halide according to any one of [1] to [5] described above, further comprising an extraction step of extracting the obtained cyanogen halide with an organic solvent after the cyanogen halide-producing step.

[7]
A method for producing a cyanate ester compound, which comprises a cyanation step of allowing the cyanogen halide obtained by the method for producing the cyanogen halide according to any one of [1] to [6] described above to react with a hydroxy-substituted aromatic compound in the presence of a basic compound in the reaction solution, to obtain a cyanate ester compound.

[8]
The method for producing the cyanate ester compound according to [7] described above, wherein, in the cyanation step, a solution containing the cyanogen halide and the hydroxy-substituted aromatic compound is contacted with a solution containing the basic compound.

[9]
The method for producing the cyanate ester compound according to [7] described above, wherein, in the cyanation step, a solution containing the cyanogen halide is contacted with a solution containing the basic compound and the hydroxy-substituted aromatic compound.

[10]
The method for producing the cyanate ester compound according to [8] or [9] described above, wherein the solution containing the cyanogen halide comprises an organic solvent.

[11]
The method for producing the cyanate ester compound according to [8] or [9] described above, wherein the solution containing the cyanogen halide comprises a mixture of water and an organic solvent.

[12]
The method for producing the cyanate ester compound according to any one of [8] to [11] described above, wherein the solution containing the basic compound comprises an organic solvent.

[13]
The method for producing the cyanate ester compound according to any one of [8] to [11] described above, wherein the solution containing the basic compound comprises water.

[14]
The method for producing the cyanate ester compound according to any one of [7] to [13] described above, wherein, in the cyanation step, a pH of the reaction solution is less than 7.

[15]
The method for producing the cyanate ester compound according to any one of [7] to [14] described above, wherein, in the cyanation step, 0.5 to 5 moles of the cyanogen halide are used based on 1 mole of the hydroxy group of the hydroxy-substituted aromatic compound.

[16]

The method for producing the cyanate ester compound according to any one of [7] to [15] described above, wherein the hydroxy-substituted aromatic compound is at least one selected from the group consisting of a phenolic resin having a polynaphthylene ether structure, a compound represented by the following general formula (1), a naphthol aralkyl resin, and a phenolic resin having an adamantane structure:

[Formula 1]

$$H-\underset{(Ra)_m}{\underset{|}{Ar^1}}-(OH)_l \underset{}{+X-}\underset{(Ra)_m}{\underset{|}{Ar^1}}+_n H \quad (1)$$

wherein $Ar^1$ each independently represent a phenylene group optionally having a substituent, a naphthylene group optionally having a substituent, or a biphenylene group optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; m represents the number of Ra bonded to $Ar^1$, wherein it is an integer of 4-1 when $Ar^1$ represents a phenylene group, it is an integer of 6-1 when $Ar^1$ represents a naphthylene group, and it is an integer of 8-1 when $Ar^1$ represents a biphenylene group; n represents an average number of repetitions, which is an integer of 0 to 50; and X each independently represent a single bond, a divalent organic group containing 1 to 50 carbon atoms (wherein a hydrogen atom may be optionally replaced by a heteroatom), a divalent organic group containing 1 to 10 nitrogen atoms, a carbonyl group (—CO—), a carboxy group (—C(=O)O—), a carbonyl dioxide group (—OC(=O)O—), a sulfonyl group (—SO$_2$—), or a divalent sulfur atom or a divalent oxygen atom.

[17]

The method for producing the cyanate ester compound according to [16] described above, wherein X in the above general formula (1) is a divalent linking group selected from the group consisting of a divalent organic group represented by the following general formula (2):

[Formula 2]

$$-\underset{Rc}{\underset{|}{\overset{Rb}{\overset{|}{C}}}}+\underset{Re}{\underset{|}{\overset{Rd}{\overset{|}{Ar^2}}}}-\underset{Rg}{\underset{|}{\overset{Rf}{\overset{|}{C}}}}+_p- \quad (2)$$

wherein $Ar^2$ each independently represent a phenylene group optionally having a substituent, a naphthylene group optionally having a substituent, or a biphenylene group optionally having a substituent; Rb, Rc, Rf, and Rg each independently represent a hydrogen atom, an alkyl group containing 1 to 6 carbon atoms and optionally having a substituent, or an aryl group containing 6 to 12 carbon atoms and optionally having a substituent; Rd and Re each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group; and p represents an integer of 0 to 5, and divalent groups represented by the following general formulae (2a), (2b), (2c), (2d), (2e), (2f), (2g), (2h), (2i), and (2j):

[Formula 3]

—O— (2a)

$$-\overset{O}{\overset{\|}{C}}-O- \quad (2b)$$

—S— (2c)

(2d)

(2e)

$$-\overset{O}{\overset{\|}{C}}- \quad (2f)$$

$$-O-\overset{O}{\overset{\|}{C}}-O- \quad (2g)$$

$$-\overset{O}{\underset{O}{\overset{\|}{\underset{\|}{S}}}}- \quad (2h)$$

(2i)

(2j)

wherein, in the formula (2d), q represents an integer of 4 to 7, and in the formula (2i), R each independently represents a hydrogen atom or an alkyl group containing 1 to 6 carbon atoms and optionally having a substituent.

[18]

The method for producing the cyanate ester compound according to [16] or [17] described above, wherein the phenolic resin having a polynaphthylene ether structure is obtained by subjecting a polyhydric hydroxynaphthalene compound having two or more phenolic hydroxy groups in one molecule to a dehydration condensation reaction in the presence of a basic catalyst.

[19]

The method for producing the cyanate ester compound according to any one of [16] to [18] described above, wherein the phenolic resin having a polynaphthylene ether structure comprises a compound represented by the following general formula (3):

[Formula 4]

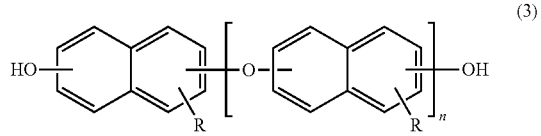

(3)

wherein R each independently represents a hydrogen atom, an aryl group and an alkyl group, or the following general formula (4); and n represents an integer of 1 to 20:

[Formula 5]

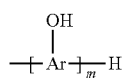

(4)

wherein Ar each independently represent an aryl group; and m represents an integer of 1 or 2.

[20]

The method for producing the cyanate ester compound according to any one of [16] to [19] described above, wherein the naphthol aralkyl resin comprises a resin represented by the following formula (19):

[Formula 6]

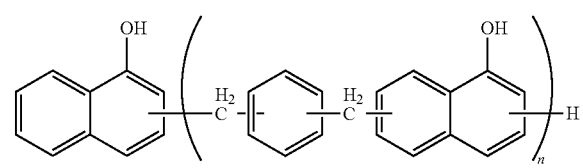

(19)

wherein n represents an integer of 1 to 50.

[21]

The method for producing the cyanate ester compound according to any one of [16] to [20] described above, wherein the phenolic resin having an adamantane structure comprises a resin represented by the following formula (20):

[Formula 7]

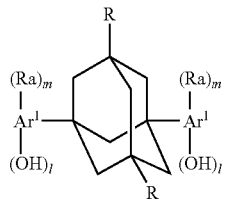

(20)

wherein $Ar^1$ each independently represent a phenylene group optionally having a substituent, a naphthylene group optionally having a substituent, or a biphenylene group optionally having a substituent; R each independently represent a hydrogen atom or an alkyl group containing 1 to 6 carbon atoms and optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; and m represents the number of Ra bonded to $Ar^1$, wherein it is an integer of 5-1 when $Ar^1$ represents a phenylene group, it is an integer of 7-1 when $Ar^1$ represents a naphthylene group, and it is an integer of 9-1 when $Ar^1$ represents a biphenylene group.

[22]

A cyanate ester compound, which is obtained by cyanation of a hydroxy-substituted aromatic compound using the cyanogen halide produced by the method for producing the cyanogen halide according to any one of [1] to [6] described above.

[23]

The cyanate ester compound according to [22] described above, wherein the hydroxy-substituted aromatic compound is at least one selected from the group consisting of a phenolic resin having a polynaphthylene ether structure, a compound represented by the following general formula (1), a naphthol aralkyl resin, and a phenolic resin having an adamantane structure:

[Formula 8]

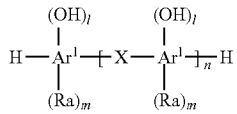

(1)

wherein $Ar^1$ each independently represent a phenylene group optionally having a substituent, a naphthylene group optionally having a substituent, or a biphenylene group optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; m represents the number of Ra bonded to $Ar^1$, wherein it is an integer of 4-1 when $Ar^1$ represents a phenylene group, it is an integer of 6-1 when $Ar^1$ represents a naphthylene group, and it is an integer of 8-1 when $Ar^1$ represents a biphenylene group; n represents an average number of repetitions, which is an integer of 0 to 50; and X each independently represent a single bond, a divalent organic group containing 1 to 50 carbon atoms (wherein a hydrogen atom may be optionally replaced by a heteroatom), a divalent organic group containing 1 to 10 nitrogen atoms, a carbonyl group (—CO—), a carboxy group (—C(=O)O—), a carbonyl dioxide group (—OC(=O)O—), a sulfonyl group (—SO$_2$—), or a divalent sulfur atom or a divalent oxygen atom.

[24]

The cyanate ester compound according to [23] described above, wherein X in the above general formula (1) is a divalent linking group selected from the group consisting of a divalent organic group represented by the following general formula (2):

[Formula 9]

$$\begin{array}{c} Rb \quad Rd \quad Rf \\ | \quad\; | \quad\; | \\ -C + Ar^2 - C +_p \\ | \quad\; | \quad\; | \\ Rc \quad Re \quad Rg \end{array} \quad (2)$$

wherein $Ar^2$ each independently represent a phenylene group optionally having a substituent, a naphthylene group optionally having a substituent, or a biphenylene group optionally having a substituent; Rb, Rc, Rf, and Rg each independently represent a hydrogen atom, an alkyl group containing 1 to 6 carbon atoms and optionally having a substituent, or an aryl group containing 6 to 12 carbon atoms and optionally having a substituent; Rd and Re each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group; and p represents an integer of 0 to 5, and divalent groups represented by the following general formulae (2a), (2b), (2c), (2d), (2e), (2f), (2g), (2h), (2i), and (2j):

[Formula 10]

—O— (2a)

$$-\overset{O}{\underset{}{\overset{\|}{C}}}-O-\quad (2b)$$

—S— (2c)

-continued (2d)

(2e)

$$-\overset{O}{\underset{}{\overset{\|}{C}}}-\quad (2f)$$

$$-O-\overset{O}{\underset{}{\overset{\|}{C}}}-O-\quad (2g)$$

$$-\overset{O}{\underset{O}{\overset{\|}{\underset{\|}{S}}}}-\quad (2h)$$

(2i)

(2j)

wherein, in the formula (2d), q represents an integer of 4 to 7, and in the formula (2i), R each independently represents a hydrogen atom or an alkyl group containing 1 to 6 carbon atoms and optionally having a substituent.

[25]

The cyanate ester compound according to [23] or [24] described above, wherein the phenolic resin having a polynaphthylene ether structure is obtained by subjecting a polyhydric hydroxynaphthalene compound having two or more phenolic hydroxy groups in one molecule to a dehydration condensation reaction in the presence of a basic catalyst.

[26]

The cyanate ester compound according to any one of [23] to [25] described above, wherein the phenolic resin having a polynaphthylene ether structure comprises a compound represented by the following general formula (3):

[Formula 11]

(3)

wherein R each independently represents a hydrogen atom, an aryl group and an alkyl group, or the following general formula (4); and n represents an integer of 1 to 20:

[Formula 12]

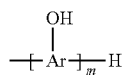

(4)

wherein Ar each independently represent an aryl group; and m represents an integer of 1 or 2.

[27]

The cyanate ester compound according to any one of [23] to [26] described above, wherein the naphthol aralkyl resin comprises a resin represented by the following formula (19):

[Formula 13]

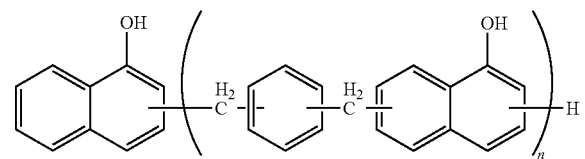

(19)

wherein n represents an integer of 1 to 50.

[28]

The cyanate ester compound according to any one of [23] to [27] described above, wherein the phenolic resin having an adamantane structure comprises a resin represented by the following formula (20):

[Formula 14]

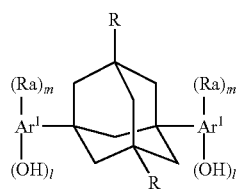

(20)

wherein $Ar^1$ each independently represent a phenylene group optionally having a substituent, a naphthylene group optionally having a substituent, or a biphenylene group optionally having a substituent; R each independently represent a hydrogen atom or an alkyl group containing 1 to 6 carbon atoms and optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; and m represents the number of Ra bonded to $Ar^1$, wherein it is an integer of 5-l when $Ar^1$ represents a phenylene group, it is an integer of 7-l when $Ar^1$ represents a naphthylene group, and it is an integer of 9-l when $Ar^1$ represents a biphenylene group.

[29]

A resin composition comprising the cyanate ester compound according to any one of [22] to [28] described above.

[30]

The resin composition according to [29] described above, further comprising one or more selected from the group consisting of an epoxy resin, an oxetane resin, a maleimide compound, a phenolic resin, a benzoxazine compound, and a compound having a polymerizable unsaturated group.

[31]

The resin composition according to [29] or [30] described above, which further comprises an inorganic filler.

[32]

The resin composition according to [30] or [31] described above, wherein the epoxy resin comprises one or more selected from the group consisting of a biphenyl aralkyl-based epoxy resin, a naphthylene ether-based epoxy resin, a multifunctional phenolic-based epoxy resin, and a naphthalene-based epoxy resin.

[33]

The resin composition according to [31] or [32] described above, wherein a content of the inorganic filler is 50 to 1600 parts by mass based on 100 parts by mass of a resin solid content in the resin composition.

[34]

A hardened product obtained by hardening the resin composition according to any one of [29] to [33] described above.

[35]

A prepreg comprising a base material and the resin composition according to any one of [29] to [33] described above with which the base material is impregnated or coated.

[36]

A laminate comprising a layer comprising at least one of the prepreg according to [35] described above and a metallic foil laminated on one or both surfaces of the layer.

[37]

A sealing material comprising the resin composition according to any one of [29] to [33] described above.

[38]

A fiber-reinforced composite material comprising the resin composition according to any one of [29] to [33] described above and a reinforced fiber.

[39]

An adhesive comprising the resin composition according to any one of [29] to [33] described above.

[40]

A resin composite sheet comprising a support and a resin layer disposed on the surface of the support, wherein the resin layer comprises the resin composition according to any one of [29] to [33] described above.

[41]

A printed wiring board comprising an insulating layer and a conductor layer formed on the surface of the insulating layer, wherein the insulating layer comprises the resin composition according to any one of [29] to [33] described above.

Advantageous Effects of Invention

According to the present invention, a method for efficiently producing a cyanogen halide capable of suppressing side reactions in the production of a cyanate ester compound can be realized. Also, using this cyanogen halide, a method for producing a high-purity cyanate ester compound at a high yield can be realized.

Moreover, according to the present invention, a novel cyanate ester compound used to produce a hardened product having a low coefficient of thermal expansion and also having high flame retardance, low water-absorbing property, heat resistance upon moisture absorption, and heat resistance, a resin composition comprising the aforementioned cyanate ester compound, and the like can be realized.

Furthermore, according to the present invention, a hardened product, a prepreg, a laminate, a sealing material, a fiber-reinforced composite material, an adhesive, a resin composite sheet, a printed wiring board, a metal foil clad laminate, and the like, which have a low coefficient of thermal expansion and also have high flame retardance, low water-absorbing property, heat resistance upon moisture absorption and heat resistance, can be realized. Further, according to a preferred aspect of the present invention, a resin composition consisting only of a non-halogen compound (in other words, a resin composition containing no halogen compounds, namely, a non-halogen resin composition), a prepreg, a laminate, a sealing material, a fiber-reinforced composite material, an adhesive, a resin composite sheet, a printed wiring board, a metal foil clad laminate, and the like, can also be realized, and thus, its industrial practicability is extremely high.

DESCRIPTION OF EMBODIMENTS

Figure 1:
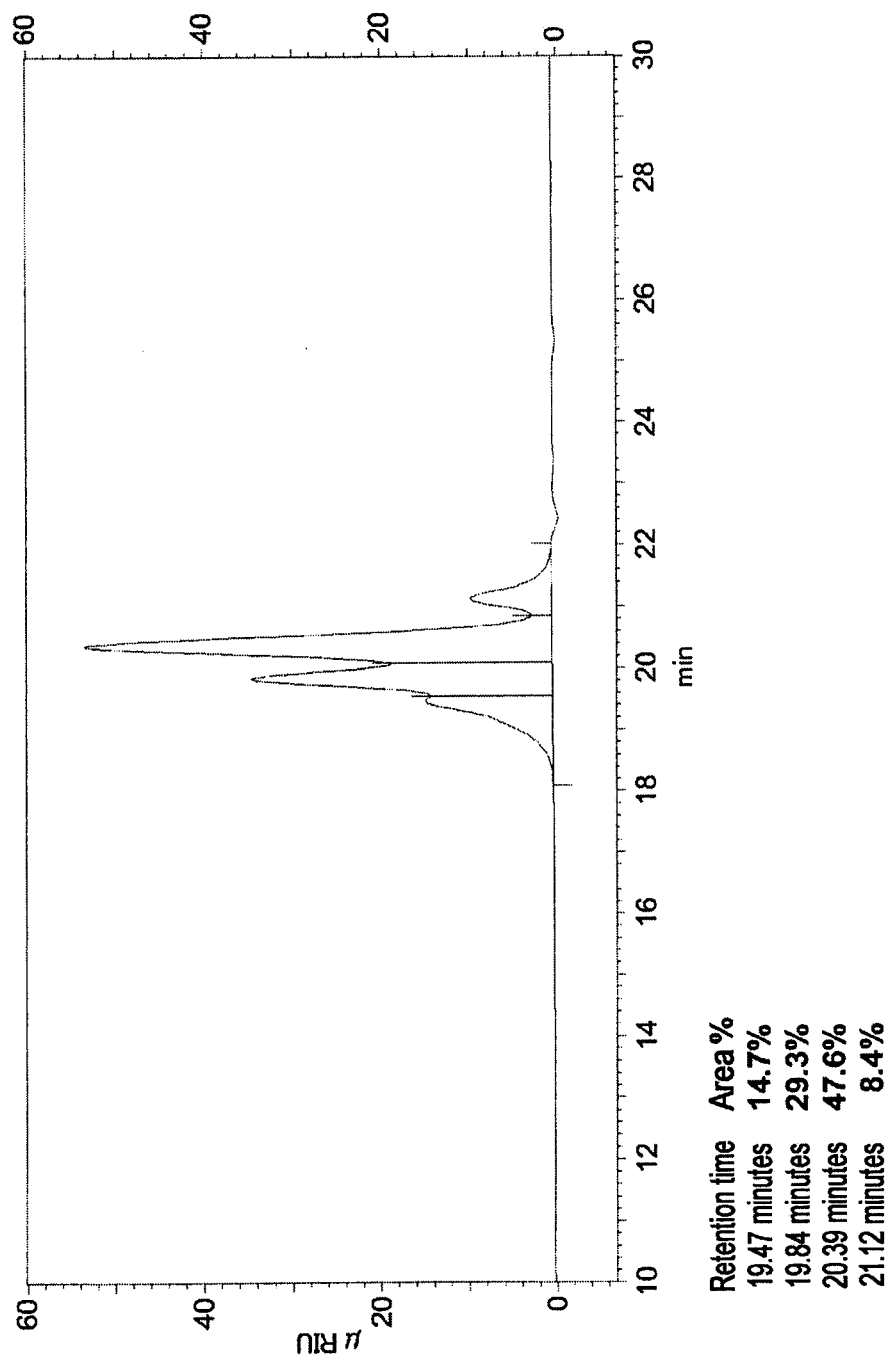
FIG. 1 shows a GPC chart of the phenolic resin obtained in Sample 1.

Hereinafter, the embodiment for carrying out the present invention (hereinafter referred to as "the present embodiment") will be described in detail. However, the present embodiment is not intended to limit the scope of the present invention, and it can be modified in various ways within a range that does not deviate from the gist thereof.

[Method for Producing Cyanogen Halide]

The method for producing a cyanogen halide of the present embodiment comprises a cyanogen halide-producing step of contacting a halogen molecule with an aqueous solution containing hydrogen cyanide and/or a metal cyanide, so that the hydrogen cyanide and/or the metal cyanide is allowed to react with the halogen molecule in a reaction solution to obtain the cyanogen halide, wherein, in the cyanogen halide-producing step, more than 1 mole of the hydrogen cyanide or the metal cyanide is used based on 1 mole of the halogen molecule, and when an amount of substance of an unreacted hydrogen cyanide or an unreacted metal cyanide is defined as mole (A) and an amount of substance of the generated cyanogen halide is defined as mole (B), the reaction is terminated in a state in which (A):(A)+(B) is between 0.00009:1 and 0.2:1.

In short, the method for producing a cyanogen halide of the present embodiment is a production method, in which hydrogen cyanide and/or a metal cyanide are excessively used when the hydrogen cyanide and/or the metal cyanide are allowed to react with a halogen molecule to produce a cyanogen halide (a cyanogen halide-producing step). In addition, the method for producing a cyanate ester compound of the present embodiment is a production method, in which the cyanogen halide obtained by this cyanogen halide-producing step is allowed to react with a hydroxy-substituted aromatic compound (a cyanation step).

[Cyanogen Halide-Producing Step]

First, a step of allowing hydrogen cyanide and/or a metal cyanide to react with a halogen molecule to produce a cyanogen halide (cyanogen halide-producing step) will be described. The cyanogen halide-producing step is a step of contacting a halogen molecule with an aqueous solution containing hydrogen cyanide and/or a metal cyanide, so that the hydrogen cyanide and/or the metal cyanide are allowed to react with the halogen molecule in the reaction solution to obtain a cyanogen halide.

(Hydrogen Cyanide)

In the present embodiment, hydrogen cyanide is used in the form of an aqueous solution. The aqueous solution of hydrogen cyanide is not particularly limited, and a commercially available product can be used. In addition, hydrogen cyanide that has previously been obtained by a reaction of a metal cyanide with an acid may also be used. Using such hydrogen cyanide, side reactions occurring in the cyanogen halide-producing step can be prevented, and the reaction efficiency tends to be further improved.

The reaction of a metal cyanide with an acid can be carried out, for example, by adding an aqueous solution of metal cyanide dropwise to an acid solution, and thus, the reaction method is not particularly limited. Examples of the acid used herein include: inorganic acids such as hydrochloric acid, nitric acid, sulfuric acid, and phosphoric acid; and organic acids such as acetic acid, lactic acid, and propionic acid. The type of the acid is not particularly limited. Among these, inorganic acids are preferable, and hydrochloric acid is more preferable.

(Metal Cyanide)

In addition, in the present embodiment, a metal cyanide is used in the form of an aqueous solution. A generally known metal cyanide can be used, and the type of the metal cyanide is not particularly limited. Specific examples of the metal cyanide include alkaline metal salts such as sodium cyanide and potassium cyanide. The type of the aqueous solution of metal cyanide is not particularly limited, and a commercially available product can be used.

In the cyanogen halide-producing step, the content of hydrogen cyanide and/or a metal cyanide in an aqueous solution is preferably 2 to 20 parts by mass, more preferably 2 to 12 parts by mass, and even more preferably 3 to 12 parts by mass, based on 100 parts by mass of the aqueous solution. By setting the content of hydrogen cyanide and/or a metal cyanide in an aqueous solution within the aforementioned range, side reactions occurring in the cyanogen halide-producing step can be prevented, and the reaction efficiency tends to be further improved.

(Halogen Molecule)

Moreover, the halogen molecule used in the present embodiment is not particularly limited, and examples of the halogen molecule include fluorine, chlorine, bromine, and iodine. The halogen molecule that is in a gaseous or liquid state may be directly used, or it may also be used in the form of a halogen molecule-containing solution, in which the halogen molecule is dissolved in water or an organic solvent. For example, when chlorine is used, gaseous chlorine is preferably used such that it is blown into a reaction solution. In addition, when bromine is used, an aqueous solution prepared by dissolving liquid bromine in water is preferably mixed in a reaction solution.

The organic solvent contained in the halogen molecule-containing solution is not particularly limited. Examples of the organic solvent include halogenated hydrocarbons containing 1 or 2 carbon atoms, such as dichloromethane, chloroform, carbon tetrachloride, dichloroethane, and trichloroethane. In the cyanogen halide-producing step, the concentration of the halogen molecule in the halogen molecule-containing solution is not particularly limited. It is preferably 1% to 30% by mass, more preferably 2% to 20% by mass, and even more preferably 5% to 10% by mass. By setting the content of the halogen molecule in the halogen molecule-containing solution within the aforementioned range, side reactions occurring in the cyanogen halide-producing step can be prevented, and the reaction efficiency tends to be further improved.

(Amount of Hydrogen Cyanide or Metal Cyanide Used)

The amount of hydrogen cyanide or a metal cyanide used is greater than 1 mole, preferably 1.0001 mole or more, and more preferably 1.001 mole or more, based on 1 mole of the halogen molecule. By setting the used amount of hydrogen cyanide or a metal cyanide at more than 1 mole based on 1 mole of the halogen molecule, unreacted halogen remaining in the reaction system can be suppressed. Hence, even if the obtained cyanogen halide-containing solution is directly used to produce a cyanate ester compound in a cyanation step, the generation of reaction by-products due to unreacted halogen, which is hardly removed from the cyanate ester compound by a washing operation and the like, can be suppressed. The reaction by-products caused by such unreacted halogen exert unexpected influence on polymerization control, when the cyanate ester compound is subjected to thermal hardening or the like, and these by-products also exert influence on the physical properties of the obtained hardened product. That is to say, by setting the used amount of hydrogen cyanide or a metal cyanide within the aforementioned range, it becomes easy to control polymerization when the cyanate ester compound is subjected to thermal hardening before use, and also, damage to the insulation properties and the like of a final product can be suppressed.

Moreover, the upper limit of the used amount of hydrogen cyanide or a metal cyanide is not particularly limited. It is preferably 2 moles or less, based on 1 mole of the halogen molecule. By setting the used amount of hydrogen cyanide or a metal cyanide at 2 moles or less, in the subsequent step of producing a cyanate ester compound, a decrease in the amount of a cyanogen halide due to the reaction of unreacted hydrogen cyanide or unreacted metal cyanide with the generated cyanogen halide (subgeneration of dicyan) can be prevented, and a cyanate ester compound tends to be obtained at a high yield.

(Contacting Operation)

The operation to contact an aqueous solution containing hydrogen cyanide and/or a metal cyanide with halogen molecules is not particularly limited, as long as they are allowed to physically come into contact with each other. Examples of the contacting operation include a method of blowing halogen molecules into an aqueous solution containing hydrogen cyanide and/or a metal cyanide, a method of adding a solution containing halogen molecules dropwise to an aqueous solution containing hydrogen cyanide and/or metal cyanide, and a method of adding an aqueous solution containing hydrogen cyanide and/or a metal cyanide dropwise to a solution containing halogen molecules. In addition to these methods, it may be also possible to stir the reaction solution.

The reaction temperature applied in the reaction of hydrogen cyanide and/or a metal cyanide with halogen molecules is not particularly limited. From the viewpoint of the suppression of the hydrolysis of the generated cyanogen halide and the prevention of evaporative loss when the cyanogen halide is a cyanogen chloride, the reaction temperature is preferably −10° C. to 5° C., more preferably −7° C. to 5° C., and even more preferably −5° C. to 5° C.

The reaction pressure applied in the reaction of hydrogen cyanide and/or a metal cyanide with halogen molecules may be either an ordinary pressure, or a pressure higher than such an ordinary pressure. In addition, the reaction atmosphere is not particularly limited, and for example, inert gas such as nitrogen, helium or argon may be supplied into the reaction system, as necessary.

Moreover, the time, in which an aqueous solution containing hydrogen cyanide and/or a metal cyanide is contacted with halogen atoms, is not particularly limited. It is preferably 10 minutes to 20 hours, and more preferably 30 minutes to 15 hours. Furthermore, after completion of the contacting operation, it is preferable to stir the reaction solution for 10 minutes to 10 hours, while keeping the same reaction temperature as described above. By setting the reaction time within the aforementioned range, the cyanogen halide of interest tends to be obtained with higher economical and industrial efficiency. The term "contacting time" is used herein to mean, for example, a period of time in which halogen molecules are blown into an aqueous solution containing hydrogen cyanide and/or a metal cyanide, or a period of time in which a solution containing halogen molecules is added dropwise to an aqueous solution containing hydrogen cyanide and/or metal cyanide, or a period of time in which an aqueous solution containing hydrogen cyanide and/or a metal cyanide is added dropwise to a solution containing halogen molecules, or the like.

In the reaction of hydrogen cyanide and/or a metal cyanide with halogen molecules, the pH of the reaction solution is not particularly limited. It is preferably less than 7, more preferably 6 or less, and even more preferably 5 or less. By performing the reaction while keeping the state in which the pH of the reaction solution is less than 7, the generation of a polymer represented by $(CN)_n$ (paracyanogen) is suppressed, and the production efficiency of a cyanogen halide tends to be further improved.

In particular, when a metal cyanide is allowed to react with halogen molecules, the pH of the reaction solution tends to be shifted to the basic side due to the hydrolysis of the metal cyanide. Thus, it is preferable that an acid be added to the reaction system while appropriately measuring the pH of the reaction solution with a pH meter, and that the pH of the reaction solution be kept at less than pH 7. The acid used herein is not particularly limited. Examples of the acid include: inorganic acids such as hydrochloric acid, nitric acid, sulfuric acid, and phosphoric acid; and organic acids such as acetic acid, lactic acid, and propionic acid. The amount of the acid added is not particularly limited. Taking into consideration the hydrolysis of a cyanogen halide with hydrochloric acid and the pH kept at less than 7, the acid is preferably used at an equivalent ratio of 0.1:1 to 1.1:1, based on the cyano group of the metal cyanide.

(Reaction Terminal Point)

In the present embodiment, the amount of substance of unreacted hydrogen cyanide or unreacted metal cyanide is used as a standard for the terminal point of the reaction. Specifically, the reaction of hydrogen cyanide and/or a metal cyanide with halogen molecules is terminated in a state in which, when the amount of substance of the unreacted hydrogen cyanide or the unreacted metal cyanide is defined as mole (A) and the amount of substance of the generated cyanogen halide is defined as mole (B), (A):(A)+(B) becomes 0.00009:1 to 0.2:1, preferably 0.00011:1 to 0.19650:1, and more preferably 0.00014:1 to 0.19100:1. By defining such a state as a reaction terminal point, in the subsequent method for producing a cyanate ester compound, a decrease in the amount of a cyanogen halide due to the reaction of the unreacted hydrogen cyanide or the unreacted metal cyanide with the generated cyanogen halide (subgeneration of dicyan) can be prevented. In addition, it becomes also possible to obtain a cyanate ester compound at a high yield, without increasing the amount of a basic compound used.

Herein, the term "reaction terminal point" is used in the present embodiment to mean a stage 15 minutes after the atmosphere in the reaction system is converted to an atmosphere of inert gas such as nitrogen or argon, after completion of the contacting operation of an aqueous solution containing hydrogen cyanide and/or a metal cyanide with halogen molecules, or after completion of a stirring operation carried out as any given operation after the contacting operation. Specifically, the reaction terminal point means a time point 15 minutes have passed from the time point at which the atmosphere in the reaction system had been converted to an inert gas atmosphere such as nitrogen or argon, after the supply of a predetermined amount of halogen molecule depending on the amount of hydrogen cyanide or a metal cyanide used to a reaction system.

Further, it is preferable to terminate the reaction in a state in which the inversion percentage of the halogen molecule becomes 99.9% or more.

The thus obtained reaction product may comprise cyanogen halide, unreacted hydrogen cyanide, and unreacted metal cyanide. The mass ratio of these substances can be analyzed by gas chromatography. In addition, the molar numbers of cyanogen halide, unreacted hydrogen cyanide, and unreacted metal cyanide can also be calculated based on the mass obtained by gas chromatography. Moreover, the remaining of unreacted halogen can be qualitatively detected based on the electric potential of the reaction solution, or the presence or absence of coloration of an organic phase after extraction of the reaction solution with dichloromethane (wherein the organic phase becomes colorless if the inversion percentage of the halogen molecule is 99.9% or more).

A cyanogen halide solution obtained as a result of the reaction of hydrogen cyanide and/or a metal cyanide with halogen molecules can be directly used for a reaction of the cyanogen halide with a hydroxy-substituted aromatic compound in a cyanation step. Alternatively, the cyanogen halide solution may be used, after an organic solvent and/or water, in which the solubility of the cyanogen halide is high, have been added to the reaction system in the cyanation step, or further, the cyanogen halide solution may also be used, after the cyanogen halide has been extracted from the cyanogen halide solution with an organic solvent (extraction step). By carrying out such treatments, hydrogen halide, which is subgenerated in an amount equal to the cyanogen halide during the production of the cyanogen halide and promotes the hydrolysis of the cyanogen halide, can be diluted or eliminated. Thereby, the contact of the cyanogen halide with the hydrogen halide can be avoided as much as possible, and the loss of the cyanogen halide tends to be prevented.

The organic solvent used to solubilize and extract the cyanogen halide is not particularly limited, and for example, it is preferably an organic solvent, which is immiscible with water and which solubilizes the cyanogen halide but does not solubilize hydrogen halide. Such an organic solvent is not particularly limited. Examples of the organic solvent include halogenated hydrocarbons containing 1 to 2 carbon atoms, such as dichloromethane, chloroform, carbon tetrachloride, dichloroethane, and trichloroethane. Among these, dichloromethane is preferable from the viewpoint of the distribution ratio of the cyanogen halide, various conditions for the extraction operation, such as phase separation property or miscibility, and the safety of an organic solvent used for extraction. The organic solvent can be used singly or in combination of two or more types.

In addition, the water used in the cyanation step is not particularly limited. Examples of the water include tap water, distilled water, and deionized water. Among these, distilled water or deionized water having a few impurities is preferable from the viewpoint of efficiently obtaining a cyanate ester compound of interest.

The extraction operation in the extraction step may be either batch-wise extraction or continuous extraction. In the case of the batch-wise extraction, it is difficult to completely extract the cyanogen halide by only a single extraction operation. Hence, it is preferable to carry out the extraction operation several times, and in general, two to four times. The temperature applied during the extraction is preferably 5° C. or lower from the viewpoint of suppression of the hydrolysis of the cyanogen halide. In addition, the amount of an organic solvent used for the extraction is not particularly limited, and it may be the amount of an organic solvent, in which the cyanogen halide in the reaction solution can be dissolved, or a larger amount. The organic solvent is used at a volume ratio of 0.3:1 or more, and preferably 0.5:1 to 3:1, based on the volume of the obtained cyanogen halide solution.

It is to be noted that the organic solvent used in the aforementioned extraction step may also be used as a solvent that solubilizes halogen molecules in the cyanogen halide-producing step.

[Method for Producing a Cyanate Ester Compound]

Next, a method for producing a cyanate ester compound by allowing the cyanogen halide obtained by the reaction of hydrogen cyanide and/or a metal cyanide with a halogen molecule (cyanogen halide-producing step) to react with a hydroxy-substituted aromatic compound (cyanation step) will be described.

[Cyanation Step]

The cyanation step is a step of allowing the cyanogen halide obtained by the above described method for producing a cyanogen halide to react with a hydroxy-substituted aromatic compound in the presence of a basic compound in a reaction solution, to obtain a cyanate ester compound. In addition, the method for producing a cyanate ester compound of the present embodiment may comprise a step of preparing a cyanogen halide and a hydroxy-substituted aromatic compound.

The specific operation is not particularly limited. Example of the operation include a method of contacting a solution containing a cyanogen halide and a hydroxy-substituted aromatic compound with a solution containing a basic compound, and a method of contacting a solution containing a cyanogen halide with a solution containing a basic compound and a hydroxy-substituted aromatic compound. Hence, by previously dissolving a hydroxy-substituted aromatic compound serving as a reaction substrate in a solution containing a cyanogen halide or a solution containing a basic compound, and then by contacting the cyanogen halide solution with the basic compound solution, the hydroxy-substituted aromatic compound can be uniformly dissolved in the reaction solution, side reactions can be suppressed, and a cyanate ester compound with a higher purity tends to be obtained at a high yield. Hereinafter, the solution containing a cyanogen halide may also be referred to as a "cyanogen halide solution," and the solvent may comprise a hydroxy-substituted aromatic compound. Moreover, the solution containing a basic compound may also be referred to as a "basic compound solution," and the solvent may comprise a hydroxy-substituted aromatic compound.

The solution containing a basic compound preferably comprises an organic solvent or water. By allowing the basic compound solution to comprise an organic solvent, side reactions can be suppressed, and a cyanate ester compound with a higher purity tends to be obtained at a high yield. Moreover, by allowing the basic compound solution to comprise water, side reactions can be suppressed, and a cyanate ester compound with a higher purity tends to be obtained at a high yield.

The operation to contact a cyanogen halide solution with a basic compound solution may be either a semibatch operation or a continuous flow operation. The contacting operation is not particularly limited. Examples of the contacting operation include a method (a) of adding a basic compound solution dropwise to a cyanogen halide solution during stirring and mixing, a method (b) of adding a cyanogen halide solution dropwise to a basic compound solution during stirring and mixing, and a method (c) of supplying a portion of a cyanogen halide solution and a portion of a basic compound solution to a reaction vessel, continuously or intermittently, and alternatively or simultaneously.

Among the methods (a) to (c), the method (a) is preferable from the viewpoint of suppressing side reactions and obtaining a higher-purity cyanate ester compound at a high yield. Moreover, a method of dividing a basic compound solution containing a hydroxy-substituted aromatic compound and then adding the obtained aliquots dropwise to a cyanogen halide solution during stirring and mixing is more preferable. By applying such a method, side reactions can be suppressed, and the reaction can be completed with no remaining hydroxy-substituted aromatic compounds, and further, a higher-purity cyanate ester compound tends to be obtained at a high yield. The number of such divided dropping operations is not particularly limited. It is preferably two to five times. Furthermore, either a single identical basic compound or different basic compounds may be used for each division.

(Cyanogen Halide)

The cyanogen halide used in the cyanation step is a cyanogen halide obtained by the aforementioned cyanogen halide-producing step. Such a cyanogen halide can be used in the form of a predetermined solution, and thus, the form of the cyanogen halide is not particularly limited. Specific examples of the cyanogen halide solution include an unchanged cyanogen halide solution d obtained by the cyanogen halide-producing step, a cyanogen halide solution e obtained by adding an organic solvent to the cyanogen halide solution d, a cyanogen halide solution f obtained by adding an organic solvent and water to the cyanogen halide solution d, a cyanogen halide solution g obtained by extracting a cyanogen halide from the cyanogen halide solution d using an organic solvent, a cyanogen halide solution h obtained by adding only an organic solvent to the cyanogen halide solution g, and a cyanogen halide solution i obtained by adding an organic solvent and water, or only water, to the cyanogen halide solution g.

The cyanogen halide solutions e, f, h, and i preferably comprise an organic solvent or a mixture of water and an organic solvent. By allowing the cyanogen halide solution to comprise an organic solvent, hydrogen halide, which is subgenerated in an amount equal to the cyanogen halide during the production of the cyanogen halide and promotes the hydrolysis of the cyanogen halide, can be diluted. Thereby, the contact of the cyanogen halide with the hydrogen halide can be avoided as much as possible, and the loss of the cyanogen halide tends to be prevented. Moreover, by allowing the cyanogen halide solution to comprise a mixture of water and an organic solvent, hydrogen halide, which is subgenerated in an amount equal to the cyanogen halide during the production of the cyanogen halide and promotes the hydrolysis of the cyanogen halide, can be diluted or eliminated. Thereby, the contact of the cyanogen halide with the hydrogen halide can be avoided as much as possible, and the loss of the cyanogen halide tends to be prevented.

The organic solvent comprised in the cyanogen halide solution h is not particularly limited. Examples of the organic solvent used include: ketone solvents such as acetone, methyl ethyl ketone, and methyl isobutyl ketone; aromatic solvents such as benzene, toluene, and xylene; ether solvents such as diethyl ether, dimethyl cellosolve, diglyme, tetrahydrofuran, methyl tetrahydrofuran, dioxane, and tetraethylene glycol dimethyl ether; halogenated hydrocarbon solvents such as dichloromethane, chloroform, carbon tetrachloride, dichloroethane, trichloroethane, chlorobenzene, and bromobenzene; alcohol solvents such as methanol, ethanol, isopropanol, methyl cellosolve, and propylene glycol monomethyl ether; aprotic polar solvents such as N,N-dimethylformamide, N-methylpyrrolidone, 1,3-dimethyl-2-imidazolidone, and dimethyl sulfoxide; nitrile solvents such as acetonitrile and benzonitrile; nitro solvents such as nitromethane and nitrobenzene; ester solvents such as ethyl acetate and ethyl benzoate; and hydrocarbon solvents such as cyclohexane. As such, many types of solvents can be used. These organic solvents can be used singly or in combination of two or more types, depending on the type of a hydroxy-substituted aromatic compound.

A generally known organic solvent can be used as an organic solvent comprised in the cyanogen halide solutions e, f, and i, as long as it is immiscible with water and is inactive in the reaction. Thus, the type of the organic solvent is not particularly limited. Specific examples of the organic solvent include: halogenated hydrocarbon solvents such as dichloromethane, chloroform, carbon tetrachloride, dichloroethane, trichloroethane, chlorobenzene, and bromobenzene; aliphatic solvents such as n-hexane, cyclohexane, isooctane, cyclohexanone, cyclopentanone, and 2-butanone; aromatic solvents such as benzene, toluene, xylene, and ethyl benzene; ketone solvents such as methyl ethyl ketone and methyl isobutyl ketone; nitrile solvents such as benzonitrile; nitro solvents such as nitrobenzene; ether solvents such as diethyl ether, diisopropyl ether, and tetrahydrofuran; and ester solvents such as ethyl acetate and ethyl benzoate. Among these, halogenated hydrocarbon solvents containing 1 or 2 carbon atoms, such as dichloromethane, chloroform, carbon tetrachloride, dichloroethane, and trichloroethane, are more preferable. These organic solvents can be used singly or in combination of two or more types, depending on the type of a hydroxy-substituted aromatic compound.

The water comprised in the cyanogen halide solutions f and i is not particularly limited. Examples of the water include tap water, distilled water, and deionized water. Among these, distilled water or deionized water having a few impurities is preferable from the viewpoint of efficiently obtaining a cyanate ester compound of interest.

The mass ratio of the water to the organic solvent comprised in the cyanogen halide solution f and i is not particularly limited. It is preferably 1/100 to 100/1, more preferably 1/10 to 10/1, and even more preferably 1/5 to 5/1.

When the cyanogen halide solution comprises a hydroxy-substituted aromatic compound, the content of the solvent is not particularly limited. It is preferably 1.0 to 100 parts by mass, and more preferably 2.0 to 50 parts by mass, based on 1 part by mass of the hydroxy-substituted aromatic compound. By setting the content of the solvent within the aforementioned range, the hydroxy-substituted aromatic compound can be uniformly dissolved in the solution, and the production efficiency of a cyanate ester compound tends to be further improved.

The amount of the cyanogen halide used in the cyanation step is not particularly limited. The cyanogen halide is used in an amount of preferably 0.5 to 5 moles, preferably 0.7 to 4.5 moles, and even more preferably 1.0 to 3.5 moles, based on 1 mole of the hydroxy group of the hydroxy-substituted aromatic compound. By setting the used amount of the cyanogen halide within the aforementioned range, the yield of the cyanate ester compound tends to be further improved, with no remaining unreacted hydroxy-substituted aromatic compounds.

(Hydroxy-Substituted Aromatic Compound)

The hydroxy-substituted aromatic compound used in the present embodiment is not particularly limited, as long as it is an aromatic compound having at least one phenolic hydroxy group. Examples of such a hydroxy-substituted aromatic compound include a phenolic resin having a polynaphthylene ether structure and a compound represented by the following general formula (1). Herein, examples of the compound represented by the following general formula (1) include (1a) a naphthol aralkyl resin, (1b) a phenolic resin having an adamantane structure, and (1c) those other than (1a) and (1b) above (hereinafter also referred to as "other hydroxy-substituted aromatic compounds"). Hereinafter, individual hydroxy-substituted aromatic compounds will be described.

(Phenolic Resin Having Polynaphthylene Ether Structure)

The phenolic resin having a polynaphthylene ether structure is not particularly limited, as long as it has a polynaphthylene ether structure in which a naphthalene ring is bonded to another naphthalene ring via an oxy group, and a phenolic hydroxy group on the naphthalene ring. The total number of naphthalene rings per molecule is not particularly limited, and it is preferably 2 to 8. By allowing the phenolic resin to have a polynaphthylene ether structure, the formation of char (carbonaceous residue) is promoted during combustion of a hardened product obtained from a cyanate ester, and excellent flame retardance is provided, and also, high heat resistance can be obtained.

Herein, the number of oxy groups bonded to a single naphthalene ring is not particularly limited, and it is preferably 1 to 3. From the viewpoint of the flowability of the phenolic resin having a polynaphthylene ether structure, the number of the oxy groups is more preferably 2. Herein, the binding positions of the oxy groups on the naphthalene ring is preferably position 1,3, position 1,6, position 1,7, position 1,8, position 2,3, or position 2,7. Among these, the binding positions of the oxy groups on the naphthalene ring are more preferably position 1,6 or position 2,7, from the viewpoint of ease of production, and the binding position is even more preferably position 2,7, from the viewpoint of good balance between flowability and flame retardance. Moreover, from the viewpoint of flame retardant effect, it is preferable that the naphthalene ring do not have substituents other than the oxy group thereon.

It is to be noted that the phenolic resin having a polynaphthylene ether structure may have a molecular structure in which a plurality of naphthalene rings form direct bonds.

The phenolic resin having a polynaphthylene ether structure is not particularly limited. Examples of such a phenolic resin include one or more selected from the group consisting of a compound represented by the following general formula (3) and compounds represented by the following general formula (5) to (8), which are disclosed in Japanese Patent No. 4259536. In addition, as a phenolic resin having a polynaphthylene ether structure, a synthetic product obtained in a laboratory scale can also be used, and an example of such a synthetic product is EXB-6000 manufactured by DIC Corporation.

[Formula 15]

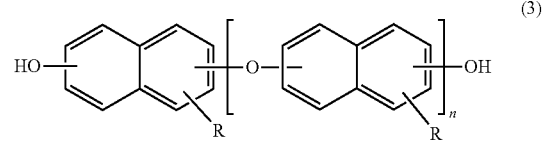

(3)

wherein R each independently represent a hydrogen atom, an aryl group such as a benzyl group and an alkyl group, or the following general formula (4); and n represents an integer of 1 to 20 and it is more preferably an integer of 1 to 10.

[Formula 16]

(4)

wherein Ar each independently represent an aryl group such as a phenylene group and a naphthylene group; and m represents an integer of 1 or 2.

[Formula 17]

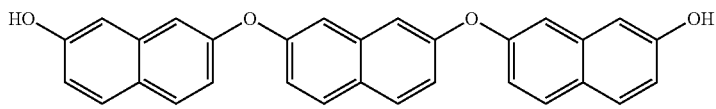

(5)

[Formula 18]

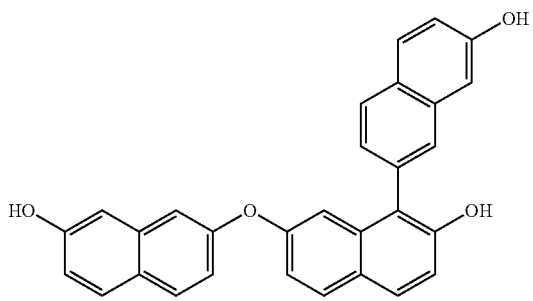

(6)

[Formula 19]

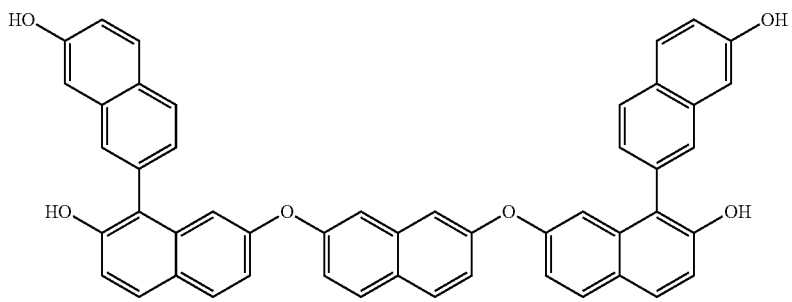

(7)

[Formula 20]

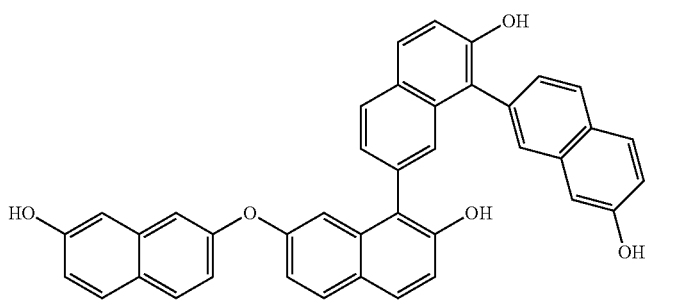

(8)

The phenolic resin having a polynaphthylene ether structure can be obtained by a dehydration condensation reaction. The dehydration condensation reaction is a reaction of subjecting a polyhydric hydroxynaphthalene compound having two or more phenolic hydroxy groups in one molecule to a dehydration condensation reaction in the presence of a basic catalyst, before the cyanation step, to obtain a hydroxy-substituted aromatic compound. The obtained hydroxy-substituted aromatic compound is not particularly limited. An example of the hydroxy-substituted aromatic compound is a phenolic resin having a structure in which a naphthalene ring is bonded to another naphthalene ring via an oxygen atom (hereinafter also referred to as an "oxy group") (hereinafter also referred to as a "polynaphthylene ether structure").

(Polyhydric Hydroxynaphthalene Compound)

The polyhydric hydroxynaphthalene compound used in the dehydration condensation reaction is not particularly limited. Examples of the polyhydric hydroxynaphthalene compound include: dihydroxynaphthalene such as 1,3-dihydroxynaphthalene, 1,6-dihydroxynaphthalene, 1,7-dihydroxynaphthalene, 1,8-dihydroxynaphthalene, 2,3-dihydroxynaphthalene, and 2,7-dihydroxynaphthalene; trihydroxynaphthalene such as 1,2,3-trihydroxynaphthalene; and compounds having, as a substituent, an alkyl group containing 1 to 4 carbon atoms or a phenyl group on the aromatic ring of these compounds. Among these compounds, 1,3-dihydroxynaphthalene, 1,6-dihydroxynaphthalene, 1,8-dihydroxynaphthalene, and 2,7-dihydroxynaphthalene are preferable. From the viewpoint of a possible reduction in the melt viscosity of the obtained phenolic resin having a polynaphthylene ether structure or a cyanate ester compound that is a cyanated product of the phenolic resin, and also from the viewpoint of flame retardance, among the aforementioned compounds, 1,6-dihydroxynaphthalene and 2,7-dihydroxynaphthalene are more preferable. Moreover, in addition to the aforementioned advantages, from the viewpoint of having a good balance between flowability and flame retardance of the obtained cyanate ester compound, 2,7-dihydroxynaphthalene is particularly preferable. These compounds can be used singly or in combination of two or more types.

(Basic Catalyst)

The basic catalyst used in the dehydration condensation reaction is not particularly limited. Examples of the basic catalyst include: alkali metal hydroxides such as sodium hydroxide and potassium hydroxide; alkali metal carbonates such as sodium carbonate and potassium carbonate; and phosphorus compounds such as triphenylphophine. These basic catalysts may be used singly or in combination of two or more types.

The amount of the basic catalyst used can be appropriately selected depending on the type, a desired reaction rate, and the like. For example, when alkali metal hydroxide is used as a basic catalyst, the amount of the basic catalyst used is not particularly limited, and it is used in an amount of preferably 0.01 to 0.5 moles, and more preferably 0.01 to 0.1 mole, based on 1 mole of the phenolic hydroxy group of the polyhydric hydroxynaphthalene compound.

The dehydration condensation reaction can be carried out with no solvents or in the presence of a solvent, depending on the type of the polyhydric hydroxynaphthalene compound used. A solvent-recovering step and the like become unnecessary, if the reaction is carried out with no solvents. In addition, if the reaction is carried out in the presence of a solvent, a homogenous reaction solution can be easily formed, and thus, the reaction tends to stably progress.

The solvent used in the dehydration condensation reaction is not particularly limited. Examples of the solvent include: alcohols such as benzyl alcohol, cyclohexanol, and amyl alcohol; ethylene glycols such as ethylene glycol, diethylene glycol, triethylene glycol, and polyethylene glycol; mono or diethers of ethylene glycol or diethylene glycol, such as ethylene glycol monomethyl ether, ethylene glycol monoethyl ether, ethylene glycol monopropyl ether, diethylene glycol monomethyl ether, diethylene glycol monoethyl ether, diethylene glycol monopropyl ether, diethylene glycol monobutyl ether, ethylene glycol dimethyl ether, ethylene glycol diethyl ether, ethylene glycol dipropyl ether, diethylene glycol dimethyl ether, diethylene glycol diethyl ether, and diethylene glycol dipropyl ether; and chlorobenzene and nitrobenzene. These solvents may be used singly or in combination of two or more types. Using such a solvent, precipitation of salts of a polyhydric hydroxynaphthalene compound in the dehydration condensation reaction can be prevented, and a phenolic resin having a polynaphthylene ether structure can be stably obtained.

The reaction temperature applied during the dehydration condensation reaction is not particularly limited. It is preferably 100° C. to 300° C., and more preferably 150° C. to 250° C. In addition, the reaction time is not particularly limited, either, and it is preferably in a range in which the aforementioned reaction temperature conditions can be maintained for 1 to 10 hours. Moreover, from the viewpoint of quickly promoting the dehydration condensation reaction and further improving productivity, it is preferable to distill away water generated during the dehydration condensation reaction from the reaction system, using a fractionating column or the like.

After completion of the dehydration condensation reaction, the generated product is directly solidified so that a phenolic resin having a polynaphthylene ether structure can be collected. Alternatively, a catalyst is eliminated from the product by a neutralization treatment, a water-washing treatment or decomposition, and then, a phenolic resin having a polynaphthylene ether structure can be collected by a common operation such as extraction or distillation. The neutralization treatment or the water-washing treatment may be carried out according to an ordinary method, and for example, an acidic substance such as hydrochloric acid, oxalic acid, acetic acid, monosodium phosphate, or carbon dioxide can be used.

The thus obtained phenolic resin having a polynaphthylene ether structure can be directly used for various intended uses. As necessary, fractionation operations such as distillation, a column treatment, or extraction with an aqueous solution of alkali are carried out, so that the content of a polyhydric hydroxynaphthalene compound that is an unreacted product may be reduced, or each product may be isolated to a single component.

(Compound Represented by the Following General Formula (1))

Next, a compound represented by the following general formula (1) will be described.

[Formula 21]

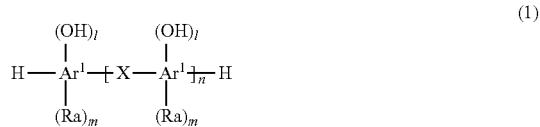

wherein $Ar^1$ each independently represent a phenylene group optionally having a substituent, a naphthylene group optionally having a substituent, or a biphenylene group optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; m represents the number of Ra bonded to $Ar^1$, wherein it is an integer of 4-1 when $Ar^1$ represents a phenylene group, it is an integer of 6-1 when $Ar^1$ represents a naphthylene group, and it is an integer of 8-1 when $Ar^1$ represents a biphenylene group; n represents the average number of repetitions, which is an integer of 0 to 50; and X each independently represent a single bond, a divalent organic group containing 1 to 50 carbon atoms (wherein a hydrogen atom may be optionally replaced by a heteroatom), a divalent organic group containing 1 to 10 nitrogen atoms, a carbonyl group (—CO—), a carboxy group (—C(=O)O—), a carbonyl dioxide group (—OC(=O)O—), a sulfonyl group (—SO$_2$—), or a divalent sulfur atom or a divalent oxygen atom.

$Ar^1$ each independently represent a phenylene group optionally having a substituent, a naphthylene group optionally having a substituent, or a biphenylene group optionally having a substituent, in which the hydrogen element at any given position is replaced by with an Ra group and a hydroxy group.

Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms.

The alkyl group containing 1 to 6 carbon atoms represented by Ra optionally has a chain structure, a branched structure, or a cyclic structure. Such an alkyl group is not particularly limited. Examples of the alkyl group include a methyl group, an ethyl group, a propyl group, an isopropyl group, an n-butyl group, an isobutyl group, a tert-butyl group, an n-pentyl group, a 1-ethylpropyl group, a 2,2-dimethylpropyl group, a cyclopentyl group, a hexyl group, a cyclohexyl group, and a trifluoromethyl group. The hydrogen atom in the alkyl group is optionally replaced by: halogen atoms such as fluorine or chlorine; alkoxy groups such as a methoxy group or a phenoxy group; a cyano group; a hydroxy group; and the like.

The aryl group containing 6 to 12 carbon atoms represented by Ra is not particularly limited. Examples of the aryl group include a phenyl group, a xylyl group, a mesityl group, a naphthyl group, a phenoxyphenyl group, an ethylphenyl group, an o-, m- or p-fluorophenyl group, a dichlorophenyl group, a dicyanophenyl group, a trifluorophenyl group, a methoxyphenyl group, and an o-, m- or p-tolyl group. The hydrogen atom in the aryl group is optionally replaced by: halogen atoms such as fluorine or chlorine; alkoxy groups such as a methoxy group or a phenoxy group; a cyano group; a hydroxy group; and the like.

The alkoxy group containing 1 to 4 carbon atoms represented by Ra optionally has a chain structure, a branched structure, or a cyclic structure. Such an alkoxy group is not particularly limited. Examples of the alkoxy group include a methoxy group, an ethoxy group, a propoxy group, an isopropoxy group, an n-butoxy group, an isobutoxy group, and a tert-butoxy group. The hydrogen atom in the alkoxy group is optionally replaced by: halogen atoms such as fluorine or chlorine; alkoxy groups such as a methoxy group or a phenoxy group; a cyano group; a hydroxy group; and the like.

X each independently represent a single bond, a divalent organic group containing 1 to 50 carbon atoms (wherein the hydrogen atom is optionally replaced by a heteroatom), a divalent organic group containing 1 to 10 nitrogen atoms, a carbonyl group (—CO—), a carboxy group (—C(=O)O—), a carbonyl dioxide group (—OC(=O)O—), a sulfonyl group (—SO$_2$—), or a divalent sulfur atom or a divalent oxygen atom.

The divalent organic group containing 1 to 50 carbon atoms represented by X is not particularly limited. Examples of the divalent organic group containing 1 to 50 carbon atoms include a methylene group, an ethylene group, a trimethylene group, a propylene group, a cyclopentylene group, a cyclohexylene group, a trimethylcyclohexylene group, a biphenylmethylene group, a dimethylmethylene-phenylene-dimethylmethylene group, a fluorenediyl group, and a phthalide-diyl group. The hydrogen atom in the divalent organic group is optionally replaced by a heteroatom. The heteroatom is not particularly limited, and examples of the heteroatom include halogen atoms such as fluorine or chlorine. The hydrogen atom in the divalent organic group containing 1 to 50 carbon atoms is optionally replaced by alkoxy groups such as a methoxy group or a phenoxy group, a cyano group, and the like.

The divalent organic group containing 1 to 10 nitrogen atoms represented by X is not particularly limited. Examples of the divalent organic group containing 1 to 10 nitrogen atoms include a group represented by —N—R—N—, an imino group, and a polyimide group.

X in the above general formula (1) is preferably a divalent organic group containing 1 to 50 carbon atoms represented by the following general formula (2), or a divalent group selected from the group consisting of structures represented by the following general formulae (2a), (2b), (2c), (2d), (2e), (2f), (2g), (2h), (2i) and (2j):

[Formula 22]

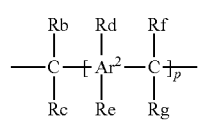
(2)

wherein Ar$^2$ each independently represent a phenylene group optionally having a substituent, a naphthylene group optionally having a substituent, or a biphenylene group optionally having a substituent; Rb, Rc, Rf, and Rg each independently represent a hydrogen atom, an alkyl group containing 1 to 6 carbon atoms and optionally having a substituent, or an aryl group containing 6 to 12 carbon atoms and optionally having a substituent; Rd and Re each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group; and p represents an integer of 0 to 5,

[Formula 23]

(2a)

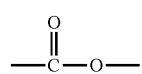
(2b)

(2c)

(2d)

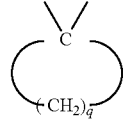
(2e)

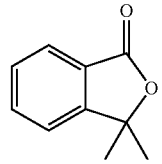
(2f)

-continued

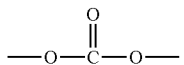

(2g)

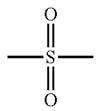

(2h)

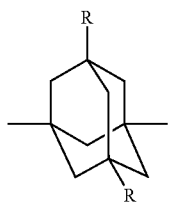

(2i)

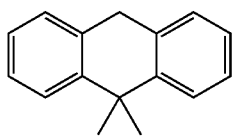

(2j)

wherein, in the formula (2d), q represents an integer of 4 to 7, and in the formula (2i), R each independently represent a hydrogen atom or an alkyl group containing 1 to 6 carbon atoms and optionally having a substituent.

$Ar^2$ in the above general formula (2) each independently represent a phenylene group, a naphthylene group, or a biphenylene group. The $Ar^2$ is not particularly limited, and examples thereof include a 1,4-phenylene group, a 1,3-phenylene group, a 2,6-naphthylene group, a 1,5-naphthylene group, a 1,6-naphthylene group, a 1,8-naphthylene group, a 1,3-naphthylene group, a 1,4-naphthylene group, a 4,4'-biphenylene group, a 2,4'-biphenylene group, a 2,2'-biphenylene group, a 2,3'-biphenylene group, a 3,3'-biphenylene group, and a 3,4'-biphenylene group.

Rb, Rc, Rf, and Rg in the above general formula (2) each independently represent a hydrogen atom, an alkyl group containing 1 to 6 carbon atoms and optionally having a substituent, and an aryl group containing 6 to 12 carbon atoms and optionally having a substituent. In addition, Rd and Re in the above general formula (2) each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group. The alkyl group containing 1 to 6 carbon atoms, aryl group containing 6 to 12 carbon atoms, and alkoxy group containing 1 to 4 carbon atoms, which are represented by Rb, Rc, Rd, Re, Rf, and Rg, are not particularly limited. Examples thereof include the same groups as those exemplified for Ra in the above general formula (1). In addition, the hydrogen atom in each of the phenylene group, naphthylene group, biphenylene group, alkyl group containing 1 to 6 carbon atoms, aryl group containing 6 to 12 carbon atoms, and alkoxy group containing 1 to 4 carbon atoms in the above general formula (2) is optionally replaced by: halogen atoms such as fluorine or chlorine; alkoxy groups such as a methoxy group or a phenoxy group; a cyano group; a hydroxy group; and the like.

((1a) Naphthol Aralkyl Resin)

The naphthol aralkyl resin is not particularly limited, as long as it has a structure in which a naphthalene ring having a hydroxy group is bonded to a benzene ring via an alkyl group. An example of such a naphthol aralkyl resin is a compound wherein, in the above general formula (1), $Ar^1$ represents a naphthylene group, X is represented by the above general formula (2), and $Ar^2$ represents a phenylene group. Specifically, a compound represented by the following general formula (19) is preferable. In the compound represented by the following general formula (19), two methylene groups bonded to a benzene ring can be bonded thereto at an ortho position, a meta position, or a para position. Among these, the two methylene groups bonded to the benzene ring are preferably bonded to the meta position and/or para position of the benzene ring. A hardened product of a cyanate ester obtained using a naphthol aralkyl resin tends to have a low coefficient of thermal expansion and also have high flame retardance, low water-absorbing property, and heat resistance upon moisture absorption.

[Formula 24]

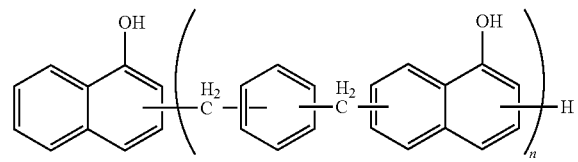

(19)

wherein n represents an integer of 1 to 50, and preferably 1 to 10.

The naphthol aralkyl resin is not particularly limited. Examples of the naphthol aralkyl resin include a resin obtained by allowing a bishalogenomethyl compound represented by $Ar^2$—$(CH_2Y)_2$ to react with a naphthol compound with an acidic catalyst or with no catalysts according to a known method, and a resin obtained by allowing a bis(alkoxymethyl) compound represented by $Ar^2$—$(CH_2OR)_2$ or a bis(hydroxymethyl) compound represented by $Ar^2$—$(CH_2OH)_2$ to react with a naphthol compound in the presence of an acidic catalyst. Herein, Y represents a halogen atom. In addition, R represents an alkyl group. $Ar^2$ represents the same groups as those described in the formula (2).

((1b) Phenolic Resin Having Adamantane Structure)

The phenolic resin having an adamantane structure is not particularly limited, as long as it has a structure in which an aromatic ring having a hydroxy group is bonded to an adamantyl group. An example of such a phenolic resin having an adamantane structure is a compound wherein, in the above general formula (1), X is the group represented by the above general formula (2i). Specifically, it is a compound represented by the following general formula (20). A hardened product of a cyanate ester obtained from such a compound tends to have a low coefficient of thermal expansion and also have excellent flame retardance and heat resistance.

[Formula 25]

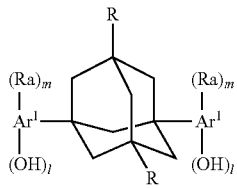

(20)

wherein $Ar^1$ each independently represent a phenylene group optionally having a substituent, a naphthylene group optionally having a substituent, or a biphenylene group optionally having a substituent; R is the same as R in the formula (2i); Ra is the same as Ra in the formula (1); l represents the number of hydroxy groups bonded to $Ar^1$, which is an integer of 1 to 3; and m represents the number of Ra bonded to $Ar^1$, wherein it is an integer of 5-1 when $Ar^1$ represents a phenylene group, it is an integer of 7-1 when $Ar^1$ represents a naphthylene group, and it is an integer of 9-1 when $Ar^1$ represents a biphenylene group.

Such a phenolic resin having an adamantane structure is not particularly limited, and examples thereof include 1,3-bis(4-hydroxyphenyl)adamantane, 1,3-bis(4-hydroxyphenyl)-5,7-dimethyladamantane, 1,3-bis(4-hydroxyphenyl)-5-methyladamantane, 1,3-bis(4-hydroxyphenyl)-5-ethyladamantane, 1,3-bis(4-hydroxyphenyl)-5-propyladamantane, 1,3-bis(4-hydroxyphenyl)-5-isopropyladamantane, 1,3-bis(4-hydroxyphenyl)-5-t-butyladamantane, 1,3-bis(4-hydroxyphenyl)-5,7-dimethyladamantane, 1,3-bis(4-hydroxyphenyl)-5-methyl-7-ethyladamantane, 1,3-bis(4-hydroxyphenyl)-5-methyl-7-propyladamantane, 1,3-bis(4-hydroxyphenyl)-5-ethyl-7-propyladamantane, 1,3-bis(4-hydroxyphenyl)-5,7-dipropyladamantane, 1,3-bis(4-hydroxyphenyl)-5-methyl-7-isopropyladamantane, 1,3-bis(4-hydroxyphenyl)-5-ethyl-7-isopropyladamantane, 1,3-bis(4-hydroxyphenyl)-5-propyl-7-isopropyladamantane, 1,3-bis(4-hydroxyphenyl)-5,7-diisopropyladamantane, 1,3-bis(4-hydroxyphenyl)-5-methyl-7-t-butyladamantane, 1,3-bis(4-hydroxyphenyl)-5-ethyl-7-t-butyladamantane, 1,3-bis(4-hydroxyphenyl)-5-propyl-7-t-butyladamantane, 1,3-bis(4-hydroxyphenyl)-5-isopropyl-7-t-butyladamantane, 1,3-bis(4-hydroxyphenyl)-5,7-di-t-butyladamantane, 1,3-bis(3-methyl-4-hydroxyphenyl)-5-methyladamantane, 1,3-bis(3-methyl-4-hydroxyphenyl)-5-ethyladamantane, 1,3-bis(3-methyl-4-hydroxyphenyl)-5-propyladamantane, 1,3-bis(3-methyl-4-hydroxyphenyl)-5-isopropyladamantane, 1,3-bis(3-methyl-4-hydroxyphenyl)-5-t-butyladamantane, 1,3-bis(3-methyl-4-hydroxyphenyl)-5,7-dimethyladamantane, 1,3-bis(3-methyl-4-hydroxyphenyl)-5-methyl-7-ethyladamantane, 1,3-bis(3-methyl-4-hydroxyphenyl)-5,7-diethyladamantane, 1,3-bis(3-methyl-4-hydroxyphenyl)-5-methyl-7-propyladamantane, 1,3-bis(3-methyl-4-hydroxyphenyl)-5-ethyl-7-propyladamantane, 1,3-bis(3-methyl-4-hydroxyphenyl)-5,7-dipropyladamantane, 1,3-bis(3-methyl-4-hydroxyphenyl)-5-methyl-7-isopropyladamantane, 1,3-bis(3-methyl-4-hydroxyphenyl)-5-ethyl-7-isopropyladamantane, 1,3-bis(3-methyl-4-hydroxyphenyl)-5-propyl-7-isopropyladamantane, 1,3-bis(3-methyl-4-hydroxyphenyl)-5,7-diisopropyladamantane, 1,3-bis(3-methyl-4-hydroxyphenyl)-5-methyl-7-t-butyladamantane, 1,3-bis(3-methyl-4-hydroxyphenyl)-5-ethyl-7-t-butyladamantane, 1,3-bis(3-methyl-4-hydroxyphenyl)-5-propyl-7-t-butyladamantane, 1,3-bis(3-methyl-4-hydroxyphenyl)-5-isopropyl-7-t-butyladamantane, 1,3-bis(3-methyl-4-hydroxyphenyl)-5,7-di-t-butyladamantane, 1,3-bis(3,5-dimethyl-4-hydroxyphenyl)-5-methyladamantane, 1,3-bis(3,5-dimethyl-4-hydroxyphenyl)-5-ethyladamantane, 1,3-bis(3,5-dimethyl-4-hydroxyphenyl)-5-propyladamantane, 1,3-bis(3,5-dimethyl-4-hydroxyphenyl)-5-isopropyladamantane, 1,3-bis(3,5-dimethyl-4-hydroxyphenyl)-5-t-butyladamantane, 1,3-bis(3,5-dimethyl-4-hydroxyphenyl)-5,7-dimethyladamantane, 1,3-bis(3,5-dimethyl-4-hydroxyphenyl)-5-methyl-7-ethyladamantane, 1,3-bis(3,5-dimethyl-4-hydroxyphenyl)-5,7-diethyladamantane, 1,3-bis(3,5-dimethyl-4-hydroxyphenyl)-5-methyl-7-propyladamantane, 1,3-bis(3,5-dimethyl-4-hydroxyphenyl)-5-ethyl-7-propyladamantane, 1,3-bis(3,5-dimethyl-4-hydroxyphenyl)-5,7-dipropyladamantane, 1,3-bis(3,5-dimethyl-4-hydroxyphenyl)-5-methyl-7-isopropyladamantane, 1,3-bis(3,5-dimethyl-4-hydroxyphenyl)-5-ethyl-7-isopropyladamantane, 1,3-bis(3,5-dimethyl-4-hydroxyphenyl)-5-propyl-7-isopropyladamantane, 1,3-bis(3,5-dimethyl-4-hydroxyphenyl)-5,7-diisopropyladamantane, 1,3-bis(3,5-dimethyl-4-hydroxyphenyl)-5-methyl-7-t-butyladamantane, 1,3-bis(3,5-dimethyl-4-hydroxyphenyl)-5-ethyl-7-t-butyladamantane, 1,3-bis(3,5-dimethyl-4-hydroxyphenyl)-5-propyl-7-t-butyladamantane, 1,3-bis(3,5-dimethyl-4-hydroxyphenyl)-5-isopropyl-7-t-butyladamantane, 1,3-bis(3,5-dimethyl-4-hydroxyphenyl)-5,7-di-t-butyladamantane, 1,3-bis(3-phenyl-4-hydroxyphenyl)-5-methyladamantane, 1,3-bis(3-phenyl-4-hydroxyphenyl)-5-ethyladamantane, 1,3-bis(3-phenyl-4-hydroxyphenyl)-5-propyladamantane, 1,3-bis(3-phenyl-4-hydroxyphenyl)-5-isopropyladamantane, 1,3-bis(3-phenyl-4-hydroxyphenyl)-5-t-butyladamantane, 1,3-bis(3-phenyl-4-hydroxyphenyl)-5,7-dimethyladamantane, 1,3-bis(3-phenyl-4-hydroxyphenyl)-5-methyl-7-ethyladamantane, 1,3-bis(3-phenyl-4-hydroxyphenyl)-5,7-diethyladamantane, 1,3-bis(3-phenyl-4-hydroxyphenyl)-5-methyl-7-propyladamantane, 1,3-bis(3-phenyl-4-hydroxyphenyl)-5-ethyl-7-propyladamantane, 1,3-bis(3-phenyl-4-hydroxyphenyl)-5,7-dipropyladamantane, 1,3-bis(3-phenyl-4-hydroxyphenyl)-5-methyl-7-isopropyladamantane, 1,3-bis(3-phenyl-4-hydroxyphenyl)-5-ethyl-7-isopropyladamantane, 1,3-bis(3-phenyl-4-hydroxyphenyl)-5-propyl-7-isopropyladamantane, 1,3-bis(3-phenyl-4-hydroxyphenyl)-5,7-diisopropyladamantane, 1,3-bis(3-phenyl-4-hydroxyphenyl)-5-methyl-7-t-butyladamantane, 1,3-bis(3-phenyl-4-hydroxyphenyl)-5-ethyl-7-t-butyladamantane, 1,3-bis(3-phenyl-4-hydroxyphenyl)-5-propyl-7-t-butyladamantane, 1,3-bis(3-phenyl-4-hydroxyphenyl)-5-isopropyl-7-t-butyladamantane, 1,3-bis(3-phenyl-4-hydroxyphenyl)-5,7-di-t-butyladamantane, 1,3-bis(3-cyclohexyl-4-hydroxyphenyl)-5-methyladamantane, 1,3-bis(3-cyclohexyl-4-hydroxyphenyl)-5-ethyladamantane, 1,3-bis(3-cyclohexyl-4-hydroxyphenyl)-5-propyladamantane, 1,3-bis(3-cyclohexyl-4-hydroxyphenyl)-5-isopropyladamantane, 1,3-bis(3-cyclohexyl-4-hydroxyphenyl)-5-t-butyladamantane, 1,3-bis(3-cyclohexyl-4-hydroxyphenyl)-5,7-dimethyladamantane, 1,3-bis(3-cyclohexyl-4-hydroxyphenyl)-5-methyl-7-ethyladamantane, 1,3-bis(3-cyclohexyl-4-hydroxyphenyl)-5,7-diethyladamantane, 1,3-bis(3-cyclohexyl-4-hydroxyphenyl)-5-methyl-7-propyladamantane, 1,3-bis(3-cyclohexyl-4-hydroxyphenyl)-5-ethyl-7-propyladamantane, 1,3-bis(3-cyclohexyl-4-hydroxyphenyl)-5,7-dipropyladamantane, 1,3-bis(3-cyclohexyl-4-hydroxyphenyl)-5-methyl-7-isopropyladamantane, 1,3-bis(3-cyclohexyl-4-hydroxyphenyl)-5-ethyl-7-isopropyladamantane, 1,3-bis(3-cyclohexyl-4-hydroxyphenyl)-5-propyl-7-isopropyladamantane, 1,3-bis(3- cyclohexyl-4-hydroxyphenyl)-5,7-diisopropyladamantane, 1,3-bis(3-cyclohexyl-4-hydroxyphenyl)-5-methyl-7-t-butyladamantane, 1,3-bis(3-cyclohexyl-4-hydroxyphenyl)-5-ethyl-7-t-butyladamantane, 1,3-bis(3-cyclohexyl-4-hydroxyphenyl)-5-propyl-7-t-butyladamantane, 1,3-bis(3-cyclohexyl-4-hydroxyphenyl)-5-isopropyl-7-t-butyladamantane, 1,3-bis(3-cyclohexyl-4-hydroxyphenyl)-5,7-di-t-butyladamantane, 1,3-bis(4-methyl-2-hydroxyphenyl)-5-methyladamantane, 1,3-bis(4-methyl-2-hydroxyphenyl)-5-ethyladamantane, 1,3-bis(4-methyl-2-hydroxyphenyl)-5-propyladamantane, 1,3-bis(4-methyl-2-hydroxyphenyl)-5-isopropyladamantane, 1,3-bis(4-methyl-2-hydroxyphenyl)-5-t-butyladamantane, 1,3-bis(4-methyl-2-hydroxyphenyl)-5,7-dimethyladamantane, 1,3-bis(4-methyl-2-hydroxyphenyl)-5-methyl-7-ethyladamantane, 1,3-bis(4-methyl-2-hydroxyphenyl)-5,7-diethyladamantane, 1,3-bis(4-methyl-2-hydroxyphenyl)-5-methyl-7-propyladamantane, 1,3-bis(4-methyl-2-hydroxyphenyl)-5-ethyl-7-propyladamantane, 1,3-bis(4-methyl-2-hydroxyphenyl)-5,7-dipropyladamantane, 1,3-bis(4-methyl-2-hydroxyphenyl)-5-methyl-7-isopropyladamantane, 1,3-bis(4-methyl-2-hydroxyphenyl)-5-ethyl-7-isopropyladamantane, 1,3-bis(4-methyl-2-hydroxyphenyl)-5-propyl-7-isopropyladamantane, 1,3-bis(4-methyl-2-hydroxyphenyl)-5,7-diisopropyladamantane, 1,3-bis(4-methyl-2-hydroxyphenyl)-5-methyl-7-t-butyladamantane, 1,3-bis(4-methyl-2-hydroxyphenyl)-5-ethyl-7-t-butyladamantane, 1,3-bis(4-methyl-2-hydroxyphenyl)-5-propyl-7-t-butyladamantane, 1,3-bis(4-methyl-2-hydroxyphenyl)-5-isopropyl-7-t-butyladamantane, 1,3-bis(4-methyl-2-hydroxyphenyl)-5,7-di-t-butyladamantane, and 1,3-bis(2,4-dihydroxyphenyl)-adamantane.

((1c) Other Hydroxy-Substituted Aromatic Compounds)

Among the compounds represented by the above general formula (1), other hydroxy-substituted aromatic compounds, other than the above described naphthol aralkyl resin and the above described phenolic resin having an adamantane structure, are not particularly limited, and examples thereof include phenol, o-, m- or p-cresol, o-, m- or p-methoxyphenol, 2,3-, 2,4-, 2,5-, 2,6-, 3,4- or 3,5-xylenol, ethylphenol, butylphenol, octylphenol, nonylphenol, 4-α-cumylphenol, 4-cyclohexylphenol, 4-vinylphenol, 2- or 3-chlorophenol, 2,6-dichlorophenol, 2-methyl-3-chlorophenol, nitrophenol, 4-nitro-2-ethylphenol, 2-methoxy-4-allylphenol, 4-methyl mercaptophenol, 3-trifluoromethylphenol, 4-hydroxybiphenyl, o- or p-acetylphenol, 4-hydroxybenzaldehyde, 4-hydroxybenzoic acid methyl ester, 4-hydroxybenzoic acid phenyl ester, 4-acetaminophenol, 4-hydroxybenzophenone, 2,6-di-tert-butylphenol, catechol, resorcinol, hydroquinone, 2-tert-butylhydroquinone, 2,4-dimethylhydroquinone, tetramethylhydroquinone, 2,4,6-trimethylresorcinol, 3,5-dihydroxytoluene, 1- or 2-naphthol, 4-methoxy-1-naphthol, 6-methyl-2-naphthol, 7-methoxy-2-naphthol, 2,2'-dihydroxy-1,1'-binaphthyl, 1,3-, 1,4-, 1,5-, 1,6-, 1,7-, 2,3-, 2,6- or 2,7-dihydroxynaphthalene, 2,2'- or 4,4'-dihydroxybiphenyl, 4,4'-dihydroxyoctafluorobiphenyl, 2,4'- or 4,4'-dihydroxydiphenylmethane, bis(4-hydroxy-3,5-dimethylphenyl)methane, 1,1-bis(4-hydroxyphenyl) ethane, 1,1-bis(4-hydroxyphenyl)propane, 2,2-bis(4-hydroxyphenyl)propane, 2,2-bis(4-hydroxy-3-methylphenyl)propane, 2,2-bis(2-hydroxy-5-biphenylyl)propane, 2,2-bis(4-hydroxyphenyl)hexafluoropropane, 2,2-bis(4-hydroxy-3,5-dimethylphenyl)propane, 1,1-bis(4-hydroxyphenyl)butane, 1,1-bis(4-hydroxyphenyl)isobutane, 1,1-bis(4-hydroxyphenyl)pentane, 1,1-bis(4-hydroxyphenyl)-3-methylbutane, 1,1-bis(4-hydroxyphenyl)-2-methylbutane, 1,1-bis(4-hydroxyphenyl)-2,2-dimethylpropane, 2,2-bis(4-hydroxyphenyl)butane, 2,2-bis(4-hydroxyphenyl)pentane, 2,2-bis(4-hydroxyphenyl)hexane, 2,2-bis(4-hydroxyphenyl)-3-methylbutane, 2,2-bis(4-hydroxyphenyl)-4-methylpentane, 2,2-bis(4-hydroxyphenyl)-3-methylpentane, 2,2-bis(4-hydroxyphenyl)-3,3-dimethylbutane, 3,3-bis(4-hydroxyphenyl)hexane, 3,3-bis(4-hydroxyphenyl)heptane, 3,3-bis(4-hydroxyphenyl)octane, 3,3-bis(4-hydroxyphenyl)-2-methylpentane, 3,3-bis(4-hydroxyphenyl)-2-methylhexane, 3,3-bis(4-hydroxyphenyl)-2,2-dimethylpentane, 4,4-bis(4-hydroxyphenyl)-3-methylheptane, 3,3-bis(4-hydroxyphenyl)-2-methylheptane, 3,3-bis(4-hydroxyphenyl)-2,2-dimethylhexane, 3,3-bis(4-hydroxyphenyl)-2,4-dimethylhexane, 3,3-bis(4-hydroxyphenyl)-2,2,4-trimethylpentane, 2,2-bis(4-hydroxyphenyl)-1,1,1,3,3,3-hexafluoropropane, bis(4-hydroxyphenyl)phenylmethane, 1,1-bis(4-hydroxyphenyl)-1-phenyl ethane, bis(4-hydroxyphenyl)biphenylmethane, 1,1-bis(4-hydroxyphenyl)cyclopentane, 1,1-bis(4-hydroxyphenyl)cyclohexane, 2,2-bis(4-hydroxy-3-isopropylphenyl)propane, 1,1-bis(3-cyclohexyl-4-hydroxyphenyl)cyclohexane, bis(4-hydroxyphenyl)diphenylmethane, bis(4-hydroxyphenyl)-2,2-dichloroethylene, 1,3-bis[2-(4-hydroxyphenyl)-2-propyl]benzene, 1,4-bis[2-(4-hydroxyphenyl)-2-propyl]benzene, 1,1-bis(4-hydroxyphenyl)-3,3,5-trimethylcyclohexane, 4-[bis(4-hydroxyphenyl)methyl]biphenyl, 4,4-dihydroxybenzophenone, 1,3-bis(4-hydroxyphenyl)-2-propene-1-one, bis(4-hydroxyphenyl)ether, bis(4-hydroxyphenyl)sulfide, bis(4-hydroxyphenyl)sulfone, 4-hydroxybenzoic acid 4-hydroxyphenyl ester (4-hydroxyphenyl 4-hydroxybenzoate), bis-(4-hydroxyphenyl)carbonate, phenolphthalein, o-cresolphthalein, 9,9'-bis(4-hydroxyphenyl)fluorene, 9,9-bis(4-hydroxy-3-methylphenyl)fluorene, 9,9-bis(2-hydroxy-5-biphenylyl)fluorene, tris(4-hydroxyphenyl)methane, 1,1,1-tris(4-hydroxyphenyl)ethane, 1,1,3-tris(4-hydroxyphenyl)propane, α,α,α'-tris(4-hydroxyphenyl)-1-ethyl-4-isopropylbenzene, 1,1,2,2-tetrakis(4-hydroxyphenyl)ethane, 4,4',4",4"'-methanetetrayltetrakisphenol, 2,4,6-tris(N-methyl-4-hydroxyanilino)-1,3,5-triazine, 2,4-bis(N-methyl-4-hydroxyanilino)-6-(N-methylanilino)-1,3,5-triazine, bis(N-4-hydroxy-2-methylphenyl)-4,4'-oxydiphthalimide, bis(N-3-hydroxy-4-methylphenyl)-4,4'-oxydiphthalimide, bis(N-4-hydroxyphenyl)-4,4'-oxydiphthalimide, bis(N-4-hydroxy-2-methylphenyl)-4,4'-(hexafluoroisopropylidene)diphthalimide, tris(3,5-dimethyl-4-hydroxybenzyl)isocyanurate, 2-phenyl-3,3-bis(4-hydroxyphenyl)phthalimidine, 2-(4-methylphenyl)-3,3-bis(4-hydroxyphenyl)phthalimidine, 2-phenyl-3,3-bis(4-hydroxy-3-methylphenyl)phthalimidine, 1-methyl-3,3-bis(4-hydroxyphenyl)indolin-2-one, 2-phenyl-3,3-bis(4-hydroxyphenyl)indolin-2-one, a phenol novolac resin, a cresol novolac resin, a phenol aralkyl resin, a cresol aralkyl resin, a biphenyl aralkyl resin, a phenol-modified xylene formaldehyde resin, and a phenol-modified dicyclopentadiene resin.

The phenol novolac resin and the cresol novolac resin are not particularly limited. Examples of these resins include resins obtained by allowing phenol, alkyl-substituted phenol or halogen-substituted phenol to react with formaldehyde compounds such as formalin or paraformaldehyde in an acidic solution according to a known method.

The phenol aralkyl resin, the cresol aralkyl resin, and the biphenyl aralkyl resin are not particularly limited. Examples of these resins include a resin obtained by allowing a bishalogenomethyl compound represented by $Ar^2$—$(CH_2Y)_2$ to react with a phenol compound with an acidic catalyst or with no catalysts according to a known method, and a resin obtained by allowing a bis(alkoxymethyl) compound represented by $Ar^2$—$(CH_2OR)_2$ or a bis(hydroxymethyl) compound represented by $Ar^2$—$(CH_2OH)_2$ to react with a phenol compound in the presence of an acidic catalyst. Herein, Y represents a halogen atom. In addition, R represents an alkyl group. $Ar^2$ represents the same groups as those described in the formula (2).

The phenol-modified xylene formaldehyde resin is not particularly limited, and an example of this resin is a resin obtained by allowing a xylene formaldehyde resin to react with a phenol compound in the presence of an acidic catalyst according to a known method.
(Basic Compound)

The basic compound that can be used in the method for producing a cyanate ester compound of the present embodiment may be either an organic base or an inorganic base. Thus, the type of the basic compound is not particularly limited. In addition, the basic compound may be used either in a solid state or in a solution state.

The organic base is not particularly limited. Preferred examples of the organic base include tertiary amines such as trimethylamine, triethylamine, tri-n-butylamine, triamylamine, diisopropylethylamine, diethyl-n-butylamine, methyldin-butylamine, methylethyl-n-butylamine, dodecyldimethylamine, tribenzylamine, triethanolamine, N,N-dimethylaniline, N,N-diethylaniline, diphenylmethylamine, pyridine, diethylcyclohexylamine, tricyclohexylamine, 1,4-diazabicyclo[2.2.2]octane, 1,8-diazabicyclo[5.4.0]-7-undecene, and 1,5-diazabicyclo[4.3.0]-5-nonene. From the viewpoint of the yield of a product of interest, among these, trimethylamine, triethylamine, tri-n-butylamine, and diisopropylethylamine are more preferable, and triethylamine is even more preferable.

The amount of the organic base used in the cyanation step is not particularly limited. When the cyanogen halide solution g or h containing only an organic solvent is used, the organic base is used in an amount of preferably 0.1 to 8 moles, more preferably 1.0 to 5.0 moles, and even more preferably 1.0 to 3.0 moles, based on 1 mole of the hydroxy group of the hydroxy-substituted aromatic compound.

Moreover, when the cyanogen halide solution d, e, f, or i containing only water, or water and an organic solvent, the used amount of the organic base is not particularly limited. The organic base is used in an amount of preferably 1.0 to 10 moles, more preferably 1.0 to 3.5 moles, and even more preferably 1.5 to 3.0 moles, based on 1 mole of the hydroxy group of the hydroxy-substituted aromatic compound. By setting the used amount of the organic base within the aforementioned range, the yield of a cyanate ester compound tends to be further improved with no remaining unreacted hydroxy-substituted aromatic compounds.

The inorganic base used in the cyanation step is not particularly limited. Preferred examples of the inorganic base include industrially generally used alkali metal hydroxides, such as sodium hydroxide, potassium hydroxide, and lithium hydroxide. Among these, from the viewpoint of inexpensive acquisition, sodium hydroxide is particularly preferable.

The amount of the inorganic base used in the cyanation step is not particularly limited. The inorganic base is used in an amount of preferably 1.0 to 8.0 moles, more preferably 1.0 to 5.0 moles, and even more preferably 1.0 to 3.5 moles, based on 1 mole of the hydroxy group of the hydroxy-substituted aromatic compound. By setting the used amount of the inorganic base within the aforementioned range, the yield of a cyanate ester compound tends to be further improved with no remaining unreacted hydroxy-substituted aromatic compounds.

In the cyanation step, the basic compound can be used in the form of a solution that is obtained by dissolving the basic compound in water or an organic solvent. In particular, when the basic compound is an organic base, an organic solvent is preferably used, whereas when the basic compound is an inorganic base, water is preferably used.

The content of a solvent in a basic compound solution is not particularly limited. When the basic compound solution comprises a hydroxy-substituted aromatic compound, the solvent is used in an amount of preferably 0.10 to 100 parts by mass, more preferably 0.10 to 80 parts by mass, and even more preferably 0.50 to 50 parts by mass, based on 1 part by mass of the hydroxy-substituted aromatic compound.

On the other hand, when the basic compound solution does not comprise a hydroxy-substituted aromatic compound, the content of a solvent in the basic compound solution is not particularly limited. The solvent is used in an amount of preferably 0.10 to 100 parts by mass, and more preferably 2.5 to 50 parts by mass, based on 1 part by mass of the basic compound.

The organic solvent that may be contained in the basic compound solution is not particularly limited. Examples of such an organic solvent include: ketone solvents such as acetone, methyl ethyl ketone, and methyl isobutyl ketone; aromatic solvents such as benzene, toluene, and xylene; ether solvents such as diethyl ether, dimethyl cellosolve, diglyme, tetrahydrofuran, methyl tetrahydrofuran, dioxane, and tetraethylene glycol dimethyl ether; halogenated hydrocarbon solvents such as dichloromethane, chloroform, carbon tetrachloride, dichloroethane, trichloroethane, chlorobenzene, and bromobenzene; alcohol solvents such as methanol, ethanol, isopropanol, methyl cellosolve, and propylene glycol monomethyl ether; aprotic polar solvents such as N,N-dimethylformamide, N-methylpyrrolidone, 1,3-dimethyl-2-imidazolidone, and dimethyl sulfoxide; nitrile solvents such as acetonitrile and benzonitrile; nitro solvents such as nitromethane and nitrobenzene; ester solvents such as ethyl acetate and ethyl benzoate; and hydrocarbon solvents such as cyclohexane. These organic solvents can be appropriately selected depending on the type of the basic compound, a reaction substrate, and a solvent used in the reaction. These solvents may be used singly or in combination of two or more types.

When the cyanogen halide solutions e, f and i are used, an organic solvent that is immiscible with water and is inactive in the reaction is preferably used in the basic compound solution. Such an organic solvent is not particularly limited. Examples of the organic solvent used herein include: halogenated hydrocarbon solvents such as dichloromethane, chloroform, carbon tetrachloride, dichloroethane, trichloroethane, chlorobenzene, and bromobenzene; aliphatic solvents such as n-hexane, cyclohexane, isooctane, cyclohexanone, cyclopentanone, and 2-butanone; aromatic solvents such as benzene, toluene, xylene, and ethyl benzene; ketone solvents such as methyl ethyl ketone and methyl isobutyl ketone; nitrile solvents such as benzonitrile; nitro solvents such as nitrobenzene; ether solvents such as diethyl ether, diisopropyl ether, and tetrahydrofuran; and ester solvents such as ethyl acetate and ethyl benzoate. Among these, halogenated hydrocarbon solvents containing 1 or 2 carbon atoms, such as dichloromethane, chloroform, carbon tetrachloride, dichloroethane, and trichloroethane, are more preferable. Using an organic solvent that is immiscible with water, only an organic solvent phase comprising a cyanate ester compound can be fractionated from a reaction solution that is a mixed system of the organic solvent and water at the terminal point of the cyanation step, and thus, separation of the cyanate ester compound becomes easier.

The water that may be comprised in the basic compound solution is not particularly limited. Examples of the water include tap water, distilled water, and deionized water. Among these, distilled water or deionized water having a few impurities is preferable from the viewpoint of efficiently obtaining a cyanate ester compound of interest.

When the solvent used in the basic compound solution is water, the basic compound solution preferably comprises a catalytic amount of organic base as a surfactant. By allowing the basic compound solution to comprise a surfactant, a predetermined reaction rate tends to be ensured. The surfactant is not particularly limited, and tertiary amines having a few side effects, such as alkylamine, arylamine, and cycloalkylamine, are preferable. Specific examples of such a tertiary amine include trimethylamine, triethylamine, tri-n-butylamine, triamyl amine, doisopropylethylamine, diethyl-n-butylamine, methyldi-n-butylamine, methylethyl-n-butylamine, dodecyldimethylamine, tribenzylamine, triethanolamine, N,N-dimethylaniline N,N-diethylaniline diphenylmethylamine, pyridine, diethylcyclohexylamine, tricyclohexylamine, 1,4-diazabicyclo[2.2.2]octane, 1,8-diazabicyclo[5.4.0]-7-undecene, and 1,5-diazabicyclo[4.3.0]-5-nonene. From the viewpoint of high solubility in water and obtaining a product of interest at a high yield, among these, trimethylamine, triethylamine, tri-n-butylamine, and diisopropylethylamine are more preferable, and triethylamine is even more preferable.

The total amount of a solvent used in the cyanation step is not particularly limited. The solvent is used in an amount of preferably 1.0 to 200 parts by mass, more preferably 1.5 to 150 parts by mass, and even more preferably 2.5 to 100 parts by mass, based on 1 part by mass of the hydroxy-substituted aromatic compound. By setting the total amount of the solvent used in the cyanation step within the aforementioned range, the hydroxy-substituted aromatic compound can be uniformly dissolved in the solvent, and the production efficiency of a cyanate ester compound tends to be further improved.

The pH of the reaction solution in the cyanation step is not particularly limited. It is preferably less than 7, more preferably 6.5 or less, and even more preferably 6 or less. By carrying out the reaction while keeping the pH of the reaction solution at less than 7, the generation of by-products such as imidocarbonate or a polymer of a cyanate ester compound is suppressed, and the production efficiency of a cyanate ester compound tends to be further improved. In order to keep the pH of the reaction solution at less than 7, a method of adding an acid is preferably applied. Specific examples of the method of adding an acid include a method of adding an acid to a cyanogen halide solution immediately before the cyanation step, and a method which comprises adding an acid to the reaction system during the reaction, while appropriately measuring the pH of the reaction solution with a pH meter, so as to keep the pH at less than 7. The acid used herein is not particularly limited, and examples of the acid include inorganic acids such as hydrochloric acid, nitric acid, sulfuric acid and phosphoric acid, and organic acids such as acetic acid, lactic acid, and propionic acid.

The reaction temperature applied in the cyanation step is not particularly limited. From the viewpoint of suppression of the generation of by-products such as imidocarbonate, a polymer of a cyanate ester compound, and dialkyl cyanamide, the condensation of the reaction solution, and the volatization of cyanogen chloride when the cyanogen chloride is used as a cyanogen halide, the reaction temperature is preferably −20° C. to +50° C., more preferably −15° C. to 15° C., and even more preferably −10° C. to 10° C.

The reaction pressure applied in the cyanation step is not particularly limited. It may be an ordinary pressure, or a pressure higher than the ordinary pressure. In addition, inert gas such as nitrogen, helium, or argon may be supplied into the reaction system, as necessary.

In addition, the reaction time is not particularly limited. The dropping time in a case in which the contacting operation is carried out by the method (a) and the method (b), and the contacting time of the case of the method (c), are each preferably 1 minute to 20 hours, and more preferably 3 minutes to 10 hours. Thereafter, it is preferable to stir the reaction solution for 10 minutes to 10 hours, while the aforementioned reaction temperature is maintained. By setting the reaction time within the aforementioned range, a cyanate ester compound of interest tends to be obtained with higher economical and industrial efficiency.

The degree of reaction progress in the cyanation step can be analyzed by liquid chromatography, an IR spectrum method or the like. In addition, volatile components such as subgenerated dicyan or dialkyl cyanamide can be analyzed by gas chromatography. After completion of the reaction, an ordinary post-treatment operation, and as desired, a separation operation and/or a purification operation are carried out, so that a cyanate ester compound of interest can be isolated. Specifically, an organic solvent phase containing a cyanate ester compound is fractionated from the reaction solution, and thereafter, the organic solvent phase is washed and concentrated, so that the cyanate ester compound can be precipitated or crystallized. Otherwise, after the organic solvent phase has been washed with water, the solvent in the organic solvent phase is replaced with a solvent, in which the cyanate compound is insoluble or poorly soluble, so that the cyanate ester compound can be precipitated or crystallized. During the washing operation, in order to remove excessive amines, an aqueous solution of acidic such as diluted hydrochloric acid may be used. Moreover, in order to remove water content from the fully washed organic solvent phase, a drying operation may be carried out according to a common method using sodium sulfate or magnesium sulfate.

During the concentration and the solvent replacement, in order to suppress the polymerization of a cyanate ester compound, it is preferable to heat the reaction solution to a temperature of 90° C. or lower under reduced pressure, so as to distill away the organic solvent. Further, upon the precipitation and the crystallization, a solvent, in which the cyanate ester compound is poorly dissolved, can be added dropwise to a solution containing the cyanate ester compound, or a solution containing the cyanate ester compound can be added dropwise to such a solvent, in which the cyanate ester compound is poorly dissolved. The solvent, in which the cyanate ester compound is poorly dissolved, is not particularly limited. Examples of such a solvent include; ether solvents; hydrocarbon solvents such as hexane; and alcohol solvents.

In order to wash the obtained crude product, a concentrate of the reaction solution, or a crystal obtained by precipitation or crystallization of the concentrate, may be washed with a solvent, in which the cyanate ester compound is poorly dissolved. In addition, it may also be possible to solubilize again a crystal obtained by concentration of the reaction solution, and then to recrystallized it. Moreover, in the case of crystallization, the reaction solution may be simply concentrated or cooled.

The purity of the obtained cyanate ester compound can be analyzed by liquid chromatography, an IR spectrum method or the like. Volatile components including subgenerated products contained in the cyanate ester compound, such as dialkyl cyanamide, or remaining solvents, can be subjected to quantitative analysis by gas chromatography. Halogen compounds remaining in the cyanate ester compound can be identified with a liquid chromatography mass spectrometer. In addition, they can be subjected to quantitative analysis by potentiometric titration using a silver nitrate solution or ion chromatography after such compounds have been decomposed by a combustion method. The polymerization reactivity of the cyanate ester compound can be evaluated based on a gelatinization time by a hot plate method or a torque measurement method.

Conventionally, the methods of cyanating a hydroxy-substituted aromatic compound have been widely known, and the cyanation method of the present embodiment can be carried out, as appropriate, with reference to such methods. Specifically, the following methods can be applied: a method of allowing a hydroxy-substituted aromatic compound to react with a cyanogen halide in a state in which the cyanogen halide is always present in an amount much larger than a base (U.S. Pat. No. 3,553,244); a method which comprises adding a tertiary amine used as a base, which is in an amount much larger than a cyanogen halide, dropwise to a hydroxy-substituted aromatic compound in the presence of a solvent, and then adding a cyanogen halide and a tertiary amine dropwise to the reaction solution (Japanese Patent No. 3319061); a method of reacting a hydroxy-substituted aromatic compound, a trialkylamine and a cyanogen halide in a continuous plug flow system (Japanese Patent No. 3905559); a method of treating, with cation and anion exchangers, tert-ammonium halide subgenerated when a hydroxy-substituted aromatic compound is allowed to react with a cyanogen halide in the presence of tert-amine in a non-aqueous solution (Japanese Patent No. 4055210); a method which comprises simultaneously adding a tertiary amine and a cyanogen halide to a hydroxy-substituted aromatic compound in the presence of a solvent separable from water, then reacting them, then washing the reaction solution with water, followed by liquid separation, and then subjecting the obtained solution to precipitation and purification using a poor solvent such as a secondary or tertiary alcohol or hydrocarbon (Japanese Patent No. 2991054); and further, a method of reacting a hydroxy-substituted aromatic compound, a cyanogen halide and a tertiary amine in a two-phase solvent of water and an organic solvent under acidic conditions (Japanese Patent No. 5026727).

[Cyanate Ester Compound]

The cyanate ester compound of the present embodiment is obtained by cyanation of a hydroxy-substituted aromatic compound using the cyanogen halide produced by the above described method for producing a cyanogen halide. Thus, by using a cyanate ester compound produced with a cyanogen halide obtained by the above described method for producing a cyanogen halide and a predetermined hydroxy-substituted aromatic compound, a hardened product having a low coefficiency of thermal expansion and also having high flame retardance, low water-absorbing property, heat resistance upon moisture absorption, and heat resistance can be obtained.

The hydroxy-substituted aromatic compound is not particularly limited, and for example, those as listed above can be used. Examples of the cyanate ester compound obtained using these hydroxy-substituted aromatic compounds include a cyanate ester compound having a polynaphthylene ether structure and a cyanate ester compound represented by the following general formula (9). Herein, examples of the cyanate ester compound represented by the following general formula (9) include (9a) a naphthol aralkyl-based cyanate ester, (9b) an adamantane-based cyanate ester compound, and (9c) cyanate ester compound other than the compounds (9a) and (9b) (hereinafter also referred to as "other cyanate ester compounds"). Hereinafter, individual cyanate ester compounds will be described.

(Cyanate Ester Compound Having Polynaphthylene Ether Structure)

First, the cyanate ester compound having a polynaphthylene ether structure will be described. A hardened product produced using a cyanate ester compound having such a structure tends to be more excellent in terms of flame retardance, low water-absorbing property, heat resistance upon moisture absorption, heat resistance, low thermal expansion, low dielectric property, low dielectric loss tangent, and the like.

The polynaphthylene ether-based cyanate ester compound is not particularly limited, as long as it has a cyanate group and has a structure in which naphthalene rings are bonded to each other via an oxygen bond. An example of the polynaphthylene ether-based cyanate ester compound is a cyanate ester compound represented by the following general formula (11). The cyanate ester compound represented by the following general formula (11) preferably comprises one or more selected from the group consisting of cyanate ester compounds represented by the following general formulae (13), (14), (15), and (16). A naphthylene ether-based cyanate ester compound having such a structure has, in a molecular structure thereof, a naphthylene ether structure in which a naphthalene ring is bonded to another naphthalene ring via an oxygen atom. Accordingly, during combustion of a hardened product, char formation is promoted, and excellent flame retardance is provided, and also, high heat resistance can be obtained.

[Formula 26]

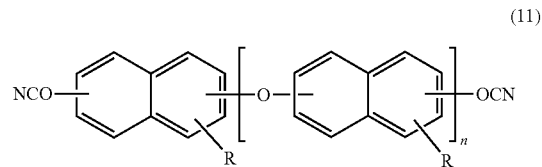

(11)

wherein n represents an integer of 1 to 20, and more preferably 1 to 10; and R each independently represent a hydrogen atom, a benzyl group, an alkyl group, or the following general formula (12),

[Formula 27]

(12)

wherein Ar each independently represent a phenylene group or a naphthylene group; and m represents an integer of 1 or 2.

[Formula 28]

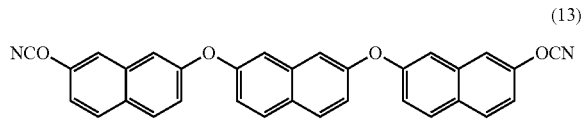
(13)

[Formula 29]

(14)

[Formula 30]

(15)

[Formula 31]

(16)

(Compound Represented by General Formula (9))

Next, a compound represented by the following general formula (9) will be described. A hardened product produced using a cyanate ester compound having such a structure tends to be more excellent in terms of flame retardance, low water-absorbing property, heat resistance upon moisture absorption, heat resistance, low thermal expansion, low dielectric property, low dielectric loss tangent, and the like.

[Formula 32]

$$H\text{—}\underset{(Ra)_m}{\overset{(OCN)_l}{Ar^1}}\text{—}(X\text{—}\underset{(Ra)_m}{\overset{(OCN)_l}{Ar^1}})_n\text{—}H \quad (9)$$

wherein $Ar^1$ each independently represent a phenylene group optionally having a substituent, a naphthylene group optionally having a substituent, or a biphenylene group optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of cyanate groups bonded to $Ar^1$, which is an integer of 1 to 3; m represents the number of Ra bonded to $Ar^1$, wherein it is 4-1 when $Ar^1$ represents a phenylene group, it is 6-1 when $Ar^1$ represents a naphthylene group, and it is 8-1 when $Ar^1$ represents a biphenylene group; n represents the average number of repetitions, which is an integer of 0 to 50; and X each independently represent a single bond, a divalent organic group containing 1 to 50 carbon atoms (wherein a hydrogen atom may be optionally replaced by a heteroatom), a divalent organic group containing 1 to 10 nitrogen atoms (—N—R—N—, etc.), a carbonyl group (—CO—), a carboxy group (—C(=O)O—), a carbonyl dioxide group (—OC(=O)O—), a sulfonyl group (—SO$_2$—), or either a divalent sulfur atom or a divalent oxygen atom.

In the above general formula (9), $Ar^1$ each independently represent a phenylene group optionally having a substituent, a naphthylene group optionally having a substituent, or a biphenylene group optionally having a substituent, in which the hydrogen element at any given position is replaced by an Ra group and a hydroxy group or a cyanate group.

In the above general formula (9), Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms.

The alkyl group containing 1 to 6 carbon atoms represented by Ra in the above general formula (9) optionally has a chain structure, a branched structure, or a cyclic structure. Such an alkyl group is not particularly limited. Examples of the alkyl group include a methyl group, an ethyl group, a propyl group, an isopropyl group, an n-butyl group, an isobutyl group, a tert-butyl group, an n-pentyl group, a 1-ethylpropyl group, a 2,2-dimethylpropyl group, a cyclopentyl group, a hexyl group, a cyclohexyl group, and a trifluoromethyl group. The hydrogen atom in the alkyl group in the above general formula (9) is optionally replaced by halogen atoms such as fluorine or chlorine, alkoxy groups such as a methoxy group or a phenoxy group, a cyano group, and the like.

The aryl group containing 6 to 12 carbon atoms represented by Ra in the above general formula (9) is not particularly limited. Examples of the aryl group include a phenyl group, a xylyl group, a mesityl group, a naphthyl group, a phenoxyphenyl group, an ethylphenyl group, an o-, m- or p-fluorophenyl group, a dichlorophenyl group, a dicyanophenyl group, a trifluoromethyl group, a methoxyphenyl group, and an o-, m- or p-tolyl group. The hydrogen atom in the aryl group in the above general formula (9) is optionally replaced by: halogen atoms such as fluorine or chlorine; alkoxy groups such as a methoxy group or a phenoxy group; a cyano group; a hydroxy group; and the like.

The alkoxy group containing 1 to 4 carbon atoms represented by Ra in the above general formula (9) optionally has a chain structure, a branched structure, or a cyclic structure. Such an alkoxy group is not particularly limited. Examples of the alkoxy group include a methoxy group, an ethoxy group, a propoxy group, an isopropoxy group, an n-butoxy group, an isobutoxy group, and a tert-butoxy group. The hydrogen atom in the alkoxy group in the above general formula (9) is optionally replaced by: halogen atoms such as fluorine or chlorine; alkoxy groups such as a methoxy group or a phenoxy group; a cyano group; and the like.

In the above general formula (9), X each independently represent a single bond, a divalent organic group containing 1 to 50 carbon atoms (wherein the hydrogen atom is optionally replaced by a heteroatom), a divalent organic group containing 1 to 10 nitrogen atoms, a carbonyl group (—CO—), a carboxy group (—C(=O)O—), a carbonyl dioxide group (—OC(=O)O—), a sulfonyl group (—SO$_2$—), or a divalent sulfur atom or a divalent oxygen atom.

The divalent organic group containing 1 to 50 carbon atoms represented by X in the above general formula (9) is not particularly limited. Examples of the divalent organic group containing 1 to 50 carbon atoms include a methylene group, an ethylene group, a trimethylene group, a propylene group, a cyclopentylene group, a cyclohexylene group, a trimethylcyclohexylene group, a biphenylmethylene group, a dimethylmethylene-phenylene-dimethylmethylene group, a fluorenediyl group, and a phthalide-diyl group. The hydrogen atom in the divalent organic group is optionally replaced by a heteroatom. The heteroatom is not particularly limited, and examples of the heteroatom include halogen atoms such as fluorine or chlorine. The hydrogen atom in the divalent organic group containing 1 to 50 carbon atoms is optionally replaced by alkoxy groups such as a methoxy group or a phenoxy group, a cyano group, and the like.

The divalent organic group containing 1 to 10 nitrogen atoms represented by X in the above general formula (9) is not particularly limited. Examples of the divalent organic group containing 1 to 10 nitrogen atoms include a group represented by —N—R—N—, an imino group, and a polyimino group.

Moreover, X in the above general formula (9) is preferably a divalent linking group selected from the group consisting of a divalent organic group containing 1 to 50 carbon atoms represented by the following general formula (10), and divalent groups represented by the following general formulae (2a), (2b), (2c), (2d), (2e), (2f), (2g), (2h), (2i) and (2j):

[Formula 33]

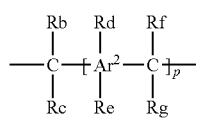
(10)

wherein Ar$^2$ each independently represent a phenylene group optionally having a substituent, a naphthylene group optionally having a substituent, or a biphenylene group optionally having a substituent; Rb, Rc, Rf, and Rg each independently represent a hydrogen atom, an alkyl group containing 1 to 6 carbon atoms and optionally having a substituent, or an aryl group containing 6 to 12 carbon atoms and optionally having a substituent; Rd and Re each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group; and p represents an integer of 0 to 5, and

[Formula 34]

(2a)

(2b)

(2c)

(2d)

(2e)

(2f)

(2g)

(2h)

(2i)

(2j)

wherein, in the formula (2d), z represents an integer of 4 to 7, and in the formula (2i), R each independently represent a hydrogen atom or an alkyl group containing 1 to 6 carbon atoms and optionally having a substituent.

Ar$^2$ in the above general formula (10) each independently represent a phenylene group, a naphthylene group, or a biphenylene group. The Ar$^2$ is not particularly limited, and examples thereof include a 1,4-phenylene group, a 1,3- phenylene group, a 2,6-naphthylene group, a 1,5-naphthylene group, a 1,6-naphthylene group, a 1,8-naphthylene group, a 1,3-naphthylene group, a 1,4-naphthylene group, a 4,4'-biphenylene group, a 2,4'-biphenylene group, a 2,2'-biphenylene group, a 2,3'-biphenylene group, a 3,3'-biphenylene group, and a 3,4'-biphenylene group.

Rb, Rc, Rf, and Rg in the above general formula (10) each independently represent a hydrogen atom, an alkyl group containing 1 to 6 carbon atoms and optionally having a substituent, and an aryl group containing 6 to 12 carbon atoms and optionally having a substituent. In addition, Rd and Re in the above general formula (10) each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group. The alkyl group containing 1 to 6 carbon atoms, aryl group containing 6 to 12 carbon atoms and optionally having a substituent, and alkoxy group containing 1 to 4 carbon atoms and optionally having a substituent, which are represented by Rb, Rc, Rd, Re, Rf, and Rg, are not particularly limited. Examples thereof include the same groups as those described for Ra in the above general formula (9).

((9a) Naphthol Aralkyl-Based Cyanate Ester Compound)

Next, a naphthol aralkyl-based cyanate ester compound will be described. The naphthol aralkyl-based cyanate ester compound is not particularly limited, as long as it has a structure in which a naphthalene ring having a cyanate group is bonded to a benzene ring via an alkyl group. For example, such a naphthol aralkyl resin is a compound wherein, in the above general formula (9), $Ar^1$ represents a naphthylene group, X is represented by the above general formula (2), and $Ar^2$ represents a phenylene group. Specifically, a cyanate ester compound represented by the following general formula (17) is preferable. In the cyanate ester compound represented by the following general formula (17), two methylene groups bonded to a benzene ring can be bonded thereto at an ortho position, a meta position, or a para position. Among these, the two methylene groups bonded to the benzene ring are preferably bonded to the meta position and/or para position of the benzene ring. A hardened product obtained from such a naphthol aralkyl-based cyanate ester compound tends to have a low coefficient of thermal expansion and be excellent in terms of combustion properties, low water-absorbing property, and heat resistance upon moisture absorption.

[Formula 35]

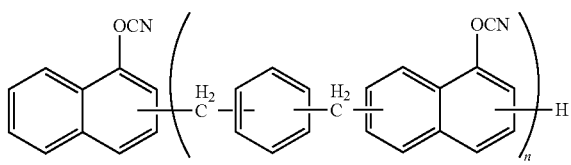

(17)

wherein n represents an integer of 1 to 50, and preferably 1 to 10.

((9b) Adamantane-Based Cyanate Ester Compound)

The adamantane-based cyanate ester compound is not particularly limited, as long as it has a structure in which an aromatic ring having a cyanate group is bonded to an adamantyl group. An example of such an adamantane-based cyanate ester compound is a compound wherein, in the above general formula (9), X is the group represented by the above general formula (2i). Specifically, it is a cyanate ester compound represented by the following general formula (18). A hardened product obtained from such an adamantane-based cyanate ester compound tends to have a low coefficient of thermal expansion and also have excellent flame retardance and heat resistance.

[Formula 36]

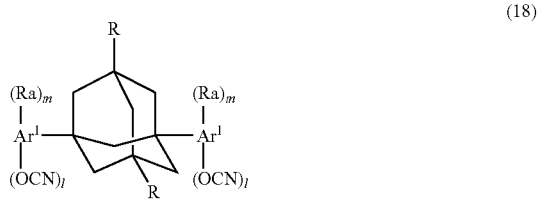

(18)

wherein $Ar^1$ each independently represent a phenylene group optionally having a substituent, a naphthylene group optionally having a substituent, or a biphenylene group optionally having a substituent; R is the same as R in the formula (2i); Ra is the same as Ra in the formula (9); l represents the number of hydroxy groups bonded to $Ar^1$, which is an integer of 1 to 3; and m represents the number of Ra bonded to $Ar^1$, wherein it is an integer of 5-l when $Ar^1$ represents a phenylene group, it is an integer of 7-l when $Ar^1$ represents a naphthylene group, and it is an integer of 9-l when $Ar^1$ represents a biphenylene group.

Such an adamantane-based cyanate ester compound is not particularly limited, and examples thereof include 1,3-bis(4-cyanatophenyl)adamantane, 1,3-bis(4-cyanatophenyl)-5,7-dimethyladamantane, 1,3-bis(4-cyanatophenyl)-5-methyladamantane, 1,3-bis(4-cyanatophenyl)-5-ethyladamantane, 1,3-bis(4-cyanatophenyl)-5-propyladamantane, 1,3-bis(4-cyanatophenyl)-5-isopropyladamantane, 1,3-bis(4-cyanatophenyl)-5-t-butyladamantane, 1,3-bis(4-cyanatophenyl)-5,7-dimethyladamantane, 1,3-bis(4-cyanatophenyl)-5-methyl-7-ethyladamantane, 1,3-bis(4-cyanatophenyl)-5-methyl-7-propyladamantane, 1,3-bis(4-cyanatophenyl)-5-ethyl-7-propyladamantane, 1,3-bis(4-cyanatophenyl)-5,7-dipropyladamantane, 1,3-bis(4-cyanatophenyl)-5-methyl-7-isopropyladamantane, 1,3-bis(4-cyanatophenyl)-5-ethyl-7-isopropyladamantane, 1,3-bis(4-cyanatophenyl)-5-propyl-7-isopropyladamantane, 1,3-bis(4-cyanatophenyl)-5,7-diisopropyladamantane, 1,3-bis(4-cyanatophenyl)-5-methyl-7-t-butyladamantane, 1,3-bis(4-cyanatophenyl)-5-ethyl-7-t-butyladamantane, 1,3-bis(4-cyanatophenyl)-5-propyl-7-t-butyladamantane, 1,3-bis(4-cyanatophenyl)-5-isopropyl-7-t-butyladamantane, 1,3-bis(4-cyanatophenyl)-5,7-di-t-butyladamantane, 1,3-bis(3-methyl-4-cyanatophenyl)-5-methyladamantane, 1,3-bis(3-methyl-4-cyanatophenyl)-5-ethyladamantane, 1,3-bis(3-methyl-4-cyanatophenyl)-5-propyladamantane, 1,3-bis(3-methyl-4-cyanatophenyl)-5-isopropyladamantane, 1,3-bis(3-methyl-4-cyanatophenyl)-5-t-butyladamantane, 1,3-bis(3-methyl-4-cyanatophenyl)-5,7-dimethyladamantane, 1,3-bis(3-methyl-4-cyanatophenyl)-5-methyl-7-ethyladamantane, 1,3-bis(3-methyl-4-cyanatophenyl)-5,7-diethyladamantane, 1,3-bis(3-methyl-4-cyanatophenyl)-5-methyl-7-propyladamantane, 1,3-bis(3-methyl-4-cyanatophenyl)-5-ethyl-7-propyladamantane, 1,3-bis(3-methyl-4-cyanatophenyl)-5,7-dipropyladamantane, 1,3-bis(3-methyl-4-cyanatophenyl)-5-methyl- 7-isopropyladamantane, 1,3-bis(3-methyl-4-cyanatophenyl)-5-ethyl-7-isopropyladamantane, 1,3-bis(3-methyl-4-cyanatophenyl)-5-propyl-7-isopropyladamantane, 1,3-bis(3-methyl-4-cyanatophenyl)-5,7-diisopropyladamantane, 1,3-bis(3-methyl-4-cyanatophenyl)-5-methyl-7-t-butyladamantane, 1,3-bis(3-methyl-4-cyanatophenyl)-5-ethyl-7-t-butyladamantane, 1,3-bis(3-methyl-4-cyanatophenyl)-5-propyl-7-t-butyladamantane, 1,3-bis(3-methyl-4-cyanatophenyl)-5-isopropyl-7-t-butyladamantane, 1,3-bis(3-methyl-4-cyanatophenyl)-5,7-di-t-butyladamantane, 1,3-bis(3,5-dimethyl-4-cyanatophenyl)-5-methyladamantane, 1,3-bis(3,5-dimethyl-4-cyanatophenyl)-5-ethyladamantane, 1,3-bis(3,5-dimethyl-4-cyanatophenyl)-5-propyladamantane, 1,3-bis(3,5-dimethyl-4-cyanatophenyl)-5-isopropyladamantane, 1,3-bis(3,5-dimethyl-4-cyanatophenyl)-5-t-butyladamantane, 1,3-bis(3,5-dimethyl-4-cyanatophenyl)-5,7-dimethyladamantane, 1,3-bis(3,5-dimethyl-4-cyanatophenyl)-5-methyl-7-ethyladamantane, 1,3-bis(3,5-dimethyl-4-cyanatophenyl)-5,7-diethyladamantane, 1,3-bis(3,5-dimethyl-4-cyanatophenyl)-5-methyl-7-propyladamantane, 1,3-bis(3,5-dimethyl-4-cyanatophenyl)-5-ethyl-7-propyladamantane, 1,3-bis(3,5-dimethyl-4-cyanatophenyl)-5,7-dipropyladamantane, 1,3-bis(3,5-dimethyl-4-cyanatophenyl)-5-methyl-7-isopropyladamantane, 1,3-bis(3,5-dimethyl-4-cyanatophenyl)-5-ethyl-7-isopropyladamantane, 1,3-bis(3,5-dimethyl-4-cyanatophenyl)-5-propyl-7-isopropyladamantane, 1,3-bis(3,5-dimethyl-4-cyanatophenyl)-5,7-diisopropyladamantane, 1,3-bis(3,5-dimethyl-4-cyanatophenyl)-5-methyl-7-t-butyladamantane, 1,3-bis(3,5-dimethyl-4-cyanatophenyl)-5-ethyl-7-t-butyladamantane, 1,3-bis(3,5-dimethyl-4-cyanatophenyl)-5-propyl-7-t-butyladamantane, 1,3-bis(3,5-dimethyl-4-cyanatophenyl)-5-isopropyl-7-t-butyladamantane, 1,3-bis(3,5-dimethyl-4-cyanatophenyl)-5,7-di-t-butyladamantane, 1,3-bis(3-phenyl-4-cyanatophenyl)-5-methyladamantane, 1,3-bis(3-phenyl-4-cyanatophenyl)-5-ethyladamantane, 1,3-bis(3-phenyl-4-cyanatophenyl)-5-propyladamantane, 1,3-bis(3-phenyl-4-cyanatophenyl)-5-isopropyladamantane, 1,3-bis(3-phenyl-4-cyanatophenyl)-5-t-butyladamantane, 1,3-bis(3-phenyl-4-cyanatophenyl)-5,7-dimethyladamantane, 1,3-bis(3-phenyl-4-cyanatophenyl)-5-methyl-7-ethyladamantane, 1,3-bis(3-phenyl-4-cyanatophenyl)-5,7-diethyladamantane, 1,3-bis(3-phenyl-4-cyanatophenyl)-5-methyl-7-propyladamantane, 1,3-bis(3-phenyl-4-cyanatophenyl)-5-ethyl-7-propyladamantane, 1,3-bis(3-phenyl-4-cyanatophenyl)-5,7-dipropyladamantane, 1,3-bis(3-phenyl-4-cyanatophenyl)-5-methyl-7-isopropyladamantane, 1,3-bis(3-phenyl-4-cyanatophenyl)-5-ethyl-7-isopropyladamantane, 1,3-bis(3-phenyl-4-cyanatophenyl)-5-propyl-7-isopropyladamantane, 1,3-bis(3-phenyl-4-cyanatophenyl)-5,7-diisopropyladamantane, 1,3-bis(3-phenyl-4-cyanatophenyl)-5-methyl-7-t-butyladamantane, 1,3-bis(3-phenyl-4-cyanatophenyl)-5-ethyl-7-t-butyladamantane, 1,3-bis(3-phenyl-4-cyanatophenyl)-5-propyl-7-t-butyladamantane, 1,3-bis(3-phenyl-4-cyanatophenyl)-5-isopropyl-7-t-butyladamantane, 1,3-bis(3-phenyl-4-cyanatophenyl)-5,7-di-t-butyladamantane, 1,3-bis(3-cyclohexyl-4-cyanatophenyl)-5-methyladamantane, 1,3-bis(3-cyclohexyl-4-cyanatophenyl)-5-ethyladamantane, 1,3-bis(3-cyclohexyl-4-cyanatophenyl)-5-propyladamantane, 1,3-bis(3-cyclohexyl-4-cyanatophenyl)-5-isopropyladamantane, 1,3-bis(3-cyclohexyl-4-cyanatophenyl)-5-t-butyladamantane, 1,3-bis(3-cyclohexyl-4-cyanatophenyl)-5,7-dimethyladamantane, 1,3-bis(3-cyclohexyl-4-cyanatophenyl)-5-methyl-7-ethyladamantane, 1,3-bis(3-cyclohexyl-4-cyanatophenyl)-5,7-diethyladamantane, 1,3-bis(3-cyclohexyl-4-cyanatophenyl)-5-methyl-7-propyladamantane, 1,3-bis(3-cyclohexyl-4-cyanatophenyl)-5-ethyl-7-propyladamantane, 1,3-bis(3-cyclohexyl-4-cyanatophenyl)-5,7-dipropyladamantane, 1,3-bis(3-cyclohexyl-4-cyanatophenyl)-5-methyl-7-isopropyladamantane, 1,3-bis(3-cyclohexyl-4-cyanatophenyl)-5-ethyl-7-isopropyladamantane, 1,3-bis(3-cyclohexyl-4-cyanatophenyl)-5-propyl-7-isopropyladamantane, 1,3-bis(3-cyclohexyl-4-cyanatophenyl)-5,7-diisopropyladamantane, 1,3-bis(3-cyclohexyl-4-cyanatophenyl)-5-methyl-7-t-butyladamantane, 1,3-bis(3-cyclohexyl-4-cyanatophenyl)-5-ethyl-7-t-butyladamantane, 1,3-bis(3-cyclohexyl-4-cyanatophenyl)-5-propyl-7-t-butyladamantane, 1,3-bis(3-cyclohexyl-4-cyanatophenyl)-5-isopropyl-7-t-butyladamantane, 1,3-bis(3-cyclohexyl-4-cyanatophenyl)-5,7-di-t-butyladamantane, 1,3-bis(4-methyl-2-cyanatophenyl)-5-methyladamantane, 1,3-bis(4-methyl-2-cyanatophenyl)-5-ethyladamantane, 1,3-bis(4-methyl-2-cyanatophenyl)-5-propyladamantane, 1,3-bis(4-methyl-2-cyanatophenyl)-5-isopropyladamantane, 1,3-bis(4-methyl-2-cyanatophenyl)-5-t-butyladamantane, 1,3-bis(4-methyl-2-cyanatophenyl)-5,7-dimethyladamantane, 1,3-bis(4-methyl-2-cyanatophenyl)-5-methyl-7-ethyladamantane, 1,3-bis(4-methyl-2-cyanatophenyl)-5,7-diethyladamantane, 1,3-bis(4-methyl-2-cyanatophenyl)-5-methyl-7-propyladamantane, 1,3-bis(4-methyl-2-cyanatophenyl)-5-ethyl-7-propyladamantane, 1,3-bis(4-methyl-2-cyanatophenyl)-5,7-dipropyladamantane, 1,3-bis(4-methyl-2-cyanatophenyl)-5-methyl-7-isopropyladamantane, 1,3-bis(4-methyl-2-cyanatophenyl)-5-ethyl-7-isopropyladamantane, 1,3-bis(4-methyl-2-cyanatophenyl)-5-propyl-7-isopropyladamantane, 1,3-bis(4-methyl-2-cyanatophenyl)-5,7-diisopropyladamantane, 1,3-bis(4-methyl-2-cyanatophenyl)-5-methyl-7-t-butyladamantane, 1,3-bis(4-methyl-2-cyanatophenyl)-5-ethyl-7-t-butyladamantane, 1,3-bis(4-methyl-2-cyanatophenyl)-5-propyl-7-t-butyladamantane, 1,3-bis(4-methyl-2-cyanatophenyl)-5-isopropyl-7-t-butyladamantane, 1,3-bis(4-methyl-2-cyanatophenyl)-5,7-di-t-butyladamantane, and 1,3-bis(2,4-dicyanatophenyl)-adamantane.

((9c) Other Cyanate Ester Compounds)

Among the compounds represented by the above general formula (9), other cyanate ester compounds, other than the above described naphthol aralkyl-based cyanate ester compound and the above described adamantane-based cyanate ester compound, are not particularly limited, and examples thereof include cyanatobenzene, 1-cyanato-2-, 1-cyanato-3-, or 1-cyanato-4-methylbenzene, 1-cyanato-2-,1-cyanato-3-, or 1-cyanato-4-methoxybenzene, 1-cyanato-2,3-, 1-cyanato-2,4-, 1-cyanato-2,5-, 1-cyanato-2,6-, 1-cyanato-3,4- or 1-cyanato-3,5-dimethylbenzene, cyanatoethylbenzene, cyanatobutylbenzene, cyanatooctylbenzene, cyanatononylbenzene, 2-(4-cyanatophenyl)-2-phenylpropane(4-α-cumylphenol cyanate), 1-cyanato-4-cyclohexylbenzene, 1-cyanato-4-vinylbenzene, 1-cyanato-2- or 1-cyanato-3-chlorobenzene, 1-cyanato-2,6-dichlorobenzene, 1-cyanato-2-methyl-3-chlorobenzene, cyanatonitrobenzene, 1-cyanato-4-nitro-2-ethylbenzene, 1-cyanato-2-methoxy-4-allylbenzene(eugenol cyanate), methyl(4-cyanatophenyl)sulfide, 1-cyanato-3-trifluoromethylbenzene, 4-cyanatobiphenyl, 1-cyanato-2- or 1-cyanato-4-acetylbenzene, 4-cyanatobenzaldehyde, 4-cyanatobenzoic acid methyl ester, 4-cyanatobenzoic acid phenyl ester, 1-cyanato-4-acetaminobenzene, 4-cyanatobenzophenone, 1-cyanato-2,6-di-tert-butylbenzene, 1,2-dicyanatobenzene, 1,3-dicyanatobenzene, 1,4-dicyanatobenzene, 1,4-dicyanato-2-tert-butylbenzene, 1,4-dicyanato-2,4-dimethylbenzene, 1,4-dicyanato-2,3,5,6- tetramethylbenzene, 1,3-dicyanato-2,4,6-trimethylbenzene, 1,3-dicyanato-5-methylbenzene, 1-cyanato or 2-cyanatonaphthalene, 1-cyanato 4-methoxynaphthalene, 2-cyanato-6-methylnaphthalene, 2-cyanato-7-methoxynaphthalene, 2,2'-dicyanato-1,1'-binaphthyl, 1,3-, 1,4-, 1,5-, 1,6-, 1,7-, 2,3-, 2,6- or 2,7-dicyanatonaphthalene, 2,2'- or 4,4'-dicyanatobiphenyl, 4,4'-dicyanatooctafluorobiphenyl, 2,4'- or 4,4'-dicyanatodiphenylmethane, bis(4-cyanato-3,5-dimethylphenyl)methane, 1,1-bis(4-cyanatophenyl)ethane, 1,1-bis(4-cyanatophenyl)propane, 2,2-bis(4-cyanatophenyl)propane, 2,2-bis(4-cyanato-3-methylphenyl)propane, 2,2-bis(2-cyanato-5-biphenylyl)propane, 2,2-bis(4-cyanatophenyl) hexafluoropropane, 2,2-bis(4-cyanato-3,5-dimethylphenyl) propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 2,2-bis(4-cyanatophenyl)butane, 2,2-bis(4-cyanatophenyl)pentane, 2,2-bis(4-cyanatophenyl) hexane, 2,2-bis(4-cyanatophenyl)-3-methylbutane, 2,2-bis(4-cyanatophenyl)-4-methylpentane, 2,2-bis(4-cyanatophenyl)-3-methylpentane, 2,2-bis(4-cyanatophenyl)-3,3-dimethylbutane, 3,3-bis(4-cyanatophenyl)hexane, 3,3-bis(4-cyanatophenyl)heptane, 3,3-bis(4-cyanatophenyl)octane, 3,3-bis(4-cyanatophenyl)-2-methylpentane, 3,3-bis(4-cyanatophenyl)-2-methylhexane, 3,3-bis(4-cyanatophenyl)-2,2-dimethylpentane, 4,4-bis(4-cyanatophenyl)-3-methylheptane, 3,3-bis(4-cyanatophenyl)-2-methylheptane, 3,3-bis(4-cyanatophenyl)-2,2-dimethylhexane, 3,3-bis(4-cyanatophenyl)-2,4-dimethylhexane, 3,3-bis(4-cyanatophenyl)-2,2,4-trimethylpentane, 2,2-bis(4-cyanatophenyl)-1,1,1,3,3,3-hexafluoropropane, bis(4-cyanatophenyl)phenylmethane, 1,1-bis(4-cyanatophenyl)-1-phenyl ethane, bis(4-cyanatophenyl)biphenylmethane, 1,1-bis(4-cyanatophenyl)cyclopentane, 1,1-bis(4-cyanatophenyl)cyclohexane, 2,2-bis(4-cyanato-3-isopropylphenyl)propane, 1,1-bis(3-cyclohexyl-4-cyanatophenyl)cyclohexane, bis(4-cyanatophenyl) diphenylmethane, bis(4-cyanatophenyl)-2,2-dichloroethylene, 1,3-bis[2-(4-cyanatophenyl)-2-propyl] benzene, 1,4-bis[2-(4-cyanatophenyl)-2-propyl]benzene, 1,1-bis(4-cyanatophenyl)-3,3,5-trimethyl cyclohexane, 4-[bis(4-cyanatophenyl)methyl]biphenyl, 4,4-dicyanatobenzophenone, 1,3-bis(4-cyanatophenyl)-2-propen-1-one, bis (4-cyanatophenyl)ether, bis(4-cyanatophenyl)sulfide, bis(4-cyanatophenyl)sulfone, 4-cyanatobenzoic acid-4-cyanatophenyl ester (4-cyanatophenyl-4-cyanatobenzoate), bis-(4-cyanatophenyl) carbonate, 3,3-bis(4-cyanatophenyl) isobenzofuran-1(3H)-one(phenolphthalein cyanate), 3,3-bis (4-cyanato-3-methylphenyl)isobenzofuran-1(3H)-one(o-cresolphthalein cyanate), 9,9'-bis(4-cyanatophenyl)fluorene, 9,9-bis(4-cyanato-3-methylphenyl)fluorene, 9,9-bis(2-cyanato-5-biphenylyl)fluorene, tris(4-cyanatophenyl)methane, 1,1,1-tris(4-cyanatophenyl)ethane, 1,1,3-tris(4-cyanatophenyl)propane, α,α,α'-tris(4-cyanatophenyl)-1-ethyl-4-isopropylbenzene, 1,1,2,2-tetrakis(4-cyanatophenyl)ethane, tetrakis(4-cyanatophenyl)methane, 2,4,6-tris(N-methyl-4-cyanatoanilino)-1,3,5-triazine, 2,4-bis(N-methyl-4-cyanatoanilino)-6-(N-methyl anilino)-1,3,5-triazine, bis(N-4-cyanato-2-methylphenyl)-4,4'-oxydiphthalimide, bis(N-3-cyanato-4-methylphenyl)-4,4'-oxydiphthalimide, bis(N-4-cyanatophenyl)-4,4'-oxydiphthalimide, bis(N-4-cyanato-2-methylphenyl)-4,4'-(hexafluoroisopropylidene) diphthalimide, tris(3,5-dimethyl-4-cyanatobenzyl) isocyanurate, 2-phenyl-3,3-bis(4-cyanatophenyl) phthalimidine, 2-(4-methylphenyl)-3,3-bis(4-cyanatophenyl)phthalimidine, 2-phenyl-3,3-bis(4-cyanato-3-methylphenyl)phthalimidine, 1-methyl-3,3-bis(4-cyanatophenyl)indolin-2-one, 2-phenyl-3,3-bis(4-cyanatophenyl)indolin-2-one, phenol novolac-based cyanate ester, cresol novolac-based cyanate ester, phenol aralkyl-based cyanate ester, cresol aralkyl-based cyanate ester, biphenyl aralkyl-based cyanate ester, phenol-modified xylene formaldehyde-based cyanate ester, and phenol-modified dicyclopentadiene-based cyanate ester, but examples thereof are not particularly limited thereto. These cyanate ester compounds can be used singly or in combination of two or more types.

[Resin Composition]

The resin composition of the present embodiment comprises, as an essential component, a predetermined cyanate ester compound obtained via the above-mentioned cyanogen halide-producing step and cyanation step. In addition, the resin composition of the present embodiment may further comprise, as necessary, one or more selected from the group consisting of a cyanate ester compound obtained without performing the above described two steps (hereinafter referred to as "another cyanate ester compound"), an epoxy resin, an oxetane resin, a maleimide compound, a phenolic resin, a benzoxazine compound, a compound having a polymerizable unsaturated group, and an inorganic filler. By allowing the resin composition of the present embodiment to have the above described configuration, a hardened product that is excellent in terms of flame retardance, low water-absorbing property, heat resistance upon moisture absorption, heat resistance, low thermal expansion, low dielectric property, low dielectric loss tangent and the like can be obtained.

(Cyanate Ester Compound)

The cyanate ester compound is not limited, as long as it comprises a cyanate ester compound obtained via the above-mentioned cyanogen halide-producing step and cyanation step. The cyanate ester compound may be used singly or in combination of two or more types.

The content of the cyanate ester compound is not particularly limited. It is preferably 1 to 100 parts by mass, more preferably 3 to 90 parts by mass, and even more preferably 5 to 80 parts by mass, based on 100 parts by mass of a resin solid in the resin composition. By setting the content of the cyanate ester compound within the aforementioned range, the resin composition tends to be more excellent in terms of heat resistance, low dielectric property, low dielectric loss tangent, and the like.

The term "resin solid content in the resin composition" is used herein to mean components except for a solvent and an inorganic filler in the resin composition, unless otherwise specified. In addition, the term "100 parts by mass of a resin solid content" is used to mean that a total of components except for a solvent and an inorganic filler in the resin composition is 100 parts by mass.

(Epoxy Resin)

By allowing the resin composition of the present embodiment to comprise an epoxy resin, the resin composition tends to be more excellent in terms of adhesiveness, heat resistance upon moisture absorption, flexibility, and the like. As an epoxy resin, a generally known epoxy resin can be used, as long as it is a compound having two or more epoxy groups in one molecule thereof, and thus, the type of the epoxy resin is not particularly limited. Specific examples thereof include a bisphenol A-based epoxy resin, a bisphenol E-based epoxy resin, a bisphenol F-based epoxy resin, a bisphenol S-based epoxy resin, a bisphenol A novolac-based epoxy resin, a biphenyl-based epoxy resin, a phenol novolac-based epoxy resin, a cresol novolac-based epoxy resin, a xylene novolac-based epoxy resin, a multifunctional phenol-based epoxy resin, a naphthalene-based epoxy resin, a naphthalene skeleton-modified novolac-based epoxy resin, a naphthylene ether-based epoxy resin, a phenol aralkyl-based epoxy resin, an anthracene-based epoxy resin, a trifunctional phenol-based epoxy resin, a tetrafunctional phenol-based epoxy resin, triglycidyl isocyanulate, a glycidyl ester-based epoxy resin, an alicyclic epoxy resin, a dicyclopentadiene novolac-based epoxy resin, a biphenyl novolac-based epoxy resin, a phenol aralkyl novolac-based epoxy resin, a naphthol aralkyl novolac-based epoxy resin, an aralkyl novolac-based epoxy resin, a biphenyl aralkyl-based epoxy resin, a naphthol aralkyl-based epoxy resin, a dicyclopentadiene-based epoxy resin, a polyol-based epoxy resin, a phosphorus-containing epoxy resin, a compound obtained by epoxidation of a double bond of glycidyl amine, butadiene or the like, a compound obtained by a reaction of a hydroxyl group-containing silicon resin with epichlorohydrin, and a halide thereof. These epoxy resins can be used singly or in combination of two or more types.

Among these, the epoxy resin is preferably one or more selected from the group consisting of a biphenyl aralkyl-based epoxy resin, a naphthylene ether-based epoxy resin, a multifunctional phenolic epoxy resin, and a naphthalene-based epoxy resin. By allowing the resin composition of the present embodiment to comprise such an epoxy resin, the flame retardance and heat resistance of the obtained hardened product tend to be further improved.

The content of the epoxy resin is not particularly limited. It is preferably 0 to 99 parts by mass, more preferably 1 to 90 parts by mass, and even more preferably 3 to 80 parts by mass, based on 100 parts by mass of a resin solid content in the resin composition. By setting the content of the epoxy resin within the aforementioned range, the resin composition tends to be more excellent in terms of adhesiveness, flexibility, and the like.

(Inorganic Filler)

By allowing the resin composition of the present embodiment to comprise an inorganic filler, the resin composition tends to be more excellent in terms of flame retardance, low thermal expansion, high thermal conductivity, toughness, and the like. As an inorganic filler, a generally known inorganic filler can be used, and the type of the inorganic filler is not particularly limited. Specific examples thereof include: silicates such as kaolin, fired kaolin, talc, fired talc, fired clay, unfired clay, mica, E-glass, A-glass, NE-glass, C-glass, L-glass, D-glass, S-glass, M-glass G20, short glass fibers (including fine glass powders of E-glass, T-glass, D-glass, S-glass, Q-glass, etc.), hollow glass, and sphere glass; silicas such as white carbon (wet silica), natural silica, molten silica, synthetic silica, amorphous silica, Aerosil, and hollow silica; oxides such as titanium oxide, alumina, boehmite, zinc oxide, magnesium oxide, and zirconium oxide; carbonates such as calcium carbonate, magnesium carbonate, and hydrotalcite; hydroxides such as aluminum hydroxide, a heat-treated product of aluminum hydroxide (which is produced by performing a heat treatment on aluminum hydroxide and then reducing a portion of crystalline water), magnesium hydroxide, and calcium hydroxide; sulfates or sulfites, such as barium sulfate, calcium sulfate, and calcium sulfite; borates such as zinc borate, barium metaborate, aluminum borate, calcium borate, and sodium borate; nitrides such as aluminum nitride, boron nitride, agglomerated boron nitride, silicon nitride, and carbon nitride; titanates such as strontium titanate and barium titanate; stannates such as zinc stannate; molybdenum compounds such as molybdenum oxide and zinc molybdate; and rubber fillers such as styrene-based, butadiene-based and acryl-based rubber powders, coreshell-based rubber powders, silicon composite powders, silicon resin powders, and silicon rubber powders. These inorganic fillers can be used singly or in combination of two or more types.

Herein, upon the use of an inorganic filler, it is preferable to use a silane coupling agent or a moisture dispersant in combination with the inorganic filler.

As a silane coupling agent, a silane coupling agent generally used for the surface treatment of inorganic matters can be preferably used. The type of the silane coupling agent is not particularly limited. Specific examples of the silane coupling agent include: aminosilane-based coupling agents such as γ-aminopropyltriethoxysilane and N-β-(aminoethyl)-γ-aminopropyltrimethoxysilane, epoxysilane-based coupling agents such as γ-glycidoxypropyltrimethoxysilane and β-(3,4-epoxycyclohexyl)ethyltrimethoxysilane, vinylsilane-based coupling agents such as γ-methacryloxypropyltrimethoxysilane and vinyl-tri(β-methoxyethoxy)silane, cationic silane coupling agents such as N-β-(N-vinylbenzylaminoethyl)-γ-aminopropyltrimethoxysilane hydrochloride, and phenylsilane-based coupling agents. These silane coupling agents can be used singly or in combination of two or more types.

In addition, as a moisture dispersant, a moisture dispersant generally used for coating can be preferably used. The type of the moisture dispersant is not particularly limited. Preferably, a copolymer-based moisture dispersant is used, and specific examples of such a moisture dispersant include Disperbyk-110, 111, 161 and 180, BYK-W996, BYK-W9010, BYK-W903, and BYK-W940, which are manufactured by BYK-Chemie Japan K.K. These moisture dispersants can be used singly or in combination of two or more types.

The content of the inorganic filler is not particularly limited. It is preferably 0 to 1600 parts by mass, more preferably 50 to 1600 parts by mass, even more preferably 75 to 1500 parts by mass, and further preferably 100 to 1400 parts by mass, based on 100 parts by mass of a resin solid content in the resin composition. By setting the content of the inorganic filler within the above described range, the resin composition tends to be more excellent in terms of flame retardance, low thermal expansion, and toughness.

(Oxetane Resin)

By allowing the resin composition of the present embodiment to comprise an oxetane resin, the resin composition tends to be more excellent in terms of adhesiveness, flexibility and the like. As an oxetane resin, a generally known oxetane resin can be used. The type of the oxetane resin is not particularly limited. Specific examples thereof include alkyloxetanes such as oxetane, 2-methyloxetane, 2,2-dimethyloxetane, 3-methyloxetane and 3,3-dimethyloxetane, 3-methyl-3-methoxymethyloxetane, 3,3'-di(trifluoromethyl)perfluoxetane, 2-chloromethyloxetane, 3,3-bis(chloromethyl)oxetane, biphenyl-based oxetane, OXT-101 (manufactured by TOAGOSEI Co., Ltd., trade name), and OXT-121 (manufactured by TOAGOSEI Co., Ltd., trade name). These oxetane resins can be used singly or in combination of two or more types.

The content of the oxetane resin is not particularly limited. It is preferably 0 to 99 parts by mass, more preferably 1 to 90 parts by mass, and even more preferably 3 to 80 parts by mass, based on the 100 parts by mass of a resin solid content in the resin composition. By setting the content of the oxetane resin within the aforementioned range, the resin composition tends to be more excellent in terms of adhesion, flexibility, and the like.

(Maleimide Compound)

By allowing the resin composition of the present embodiment to comprise a maleimide compound, the resin composition tends to be more excellent in terms of heat resistance, heat resistance upon moisture absorption, toughness, and the like. As a maleimide compound, a generally known maleimide compound can be used, as long as it is a compound having one or more maleimide groups in one molecule thereof. The type of the maleimide compound is not particularly limited. Specific examples of the maleimide compound include 4,4-diphenylmethane bismaleimide, phenylmethanemaleimide, m-phenylene bismaleimide, 2,2-bis(4-(4-maleimidephenoxy)-phenyl)propane, 3,3-dimethyl-5,5-diethyl-4,4-diphenylmethane bismaleimide, 4-methyl-1,3-phenylene bismaleimide, 1,6-bismaleimide-(2,2,4-trimethyl)hexane, 4,4-diphenylether bismaleimide, 4,4-diphenylsulfone bismaleimide, 1,3-bis(3-maleimidephenoxy)benzene, 1,3-bis(4-maleimidephenoxy)benzene, polyphenylmethane maleimide, and prepolymers of these maleimide compounds, or prepolymers of maleimide compounds and amine compounds, but examples thereof are not particularly limited thereto. These maleimide compounds can be used singly or in combination of two or more types.

The content of the maleimide compound is not particularly limited. It is preferably 0 to 99 parts by mass, more preferably 1 to 90 parts by mass, and even more preferably 3 to 80 parts by mass, based on 100 parts by mass of a resin solid content in the resin composition. By setting the content of the maleimide compound within the aforementioned range, the resin composition tends to be more excellent in terms of heat resistance and the like.

(Phenolic Resin)

By allowing the resin composition of the present embodiment to comprise a phenolic resin, the resin composition tends to be more excellent in terms of adhesiveness, flexibility, and the like. As a phenolic resin, a generally known phenolic resin can be used, as long as it has two or more hydroxyl groups in one molecule thereof. The type of the phenolic resin is not particularly limited. Specific examples of the phenolic resin include a bisphenol A-based phenolic resin, a bisphenol E-based phenolic resin, a bisphenol F-based phenolic resin, a bisphenol S-based phenolic resin, a phenol novolac resin, a bisphenol A novolac-based phenolic resin, a glycidyl ester-based phenolic resin, an aralkyl novolac-based phenolic resin, a biphenyl aralkyl-based phenol resin, a cresol novolac-based phenolic resin, a multifunctional phenolic resin, a naphthol resin, a naphthol novolac resin, a multifunctional naphthol resin, an anthracene-based phenolic resin, a naphthalene skeleton-modified novolac-based phenolic resin, a phenol aralkyl-based phenolic resin, a naphthol aralkyl-based phenolic resin, a dicyclopentadiene-based phenolic resin, a biphenyl-based phenolic resin, an alicyclic phenolic resin, a polyol-based phenolic resin, a phosphorus-containing phenolic resin, and a hydroxyl group-containing silicon resin, but examples thereof are not particularly limited thereto. These phenolic resins can be used singly or in combination of two or more types.

The content of the phenolic resin is not particularly limited. It is preferably 0 to 99 parts by mass, more preferably 1 to 90 parts by mass, and even more preferably 3 to 80 parts by mass, based on 100 parts by mass of a resin solid content in the resin composition. By setting the content of the phenolic resin within the aforementioned range, the resin composition tends to be more excellent in terms of adhesiveness, flexibility, and the like.

(Benzoxazine Compound)

By allowing the resin composition of the present embodiment to comprise a benzoxazine compound, the resin composition tends to be more excellent in terms of flame retardance, heat resistance, low water-absorbing property, low dielectric property, and the like. As a benzoxazine compound, a generally known benzoxazine compound can be used, as long as it is a compound having two or more dihydrobenzoxazine rings in one molecule thereof. The type of the benzoxazine compound is not particularly limited. Specific examples of the benzoxazine compound include bisphenol A-based benzoxazine BA-BXZ (manufactured by KONISHI CHEMICAL IND CO., LTD., trade name), bisphenol F-based benzoxazine BF-BXZ (manufactured by KONISHI CHEMICAL IND CO., LTD., trade name), and bisphenol S-based benzoxazine BS-BXZ (manufactured by KONISHI CHEMICAL IND CO., LTD., trade name). These benzoxazine compounds can be used singly or in combination of two or more types.

The content of the benzoxazine compound is not particularly limited. It is preferably 0 to 99 parts by mass, more preferably 1 to 90 parts by mass, and even more preferably 3 to 80 parts by mass, based on 100 parts by mass of a resin solid content in the resin composition. By setting the content of the benzoxazine compound within the aforementioned range, the resin composition tends to be more excellent in terms of heat resistance and the like.

(Compound Having Polymerizable Unsaturated Group)

By allowing the resin composition of the present embodiment to comprise a compound having a polymerizable unsaturated group, the resin composition tends to be more excellent in terms of heat resistance, toughness, and the like. As a compound having a polymerizable unsaturated group, a generally known compound having a polymerizable unsaturated group can be used. The type of the compound is not particularly limited. Specific examples of the compound having a polymerizable unsaturated group include: vinyl compounds such as ethylene, propylene, styrene, divinylbenzene, and divinylbiphenyl; (meth)acrylates of monohydric or polyhydric alcohols, such as methyl (meth)acrylate, 2-hydroxyethyl(meth)acrylate, 2-hydroxypropyl(meth)acrylate, polypropylene glycol di(meth)acrylate, trimethylolpropane di(meth)acrylate, trimethylolpropane tri(meth)acrylate, pentaerythritol tetra(meth)acrylate, and dipentaerythritol hexa(meth)acrylate; epoxy(meth)acrylates such as bisphenol A-based epoxy(meth)acrylate and bisphenol F-based epoxy(meth)acrylate; benzocyclobutene resin; and (bis)maleimide resin. These compounds each having an unsaturated group can be used singly or in combination of two or more types.

The content of the compound having a polymerizable unsaturated group is not particularly limited. It is preferably 0 to 99 parts by mass, more preferably 1 to 90 parts by mass, and even more preferably 3 to 80 parts by mass, based on 100 parts by mass of a resin solid content in the resin composition. By setting the content of the compound having a polymerizable unsaturated group within the aforementioned range, the resin composition tends to be more excellent in terms of heat resistance, toughness, and the like.

(Polymerization Catalyst and Hardening Accelerator)

The resin composition of the present embodiment may further comprise a polymerization catalyst that catalyzes the polymerization of a cyanate ester, an epoxy resin, an oxetane resin, or a compound having a polymerizable unsaturated group, and/or a hardening accelerator that appropriately adjusts a hardening rate, in addition to the above described compounds or resins. As such a polymerization catalyst and/or a hardening accelerator, a generally known polymerization catalyst and/or hardening accelerator can be used. The types of a polymerization catalyst and/or a hardening accelerator are not particularly limited. Specific examples thereof include: metal salts such as zinc octylate, zinc naphthenate, cobalt naphthenate, copper naphthenate, and iron(III) acetylacetonate; organic metal salts such as nickel octylate and manganese octylate; phenol compounds such as phenol, xylenol, cresol, resorcin, catechol, octylphenol, and nonylphenol; alcohols such as 1-butanol and 2-ethyl hexanol; imidazole derivatives such as 2-methylimidazole, 2-ethyl-4-methylimidazole, 2-phenylimidazole, 1-cyano-ethyl-2-phenylimidazole, 1-cyanoethyl-2-ethyl-4-methyl-imidazole, 2-phenyl-4,5-dihydroxymethylimidazole, and 2-phenyl-4-methyl-5-hydroxymethylimidazole; derivatives such as the carboxylates of these imidazoles, or the acid anhydride adducts thereof; amine compounds such as dicyan diamide, benzyldimethylamine, and 4-methyl-N,N-dimethylbenzylamine; phosphorus compounds such as phosphine compounds, phosphine oxide compounds, phosphonium compounds, and diphosphine compounds; peroxides such as epoxy-imidazole adduct compounds, benzoyl peroxide, p-chlorobenzoyl peroxide, di-t-butyl peroxide, diisopropyl peroxy carbonate, and di-2-ethylhexyl peroxy carbonate; and azo compounds such as azobisisobutyronitrile. As these catalysts, commercially available products may also be used. Examples of such a commercially available catalyst include Ajicure PN-23 (manufactured by Ajinomoto Fine-Techno Co., Inc.), Novacure HX-3721 (manufactured by Asahi Chemical Industry Co., Ltd.), and Fujicure FX-1000 (manufactured by Fuji Kasei Co., Ltd.). These polymerization catalysts and/or hardening accelerators can be used singly or in combination of two or more types.

The contents of the polymerization catalyst and the hardening accelerator can be appropriately adjusted, taking into consideration the hardness of the resin, the viscosity of the resin composition, and the like, and thus, the contents are not particularly limited. In general, such content is preferably 0.005 to 10 parts by mass based on 100 parts by mass of a resin solid content in the resin composition.

(Other Additives)

The resin composition of the present embodiment may further comprise, as necessary, other thermosetting resins, thermoplastic resins and the oligomers thereof, various polymer compounds such as elastomers, and known additives such as a hardening catalyst, a hardening accelerator, a coloring pigment, a defoaming agent, a surface adjuster, a fire retardant, a solvent, an ultraviolet absorber, an antioxidant, a photopolymerization initiator, a fluorescent brightener, a photosensitizer, a dye, a pigment, a thickener, a lubricant, a fluidity adjuster, a defoaming agent, a dispersant, a leveling agent, a brightening agent, a polymerization inhibitor, and a silane coupling agent. In addition, the resin composition of the present embodiment may comprise a solvent, as necessary. These any given additives can be used singly or in combination of two or more types.

As a fire retardant, a generally known fire retardant can be used, and the type of the fire retardant is not particularly limited. Specific examples thereof include: bromine compounds such as 4,4'-dibromobiphenyl; nitrogen compounds such as phosphoric acid ester, melamine phosphate, a phosphorus-containing epoxy resin, melamine, and benzoguanamine; and oxazine ring-containing compounds and silicon compounds.

It is to be noted that an organic solvent can be used for the resin composition of the present embodiment, as necessary. In this case, the resin composition of the present embodiment can be used in an aspect in which at least a part of, or preferably all of the aforementioned various resin components are dissolved in or compatible with an organic solvent (solution or varnish).

As such a solvent, a generally known solvent can be used, as long as it is able to solubilize or be compatible with at least a part of, or preferably all of the aforementioned various resin components, and thus, the type of the solvent is not particularly limited. Specific examples of such a solvent include: ketone solvents such as acetone, methyl ethyl ketone, methyl isobutyl ketone, and cyclohexanone; cellosolve solvents such as propylene glycol monomethyl ether and propylene glycol monomethyl ether; ester solvents such as ethyl lactate, methyl acetate, ethyl acetate, butyl acetate, isoamyl acetate, ethyl lactate, methyl methoxypropionate, and methyl hydroxyisobutyrate; polar solvents including amides such as dimethylacetamide and dimethylformamide; alcohol solvents such as methanol, ethanol, isopropanol, and 1-ethoxy-2-propanol; and aromatic hydrocarbons such as toluene, xylene, and anisole. These solvents can be used singly or in combination of two or more types.

The resin composition of the present embodiment can be obtained by mixing the aforementioned cyanate ester compound, and as necessary, other components together with a solvent, using a known mixer such as a high-speed mixer, a Nauta mixer, a ribbon blender, a kneader, an intensive mixer, a versatile mixer, a dissolver, or a static mixer. Upon the mixing operation, a method of adding a cyanate ester compound, various additives and a solvent is not particularly limited.

Since the resin composition of the present embodiment has low thermal expansion property, flame retardance and heat resistance at high levels, it is extremely useful as a high functional polymer material. The present resin composition is preferably used, as a raw material that is excellent in terms of thermal, electrical and mechanical properties, for electrical insulating materials, sealing materials, adhesives, laminating materials, resists, and build-up laminating materials, as well as for fixing materials, structural members, strengthening agents, casting materials and the like in the field of civil engineering and construction, electrical and electronics fields, automobile, railway, ships, aircrafts, sporting goods, arts and crafts, etc. Among these, the present resin composition is preferably used for electrical insulating materials, semiconductor sealing materials, adhesives for electronic components, aircraft structural members, satellite structural members, and structural members for both railway and automobile, which are required to have low thermal expansion, resistance to flame, and high mechanical strength.

[Hardened Product]

The hardened product of the present embodiment is produced by hardening the resin composition of the present embodiment. The method for producing such a hardened product is not particularly limited. A hardened product can be obtained, for example, by fusing the resin composition or dissolving it in a solvent, then supplying the resultant into a cast, and then hardening it with heat, light or the like under ordinary conditions. In the case of thermal hardening, the hardening temperature is not particularly limited. From the viewpoint of efficient progression of hardening and prevention of deterioration in the obtained hardened product, the hardening temperature is preferably set in a range of 120° C. to 300° C. In the case of light hardening, the wavelength range of the light is not particularly limited, and it is preferable to harden the resin composition in a range from 100 nm to 500 nm, in which hardening efficiently progresses with a photopolymerization initiator.

[Prepreg]

The prepreg of the present embodiment has a base material and the resin composition of the present embodiment, with which the base material is impregnated or coated. The prepreg can be used as an insulating layer of a printed wiring board, or a semiconductor packaging material.

(Base Material)

As a base material, a generally known base material can be appropriately selected and used, depending on performance required for a prepreg, such as strength, water absorption rate, coefficient of thermal expansion, etc. Thus, the type of the base material is not particularly limited. Specific examples thereof include a glass fiber base material, a synthetic fiber base material, an organic fiber base material, and an inorganic fiber base material. Examples of a glass fiber constituting the glass fiber base material include A-glass, C-glass, D-glass, E-glass, H-glass, L-glass, NE-glass, Q-glass, S-glass, T-glass, UN-glass, and sphere glass. Examples of a synthetic fiber constituting the synthetic fiber base material include: polyamide-based resin fibers such as polyamide resin fiber, aromatic polyamide resin fiber, and wholly aromatic polyamide resin fiber; polyester-based resin fibers such as polyester resin fiber, aromatic polyester resin fiber, and wholly aromatic polyester resin fiber; polyimide resin fiber; and fluorine resin fiber. Examples of the organic fiber base material include a craft paper, a cotton linter paper, and a paper base material comprising, as a main ingredient, a mixed paper of a linter and a craft pulp, etc. Examples of an inorganic fiber constituting the inorganic fiber base material include inorganic fibers other than glass, such as quartz. The shape of the base material is not particularly limited. Examples thereof include a woven fabric, a non-woven fabric, roving, a chopped strand mat, and a surfacing mat. The base materials can be used singly or in combination of two or more types. In addition, the thickness of the base material is not particularly limited. If the base material is used for a laminate, the thickness of the base material is preferably set in a range of 0.01 to 0.2 mm. From the viewpoint of dimension stability, a woven fabric, on which a ultra-opening treatment or a weather-stripping treatment has been performed, is particularly preferable. Furthermore, a glass woven fabric, the surface of which has been treated with silane coupling agents, such as an epoxysilane treatment or an aminosilane treatment, is preferable from the viewpoint of heat resistance upon moisture absorption. Further, a liquid crystal polyester woven fabric is preferable in terms of electrical properties.

As a method of producing a prepreg, a generally known method can be appropriately applied, and the type of the method is not particularly limited. Examples of the method of producing a prepreg include a method comprising preparing a resin varnish from the aforementioned resin composition and then immersing a base material in the resin varnish, a method of applying a resin varnish to a base material using various types of coaters, and a method of spraying a resin varnish to a base material using a spray. Among these methods, the method of immersing a base material in a resin varnish is preferable. By this method, the impregnation property of the resin composition to the base material can be improved. In a case in which a base material is immersed in a resin varnish, common impregnation application equipment can be used. For example, a method, which comprises impregnating an inorganic and/or organic fiber base material with a resin varnish, using such impregnation application equipment, and then drying the resulting base material at 120° C. to 220° C. for approximately 2 to 15 minutes, followed by obtaining a B-stage, so as to produce a prepreg. During this operation, the amount of a resin composition attached to a base material, namely, the amount of a resin composition (including an inorganic filler) to a total amount of a prepreg after being semihardened is preferably in a range of 20% to 99% by mass.

[Laminate]

The laminate of the present embodiment has a layer comprising at least one prepreg and a metallic foil laminated on one or both surfaces of the aforementioned layer. As a method of producing a laminate, a generally known method can be appropriately applied, and the type of the method is not particularly limited. For example, the above described prepreg is laminated on the above described metallic foil, followed by hot-press molding, to obtain a laminate. During this operation, the heating temperature is not particularly limited. It is preferably 65° C. to 300° C., and more preferably 120° C. to 270° C. In addition, the pressure applied in the above pressing operation is not particularly limited, and it is preferably 2 to 5 MPa, and more preferably 2.5 to 4 MPa. The laminate can also be used as a metal-clad laminate and a multilayer plate.

[Metal-Clad Laminate]

The metal-clad laminate of the present embodiment is produced by placing at least one of the above described prepreg and then disposing a metallic foil on one or both surfaces of the prepreg, followed by laminate molding. Specifically, one of the above described prepreg is placed or a plurality of the above described prepregs are laminated on one another, and a metallic foil such as a copper or aluminum foil is disposed on one or both surfaces of the layer, followed by laminate molding, so as to produce a metal-clad laminate. The metallic foil used herein is not particularly limited, as long as it is used as a raw material for printed wiring boards. A copper foil such as a rolled copper foil or an electrolytic copper foil is preferable. The thickness of the metallic foil is not particularly limited, and it is preferably 2 to 70 μm, and more preferably 3 to 35 μm. With regard to molding conditions, means for laminates and multilayer boards used for ordinary printed wiring boards can be applied. For instance, a multistage pressing machine, a multistage vacuum pressing machine, a continuous molding machine, an autoclave molding machine, and the like are used, and laminate molding is carried out at a temperature of 180° C. to 350° C., for a heating time of 100 to 300 minutes, and at a surface pressure of 20 to 100 kg/cm$^2$, so as to produce the metal-clad laminate of the present embodiment.

[Multilayer Board]

Moreover, the above described prepreg is combined with a circuit board used for inner layer, which has been produced separately. The combined product is subjected to laminate molding, so as to produce a multilayer board. As a method of producing such a multilayer board, for example, 35-μm copper foil is disposed on both surfaces of one of the above described prepreg, and the resultant is then subjected to laminate molding under the above described conditions. Thereafter, an internal circuit is formed, and the formed circuit is then subjected to a blackening treatment to form an internal circuit board. Thereafter, this internal circuit boards and the above described prepregs are disposed alternatively on a one-by-one base. Further a copper foil is disposed as an outermost layer, and the thus obtained layer is subjected to laminate molding under the above described conditions, and preferably under vacuum, so as to produce a multilayer board.

[Sealing Material]

The sealing material of the present embodiment comprises a resin composition. As a method of producing a sealing material, a generally known method can be appropriately applied, and thus, the method is not particularly limited. For example, the above described resin composition is mixed with various types of known additives that are generally used for sealing materials, solvents and the like, using a known mixer, so as to produce a sealing material. Upon mixing, as a method of adding a cyanate ester compound, various types of additives, and a solvent to the reaction system, a generally known method can be appropriately applied, and thus, the method is not particularly limited.

[Fiber-Reinforced Composite Material]

The fiber-reinforced composite material of the present embodiment comprises a resin composition and a reinforced fiber. As a reinforced fiber, a generally known reinforced fiber can be used, and the type of the reinforced fiber is not particularly limited. Specific examples of the reinforced fiber include carbon fiber, glass fiber, aramid fiber, boron fiber, PBO fiber, high-strength polyethylene fiber, alumina fiber, and silicon carbide fiber. The shape and sequence of the reinforced fiber are not particularly limited, and it can be appropriately selected from a woven fabric, a non-woven fabric, a mat, a knit, a braided cord, a one-direction strand, a roving strand, and a chopped strand. In addition, a preform (a product obtained by laminating woven base fabrics consisting of reinforced fibers on one another, or a product obtained by integrating such woven base fabrics by stitching them with a stitching yarn, or a fibrous structure such as a three-dimensional woven fabric or a braid) can also be applied as the shape of the reinforced fiber.

As a method of producing these fiber-reinforced composite materials, a generally known method can be appropriately applied, and thus, the method is not particularly limited. Specific examples of the production method include a liquid composite molding method, a resin film infusion method, a filament winding method, a hand lay-up method, and a pultrusion method. Among these methods, in the case of a resin transfer molding method that is one of liquid composite molding methods, raw materials other than a preform, such as a metallic plate, a form core, and a honeycomb core, could previously have been equipped into a forming die. Thus, since the resin transfer molding method can be applied to various intended uses, it is preferably used when a composite material having a relatively complicated shape is produced in a large amount in a short time.

[Adhesive]

The adhesive of the present embodiment comprises the resin composition of the present embodiment. As a method of producing an adhesive, a generally known method can be appropriately applied, and thus, the production method is not particularly limited. For example, the above described resin composition can be mixed with various types of known additives that are generally used as adhesives, solvents or the like, using a known mixer, so as to produce an adhesive. Upon mixing, as a method of adding a cyanate ester compound, various types of additives and a solvent to the reaction system, a generally known method can be appropriately applied, and thus, the method is not particularly limited.

[Resin Composite Sheet]

A resin composite sheet comprises a support and a resin layer disposed on the surface of the support, wherein resin layer comprises the resin composition of the present embodiment. On the other hand, the resin composite sheet of the present embodiment can be obtained by applying a solution prepared by dissolving the above described resin composition of the present embodiment in a solvent onto a support and then drying it. Examples of the support used herein include: a polyethylene film, a polypropylene film, a polycarbonate film, a polyethylene terephthalate film, an ethylene tetrafluoroethylene copolymer film, demolding films obtained by applying a demolding agent on the surface of these films, organic film base materials such as a polyimide film, conductor foils such as a copper foil and an aluminum foil, platy supports such as a glass plate, an SUS plate, and FRP, but examples thereof are not limited thereto. As an example of the method of applying the present resin composition onto a support is a method which comprises dissolving the resin composition of the present embodiment in a solvent and then applying the obtained solution onto a support using a bar coater, a die coater, a doctor blade, a baker applicator, etc. Moreover, after drying, the support may be removed or etched from the laminated sheet, so as to form a monolayer sheet (resin sheet). The above described resin composition of the present embodiment is dissolved in a solvent, the obtained solution is then supplied to a mold having a sheet-like cavity, and it is then molded into a sheet by drying it or the like, so that a monolayer sheet (resin sheet) can also be obtained without using supports.

In the production of the monolayer or laminated sheet of the present embodiment, drying conditions applied upon the removal of the solvent are not particularly limited. If the temperature is low, the solvent would easily remain in the resin composition. On the other hand, the temperature is high, the hardening of the resin composition would progress. Thus, drying is preferably carried out at a temperature of 20° C. to 200° C. for 1 to 90 minutes. In addition, the thickness of the monolayer or laminated sheet resin layer can be adjusted depending on the concentration of the solution of the resin composition of the present embodiment and the thickness of the solution coated, and thus, the thickness of the resin layer is not particularly limited. In general, as the thickness of the resin layer increases, the solvent easily remains during the drying. Thus, it is preferably 0.1 to 500 µm.

[Film]

A film is formed by molding the resin composition into a sheet. This film can be used, for example, as a build-up film or dry film solder resist. A method of producing such a film is not particularly limited. An example of the production method is a method which comprises applying a solution prepared by dissolving the resin composition of the present embodiment in a solvent onto a removable plastic film used as a base material, and then drying it. Herein, the solvent can be dried by heating it at a temperature of 20° C. to 150° C. for 1 to 90 minutes. In addition, the film can be used in an unhardened state in which only the solvent is dried away from the resin composition, or as necessary, the film can be used in a semihardened (B-staged) state.

[Printed Wiring Board]

The printed wiring board comprises an insulating layer and a conductor layer formed on the surface of the insulating layer, wherein the insulating layer comprises the resin composition of the present embodiment. That is to say, the aforementioned prepreg (a base material, and the resin composition of the present embodiment, with which the base material is impregnated or coated) and the resin composition layer of the aforementioned metal-clad laminate (a layer consisting of the resin composition of the present embodiment) are composed of an insulating layer comprising the resin composition of the present embodiment.

The metal-clad laminate of the present embodiment can be preferably used as a printed wiring board. The printed wiring board can be produced according to an ordinary method, and the production method is not particularly limited. Hereinafter, an example of the method of producing the printed wiring board will be described. First, the above described metal-clad laminate such as a copper-clad laminate is prepared. Subsequently, an etching processing is performed on the surface of the metal-clad laminate to form an internal circuit, thereby producing an internal base board. A surface treatment for enhancing adhesion strength is performed on the surface of the internal circuit of this internal base board, as necessary. Thereafter, a predetermined number of the above described prepregs are laminated on the surface of the internal circuit, and further, a metallic foil used as an external circuit is laminated on the outside thereof. The resultant is subjected to integral molding by heating and compression. As such, a multilayer laminate, in which an insulating layer consisting of a base material and a hardened product of resin composition is formed between an internal circuit and a metallic foil used as an external circuit, is produced. Subsequently, a hole-making processing of making a through hole or a via hole is performed on this multilayer laminate, and a plated metal coating for conducting the internal circuit and the metallic foil used as an external circuit to the wall surface of the hole is then formed. Furthermore, an etching processing is performed on the metallic foil used as an external circuit to form an external circuit, thereby producing a printed wiring board.

EXAMPLES

Hereinafter, the present invention will be described more in detail in the following examples. However, these examples are not particularly intended to limit the scope of the present invention.

(Confirmation of Unreacted Halogen at Terminal Point of Cyanogen Halide-Producing Step)

The reaction solution (40 g) obtained at the terminal point of the production of a cyanogen halide was added to a water/dichloromethane solution (15 g/10 g) cooled to 5° C., which had been prepared in advance, and thereafter, an operation to extract the cyanogen halide to a dichloromethane phase was carried out. The presence or absence of coloration was confirmed in each of the dichloromethane phase and the water phase. When the dichloromethane phase was colored, it was determined that unreacted halogen was present.

(Quantification of Generated Cyanogen Halide and Unreacted Hydrogen Cyanide at Terminal Point of Cyanogen Halide-Producing Step)

The reaction solution (40 g) obtained at the terminal point of the production of a cyanogen halide was added to a water/dichloromethane solution (15 g/10 g) cooled to 5° C., which had been prepared in advance, and thereafter, an operation to extract the cyanogen halide to a dichloromethane phase was carried out. Thereafter, 1 µL of the obtained dichloromethane phase was injected into gas chromatography (manufactured by Agilent Technologies, 6890), and it was then analyzed. In addition, 7.5 g of the obtained water phase, 7.5 g of a 50%-by-mass aqueous solution of N,N-dimethylformamide cooled to 5° C., which had been prepared in advance, and 0.15 g of 1,4-dioxane were mixed. After that, 1 µL of the thus obtained aqueous solution was injected into gas chromatography (manufactured by Agilent Technologies, 6890), and it was then analyzed. In the analysis of the water phase, FID was used as a detector, and DB-1 (30 m in length×0.32 mm in inner diameter×1 µm in film thickness) manufactured by Agilent Technologies was used. In addition, in the analysis of the dichloromethane phase, TCD was used as a detector, and DB-WAX (30 m in length×0.25 mm in inner diameter×0.25 µm in film thickness) manufactured by Agilent Technologies was used. With regard to the concentration (% by mass) of each of cyanogen halide, unreacted hydrogen cyanide and dichloromethane in the dichloromethane phase, the area % of each component with respect to 100% of the entire volatile component peak areas excluding air was calculated, and this area % was defined as % by mass. In addition, cyanogen halide, unreacted hydrogen cyanide and dichloromethane in the water phase were quantified according to an internal standard method using 1,4-dioxane as an internal standard. Based on the quantitative values of cyanogen halide, unreacted hydrogen cyanide and dichloromethane in the dichloromethane phase and the water phase, and the balance of dichloromethane, the amount of substance (mole A) of an unreacted hydrogen cyanide in a reaction solution and the amount of substance (mole B) of the generated cyanogen halide at the terminal point of the production of a cyanogen halide were obtained, and the ratio (A):(A)+(B) was then calculated.

(Tracing of the Degree of Reaction Progress in Cyanation Step)

A solution (2 µL) prepared by dissolving 1 g of the reaction solution (on the organic solvent side) in the cyanation step in 50 g of tetrahydrofuran (solvent) was injected into high performance liquid chromatography (manufactured by Hitachi High-Technologies Corporation, high performance liquid chromatograph LachromElite), and the analysis was then carried out. As a column, TSK gel ODS-120T (25 cm in length×4.6 mm in inner diameter) manufactured by Tosoh Corporation was used, and as a mobile phase, acetonitrile/water (volume ratio: 80/20) was used. The flow rate was set at 1 mL/min and the detection wavelength was set at 274 nm. The degree of reaction progress was defined as follows.

In a case in which 1,1-bis(4-hydroxyphenyl)isobutane represented by the following general formula (21), bis(4-hydroxyphenyl)biphenylmethane represented by the following general formula (22), and 2,2-bis(4-hydroxyphenyl) propane represented by the following general formula (23) were used as hydroxy-substituted aromatic compounds, the area value of a dicyanate ester compound (product of interest) was defined as C, the area value of a monocyanate ester compound (reaction intermediate) was defined as D, and the area value of a hydroxy-substituted aromatic compound (raw material) was defined as E. According to the following formula, the degree of reaction progress was obtained.

Degree of reaction progress (%)=$C/(C+D+E) \times 100$

Moreover, in a case in which tris(4-hydroxyphenyl)methane represented by the following general formula (24) was used as a hydroxy-substituted aromatic compound, the area value of a triscyanate ester compound (product of interest) was defined as F, the area value of a dicyanate ester compound (reaction intermediate) was defined as G, the area value of a monocyanate ester compound (reaction intermediate) was defined as H, and the area value of a hydroxy-substituted aromatic compound (raw material) was defined as I. According to the following formula, the degree of reaction progress was obtained.

Degree of reaction progress (%)=$F/(F+G+H+I) \times 100$

Furthermore, in a case in which 1-naphthol aralkyl resin (manufactured by Nippon Steel & Sumikin Chemical C., Ltd., product name: SN4 Series) represented by the following general formula (25) was used as a hydroxy-substituted aromatic compound, the area value of a dicyanate ester compound (product of interest) wherein n=1 was defined as J, the area value of a monocyanate ester compound (reaction intermediate) wherein n=1 was defined as K, and the area value of a hydroxy-substituted aromatic compound (raw material) wherein n=1 was defined as L. According to the following formula, the degree of reaction progress was obtained.

Degree of reaction progress (%)=$J/(J+K+L)\times 100$

[Formula 37]

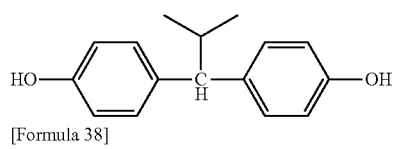
(21)

[Formula 38]

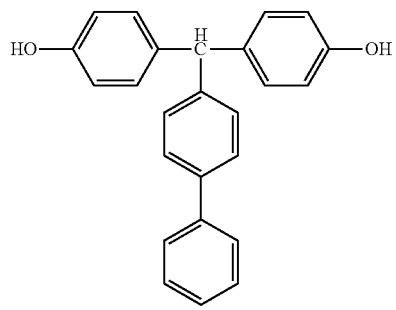
(22)

[Formula 39]

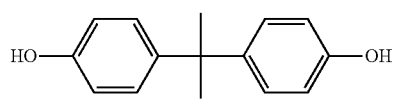
(23)

[Formula 40]

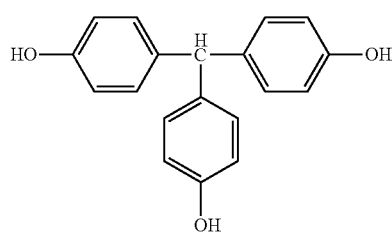
(24)

[Formula 41]

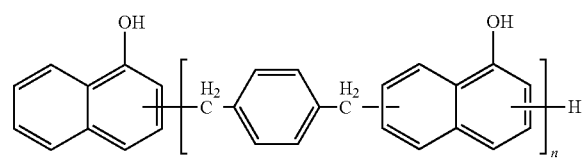
(25)

wherein n represents an integer of 1 to 50.

(Analysis of Dicyan as by-Product in Cyanation Step)

1 µL of the reaction solution (on the organic solvent side) in the cyanation step was injected into gas chromatography (manufactured by Agilent Technologies, 6850), and the analysis was then carried out. As a detector, TCD was used, and as a column, DB-WAX (30 cm in length×0.25 mm in inner diameter×0.25 µm in film thickness) manufactured by Agilent Technologies was used. With regard to the concentrations (% by mass) of the subgenerated dicyan (and dialkylcyanamide) in volatile components, the area % of each component with respect to 100% of the entire volatile component peak areas excluding air was calculated, and this area % was defined as % by mass in the volatile components.

(Quantitative Analysis of Hydrolyzable Halogen in Cyanate Ester Compound Obtained in Cyanation Step)

1 g of a cyanate ester compound was dissolved in 30 mL of 1,4-dioxane (solvent), and a 5 mol/L potassium hydroxide/water-methanol solution was then added to the above obtained solution. The solution was heated under reflux conditions for 1 hour (bath temperature: 150° C.), and thereafter, the amount of halogen ion desorbed (M) was measured by potentiometric titration using a silver nitrate solution. For the titration, the potential-difference automatic titration device Titrando 809, manufactured by Metrohm, was used, and as an electrode, a silver electrode was used. In addition, 1 g of a cyanate ester compound was dissolved in 150 mL of 2-butanone (solvent), separately. The amount of halogen ion in this solution (N) was measured by potentiometric titration using a silver nitrate solution. The value obtained by subtracting (N) from (M) was defined as hydrolyzable halogen, and it was then evaluated.

(Quantitative Analysis of Total Halogen in Cyanate Ester Compound Obtained in Cyanation Step)

5 mg of a cyanate ester compound was combusted and decomposed at 1000° C. with ventilation of argon/oxygen gas, and the generated halogen-containing gas was captured in an absorption solution (an aqueous solution containing phosphoric acid (phosphorus atom concentration: 1 mg/L) and hydrogen peroxide (60 mg/L)). Thereafter, 100 µL of this absorption solution was injected into an ion chromatograph (manufactured by Dionex, Dionex ICS-1500), and the analysis was then carried out. A calibration curve had previously been prepared using an ion chromatography standard solution, and halogen was then quantified according to an absolute calibration method. The obtained quantitative value was defined as total halogen, and it was then evaluated. For combustion and decomposition of the cyanate ester compound, AQF-100+GA100 manufactured by Dia Instruments Co., Ltd. was used. As columns for ion chromatography, IonPac AG12A and AS12A manufactured by Dionex were used, and as a mobile phase, 2.7 mM sodium carbonate+0.3 mM sodium hydrogen carbonate were used. The flow rate was set at 1.5 mL/min, and a device for detecting electric conductivity was used as a detector.

(Measurement 1 of Gelatinization Time of Cyanate Ester Compound Obtained in Cyanation Step)

A time required for gelatinization of a cyanate ester compound at 170° C. was measured using a gelatinization test apparatus (R-1-4-704 manufactured by Nisshin-Kagaku Inc.).

(Measurement 2 of Gelatinization Time of Cyanate Ester Compound Obtained in Cyanation Step)

50 parts by mass of a cyanate ester compound, 50 parts by mass of a biphenyl aralkyl-based epoxy resin (manufactured by Nippon Kayaku Co., Ltd., NC3000FH), and 0.05 parts by mass of zinc octylate (manufactured by Nihon Kagaku Sangyo Co., Ltd., trademark: Nikka Octhix Zinc, metal content: 18%) were stirred and mixed to obtain a composition. The time required for gelatinizaiton of the obtained composition at 170° C. was measured using a gelatinization test apparatus (R-1-4-704 manufactured by Nisshin-Kagaku Inc.).

Example 1

145.5 g (2.05 mol) of chlorine (manufactured by Fujiox Co., Ltd.) was blown into 1464 g of a 3.8%-by-mass aqueous solution of hydrogen cyanide (56.3 g (2.08 mol) of hydrogen cyanide and 1407.3 g of water), while keeping the liquid temperature at 0° C. to 5° C., under stirring over 7 hours. The used amount of the hydrogen cyanide was set at 1.0153 moles based on 1 mole of chlorine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that no unreacted chlorine molecules were present (the inversion percentage of the chlorine was 99.9% or more).

In addition, the ratio (A):(A)+(B) in the solution at the reaction terminal point was 0.02100:1.

While the liquid temperature was kept at 0° C. to 5° C., 249 g of dichloromethane was added to the solution after completion of the reaction, and the obtained solution was defined as solution 1. These results are shown in Table 1.

Example 2

300 g (1.28 mol relative to OH group) of 1-naphthol aralkyl resin (manufactured by Nippon Steel & Sumikin Chemical Co., Ltd.) and 194.6 g (1.92 mol) of triethylamine (in an amount of 1.5 moles based on 1 mole of hydroxy group of the hydroxy group-substituted aromatic compound) were dissolved in 1800 g of dichloromethane, and the obtained solution was defined as solution 2.

The solution 2 was added dropwise to the solution 1 (in which the amount of a cyanogen chloride was 1.5 moles based on 1 mole of hydroxy group of the hydroxy group-substituted aromatic compound) (cyanogen halide solution e) under stirring, while keeping the liquid temperature at −2° C. to −0.5° C., over 30 minutes. After dropwise addition of the solution 2, the degree of reaction progress was 80.6%, and the dicyan concentration was 0.071% by mass. After completion of the dropwise addition of the solution 2, the reaction solution was stirred at the same temperature as described above for 30 minutes, and a solution prepared by dissolving 65 g (0.64 mol) of triethylamine (in an amount of 0.5 moles based on 1 mole of hydroxy group of the hydroxy group-substituted aromatic compound) in 65 g of dichloromethane (solution 3) was added dropwise to the reaction solution over 10 minutes. After dropwise addition of the solution 3, the degree of reaction progress was 99.5%, and the dicyan concentration was 0.075% by mass. After completion of the dropwise addition of the solution 3, the reaction solution was stirred at the same temperature as described above for 30 minutes. The pH of the reaction solution during the reaction was measured with a pH meter (manufactured by IQ Scientific Instruments, product name: IQ150). As a result, the pH was −0.1 or less. The degree of reaction progress in the production of a cyanate ester with respect to the amount of a basic catalyst used is shown in Table 2, and the concentration of dicyan as a by-product with respect to the amount of a basic compound used is shown in Table 3.

Thereafter, the reaction solution was left at rest, so that a dichloromethane phase was separated from a water phase. The obtained dichloromethane phase was washed with 1300 g of water five times. The electric conductivity of the waste water at the 5th water washing was 5 µS/cm, and thus, it was confirmed that an ionic compound to be removed was sufficiently removed by washing with water.

After completion of the water washing, the dichloromethane phase was concentrated under reduced pressure, and the solvent was then replaced with a 2-butanone solution five times, to obtain 663 g of a 2-butanone solution containing 50% by mass of a cyanate ester compound of interest. The concentration of hydrolyzable chlorine in the obtained cyanate ester compound was 23 ppm, the total chlorine was 141 ppm, gelatinization time 1 was 68 minutes, and gelatinization time 2 was 12.9 minutes. These results are shown in Table 4. In addition, conditions for the cyanation step are shown in Table 5, and the content of a method of using a cyanogen halide is shown in Table 6.

Example 3

32.3 g (0.65 mol) of 98%-by-mass sodium cyanide was dissolved in 128 g of water, and the obtained solution was defined as solution 4. The solution 4 was added dropwise to 91.2 g of a 36%-by-mass aqueous solution of hydrochloric acid (hydrochloric acid: 0.9 mol) (in an amount of 1.39 moles with respect to the sodium cyanide) and 317.7 g of water under stirring, while keeping the liquid temperature at −3° C. to −1° C., over 36 minutes. After completion of the dropwise addition of the solution 4, 45.4 g (0.64 mol) of chlorine (manufactured by Fujiox Co., Ltd.) was blown into the reaction solution, while keeping the liquid temperature at −2° C. to −1° C., over 3 hours. The amount of the sodium cyanide used was set at 1.0088 moles based on 1 mole of chlorine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted chlorine molecules disappeared (the inversion percentage of the chlorine was 99.9% or more).

In addition, the ratio (A):(A)+(B) in the solution at the reaction terminal point was 0.02174:1.

While the liquid temperature was kept at 0° C. to 5° C., 91.8 g of dichloromethane and 10 g of water were added to the reaction solution. The obtained solution was defined as solution 5. These results are shown in Table 1.

Example 4

48.5 g (0.40 mol relative to OH group) of 1,1-bis(4-hydroxyphenyl)isobutane (manufactured by Wako Pure Chemical Industries, Ltd.) and 72.9 g (0.72 mol) of triethylamine (in an amount of 1.8 moles based on 1 mole of hydroxy group of the hydroxy group-substituted aromatic compound) were dissolved in 118.6 g of dichloromethane, and the obtained solution was defined as solution 6. The solution 6 was added dropwise to the solution 5 (in which the amount of a cyanogen chloride was 1.6 moles based on 1 mole of hydroxy group of the hydroxy group-substituted aromatic compound) (cyanogen halide solution f) under stirring, while keeping the liquid temperature at −7° C. to −1° C., over 29 minutes. After dropwise addition of the solution 6, the degree of reaction progress was 37.1%. After completion of the dropwise addition of the solution 6, the reaction solution was stirred at the same temperature as described above for 30 minutes, and a solution prepared by dissolving 28.4 g (0.28 mol) of triethylamine (in an amount of 0.7 moles based on 1 mole of hydroxy group of the hydroxy group-substituted aromatic compound) in 28.4 g of dichloromethane (solution 7) was added dropwise to the reaction solution over 9 minutes. After dropwise addition of the solution 7, the degree of reaction progress was 95.3%. After completion of the dropwise addition of the solution 7, the reaction solution was stirred at the same temperature as described above for 30 minutes. Thereafter, a solution prepared by dissolving 8.1 g (0.08 mol) of triethylamine (in an amount of 0.2 moles based on 1 mole of hydroxy group of the hydroxy group-substituted aromatic compound) in 8.1 g of dichloromethane (solution 8) was added dropwise to the reaction solution over 2.6 minutes. After dropwise addition of the solution 8, the degree of reaction progress was 99.6%. After completion of the dropwise addition of the solution 8, the reaction solution was stirred at the same temperature as described above for 30 minutes. The pH of the reaction solution during the reaction was −0.2 or less. The degree of reaction progress in the production of a cyanate ester with respect to the amount of a basic catalyst used is shown in Table 2.

Thereafter, the reaction solution was left at rest, so that a dichloromethane phase was separated from a water phase. The obtained dichloromethane phase was washed with 201 g of a 0.1 mol/L hydrochloric acid solution once, and then with 201 g of water five times. The electric conductivity of the waste water at the 5th water washing was 8 µS/cm, and thus, it was confirmed that an ionic compound to be removed was sufficiently removed by washing with water. After completion of the water washing, the dichloromethane phase was concentrated under reduced pressure, and finally, it was concentrated and dried at 90° C. for 1 hour to obtain 58.2 g of 1,1-bis(4-cyanatophenyl)isobutane of interest. The concentration of hydrolyzable chlorine in the obtained cyanate ester compound was 40 ppm. These results are shown in Table 4. In addition, conditions for the cyanation step are shown in Table 5, and the content of a method of using a cyanogen halide is shown in Table 6.

Example 5

34.0 g (0.68 mol) of 98%-by-mass sodium cyanide was dissolved in 98.0 g of water, and the obtained solution was defined as solution 9. The solution 9 was added dropwise to 71.0 g of a 36%-by-mass aqueous solution of hydrochloric acid (hydrochloric acid: 0.70 mol) (in an amount of 1.03 moles with respect to the sodium cyanide) and 294.1 g of water under stirring, while keeping the liquid temperature at 0° C. to 5° C., over 20 minutes. The obtained solution was defined as solution 10. The solution 10 was added dropwise to a 29%-by-mass aqueous solution of bromine (bromine: 107.6 g (0.67 mol) (manufactured by Wako Pure Chemical Industries, Ltd.), and water: 263.5 g) under stirring, while keeping the liquid temperature at 0° C. to 5° C., over 3.2 hours. The amount of the sodium cyanide used was set at 1.0091 moles with respect to bromine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted bromine molecules disappeared (the inversion percentage of the bromine was 99.9% or more).

In addition, the ratio (A):(A)+(B) in the solution at the reaction terminal point was 0.00645:1.

While the liquid temperature was kept at 0° C. to 5° C., 149.3 g of chloroform was added to the present reaction solution, and the obtained solution was then stirred and mixed. Thereafter, the mixed solution was left at rest, so that an organic phase was physically separated from a water phase, to obtain a chloroform solution containing 23% by mass of cyanogen bromide (solution 11). These results are shown in Table 1.

Example 6

40 g (0.19 mol relative to OH group) of 1-naphthol aralkyl resin (manufactured by Nippon Steel & Sumikin Chemical Co., Ltd.) and 20.6 g (0.20 mol) of triethylamine (in an amount of 1.1 moles based on 1 mole of hydroxy group of the hydroxy group-substituted aromatic compound) were dissolved in 240 g of chloroform, and the obtained solution was defined as solution 12. The solution 12 was added dropwise to 170.6 g of the solution 11 (in which the amount of a cyanogen bromide was 2.0 moles based on 1 mole of hydroxy group of the hydroxy group-substituted aromatic compound) (cyanogen halide solution g) under stirring, while keeping the liquid temperature at −7° C. to −3° C., over 40 minutes. After completion of the dropwise addition of the solution 12, the reaction solution was stirred at the same temperature as described above for 30 minutes, and a solution prepared by dissolving 15.0 g (0.15 mol) of triethylamine (in an amount of 0.8 moles based on 1 mole of hydroxy group of the hydroxy group-substituted aromatic compound) in 30 g of chloroform (solution 13) was added dropwise to the reaction solution over 30 minutes. After dropwise addition of the solution 13, the degree of reaction progress was 98.7%. The degree of reaction progress in the production of a cyanate ester with respect to the amount of a basic compound used is shown in Table 2.

The reaction solution was filtrated, and the obtained filtrate was washed with 500 g of a 0.1 mol/L hydrochloric acid solution once, and then with 500 g of water four times. The electric conductivity of the waste water at the 4th water washing was 30 µS/cm, and thus, it was confirmed that an ionic compound to be removed was sufficiently removed by washing with water. After completion of the water washing, the organic phase was concentrated under reduced pressure, and finally, it was concentrated and dried at 90° C. for 1 hour to obtain 44 g of a cyanate ester compound of interest. The concentration of hydrolyzable bromine in the obtained cyanate ester compound was 25 ppm. These results are shown in Table 4. In addition, conditions for the cyanation step are shown in Table 5, and the content of a method of using a cyanogen halide is shown in Table 6.

Example 7

14.1 g (0.28 mol) of 98%-by-mass sodium cyanide was dissolved in 40.8 g of water, and the obtained solution was defined as solution 14. The solution 14 was added dropwise to 29.5 g of a 36%-by-mass aqueous solution of hydrochloric acid (hydrochloric acid: 0.29 mol) (in an amount of 1.03 moles with respect to the sodium cyanide) and 122.4 g of water under stirring, while keeping the liquid temperature at 0° C. to 5° C., over 10 minutes. The obtained solution was defined as solution 15. The solution 15 was added dropwise to a 29%-by-mass aqueous solution of bromine (bromine: 44.8 g (0.28 mol) (manufactured by Wako Pure Chemical Industries, Ltd.) and water: 109.6 g) under stirring, while keeping the liquid temperature at 0° C. to 5° C., over 1.3 hours. The amount of the sodium cyanide used was set at 1.0091 moles with respect to bromine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted bromine molecules disappeared (the inversion percentage of the bromine was 99.9% or more). In addition, the ratio (A):(A)+(B) in the solution at the reaction terminal point was 0.00645:1. While the liquid temperature was kept at 0° C. to 5° C., 62.1 g of chloroform was added to the present reaction solution, and the obtained solution was then stirred and mixed. Thereafter, the mixed solution was left at rest, so that an organic phase was physically separated from a water phase, to obtain a chloroform solution containing 23% by mass of cyanogen bromide (solution 16). These results are shown in Table 1.

Example 8

50 g of tetrahydrofuran and 10 g (0.10 mol relative to OH group) of tris(4-hydroxyphenyl)methane (manufactured by Honshu Chemical Industry Co., Ltd.) were added to and dissolved in 71.0 g of the solution 16 (in which the amount of a cyanogen bromide was 1.5 moles based on 1 mole of hydroxy group of the hydroxy group-substituted aromatic compound), and the obtained solution was defined as solution 17 (cyanogen halide solution h). A solution prepared by dissolving 14.6 g (0.14 mol) of triethylamine (in an amount of 1.4 moles based on 1 mole of hydroxy group of the hydroxy group-substituted aromatic compound) in 42 g of chloroform (solution 18) was added dropwise to the solution 17 under stirring, while keeping the liquid temperature at −7° C. to −1° C., over 30 minutes. After completion of the dropwise addition of the solution 18, the degree of reaction progress was 98.5%.

The reaction solution was filtered, and the obtained filtrate was washed with 100 g of a 0.1 mol/L hydrochloric acid solution once, and then with 100 g of water four times. The electric conductivity of the waste water at the 4th water washing was 30 µS/cm, and thus, it was confirmed that an ionic compound to be removed was sufficiently removed by washing with water. Thereafter, sodium sulfate was added to the resulting solution for the absorption removal of water content, and the resultant was then concentrated at 50° C. under reduced pressure to obtain a yellow crude crystal. The obtained crude crystal was recrystallized from a mixed solvent of hexane and acetone. The resultant was filtered and washed with hexane, followed by vacuum drying, to obtain 12.5 g of tris(4-cyanatophenyl)methane of interest. The concentration of hydrolyzable bromine in the obtained cyanate ester compound was 30 ppm. These results are shown in Table 4. In addition, conditions for the cyanation step are shown in Table 5, and the content of a method of using a cyanogen halide is shown in Table 6.

Example 9

476.4 g (6.72 mol) of chlorine (manufactured by Fujiox Co., Ltd.) was blown into 3587.5 g of a 5.2%-by-mass aqueous solution of hydrogen cyanide (hydrogen cyanide: 187.5 g (6.94 mol) and water: 3400 g) under stirring, while keeping the liquid temperature at −5° C. to 0° C., over 6 hours. The amount of the hydrogen cyanide used was set at 1.0336 moles with respect to chlorine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted chlorine molecules disappeared (the inversion percentage of the chlorine was 99.9% or more). In addition, the ratio (A):(A)+(B) in the solution at the reaction terminal point was 0.00641:1. While the liquid temperature was kept at −5° C. to 0° C., 992.7 g of dichloromethane and 1580.2 g of water were added to the present reaction solution, and the obtained solution was then stirred and mixed. Thereafter, the mixed solution was left at rest, so that a dichloromethane phase was physically separated from a water phase, to obtain a dichloromethane solution containing 23.3% cyanogen chloride (solution 19). After completion of the liquid separation, the ratio (A):(A)+(B) was 0.00456:1. These results are shown in Table 1.

Example 10

50 g (0.28 mol relative to OH group) of bis(4-hydroxyphenyl)biphenylmethane, 12.5 g (0.31 mol) of sodium hydroxide (in an amount of 1.1 moles based on 1 mole of hydroxy group of the hydroxy group-substituted aromatic compound), and 5.0 g (0.05 mol) of triethylamine (in an amount of 0.17 moles based on 1 mole of hydroxy group of the hydroxy group-substituted aromatic compound) were dissolved in 550 g of water, and the obtained solution was defined as solution 20. The solution 20 was added dropwise to 127.4 g of the solution 19 (in which the amount of a cyanogen chloride was 1.7 moles based on 1 mole of hydroxy group of the hydroxy group-substituted aromatic compound) (cyanogen halide solution g) under stirring, while keeping the liquid temperature at −5° C. to 0° C., over 2 hours. After completion of the dropwise addition of the solution 20, the reaction solution was stirred at the same temperature as described above for 30 minutes. Thereafter, a solution prepared by dissolving 4.6 g (0.12 mol) of sodium hydroxide (in an amount of 0.4 moles based on 1 mole of hydroxy group of the hydroxy group-substituted aromatic compound) in 200 g of water (solution 21) was added dropwise to the reaction solution over 1 hour. After the dropwise addition of the solution 21, the degree of reaction progress was 94.9%. After completion of the dropwise addition of the solution 21, the reaction solution was stirred at the same temperature as described above for 30 minutes. The degree of reaction progress in the production of a cyanate ester with respect to the amount of a basic compound used is shown in Table 2.

Thereafter, the reaction solution was left at rest, so that a dichloromethane phase was separated from a water phase. The obtained dichloromethane phase was washed with 1000 g of water four times. The electric conductivity of the waste water at the 4th water washing was 20 µS/cm, and thus, it was confirmed that an ionic compound to be removed was sufficiently removed by washing with water. After completion of the water washing, the dichloromethane phase was concentrated under reduced pressure, and finally, it was concentrated and dried at 80° C. for 2 hours to obtain 53 g of bis(4-cyanatophenyl)biphenylmethane of interest. The concentration of hydrolyzable chlorine in the obtained cyanate ester compound was 35 ppm. These results are shown in Table 4. In addition, conditions for the cyanation step are shown in Table 5, and the content of a method of using a cyanogen halide is shown in Table 6.

Example 11

1000 g (14.1 mol) of chlorine (manufactured by Fujiox Co., Ltd.) was blown into 3660 g of a 11.2%-by-mass aqueous solution of hydrogen cyanide (hydrogen cyanide: 410 g (15.2 mol) and water: 3250 g) under stirring, while keeping the liquid temperature at −5° C. to 4.5° C., over 4.7 hours. The amount of the hydrogen cyanide used was set at 1.0768 moles with respect to chlorine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted chlorine molecules disappeared (the inversion percentage of the chlorine was 99.9% or more). In addition, the ratio (A):(A)+(B) in the solution at the reaction terminal point was 0.00884:1. While the liquid temperature was kept at −5° C. to 0° C., 4000 g of dichloromethane was added to the present reaction solution, and the obtained solution was then stirred and mixed. Thereafter, the mixed solution was left at rest, so that a dichloromethane phase was physically separated from a water phase, to obtain a dichloromethane solution containing 23.3% cyanogen chloride (solution 22). After completion of the liquid separation, the ratio (A):(A)+(B) was 0.00658:1. These results are shown in Table 1.

Example 12

2850 g (25.0 mol relative to OH group) of 2,2-bis(4-hydroxyphenyl)propane (manufactured by Wako Pure Chemical Industries, Ltd.), 1119 g (28.0 mol) of sodium hydroxide (in an amount of 1.12 moles based on 1 mole of hydroxy group of the hydroxy group-substituted aromatic compound), and 75 g (0.74 mol) of triethylamine (in an amount of 0.03 moles based on 1 mole of hydroxy group of the hydroxy group-substituted aromatic compound) were dissolved in 34 kg of water, and the obtained solution was defined as solution 23. After the solution 22 (in which the amount of a cyanogen chloride was 1.43 moles based on 1 mole of hydroxy group of the hydroxy group-substituted aromatic compound) (cyanogen halide solution g) had been continuously supplied at a rate of 400 g/hr while keeping the liquid temperature at 0° C. to 2° C., the solution 23 was continuously supplied at a rate of 1636 g/hr while keeping the liquid temperature at 0° C. to 5° C. After completion of the supply of the solution 22 and the solution 23, the degree of reaction progress was 98.5%. The degree of reaction progress in the production of a cyanate ester with respect to the amount of a basic compound used is shown in Table 2.

The obtained reaction solution was subjected to countercurrent extraction with water at a liquid temperature of 30° C. to 32° C. at a rate of 600 g/hr. After washing with water, the dichloromethane phase was concentrated under reduced pressure, and finally, it was concentrated and dried at 95° C. to obtain 3422 g of 2,2-bis(4-cyanatophenyl)propane of interest. The concentration of total chlorine in the obtained cyanate ester compound was 52 ppm. These results are shown in Table 4. In addition, conditions for the cyanation step are shown in Table 5, and the content of a method of using a cyanogen halide is shown in Table 6.

Comparative Example 1

Cyanogen chloride was synthesized in the same manner as that of Example 1, with the exception that 1381 g of a 4.0%-by-mass aqueous solution of hydrogen cyanide (hydrogen cyanide: 55.5 g (2.06 mol) and water: 1326 g) and 153.9 g (2.17 mol) of chlorine (manufactured by Fujiox Co., Ltd.) were used (in which the amount of a hydrogen cyanide was 0.9478 moles with respect to chlorine molecules). The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, the water phase was colorless and the dichloromethane phase was yellow, and thus, it was confirmed that unreacted chlorine molecules were present (the inversion percentage of the chlorine was less than 99.9%). Moreover, unreacted hydrogen cyanide was not detected in this reaction solution at the reaction terminal point. While the liquid temperature was kept at 0° C. to 5° C., 245.9 g of dichloromethane was added to the present reaction solution, and the obtained solution was defined as solution 24. These results are shown in Table 1.

Comparative Example 2

300 g (1.28 mol relative to OH group) of 1-naphthol aralkyl resin (manufactured by Nippon Steel & Sumikin Chemical Co., Ltd.) and 194.6 g (1.92 mol) of triethylamine (in an amount of 1.5 moles based on 1 mole of hydroxy group of the hydroxy group-substituted aromatic compound) were dissolved in 1800 g of dichloromethane, and the obtained solution was defined as solution 25. The solution 25 was added dropwise to the solution 24 (in which the amount of a cyanogen chloride was 1.5 moles based on 1 mole of hydroxy group of the hydroxy group-substituted aromatic compound) (cyanogen halide solution e) under stirring, while keeping the liquid temperature at −4° C. to −1° C., over 30 minutes. After dropwise addition of the solution 25, the degree of reaction progress was 83.9%. After completion of the dropwise addition of the solution 25, the reaction solution was stirred at the same temperature as described above for 30 minutes, and a solution prepared by dissolving 52 g (0.51 mol) of triethylamine (in an amount of 0.4 moles based on 1 mole of hydroxy group of the hydroxy group-substituted aromatic compound) in 52 g of dichloromethane (solution 26) was added dropwise to the reaction solution over 8 minutes. After dropwise addition of the solution 26, the degree of reaction progress was 97.7%. After completion of the dropwise addition of the solution 26, the reaction solution was stirred at the same temperature as described above for 30 minutes, and a solution prepared by dissolving 26 g (0.26 mol) of triethylamine (in an amount of 0.2 moles based on 1 mole of hydroxy group of the hydroxy group-substituted aromatic compound) in 26 g of dichloromethane (solution 27) was added dropwise to the reaction solution over 4 minutes. After dropwise addition of the solution 27, the degree of reaction progress was 98.8%. After completion of the dropwise addition of the solution 27, the reaction solution was stirred at the same temperature as described above for 30 minutes. The pH of the reaction solution during the reaction was 0.1 or less. The degree of reaction progress in the production of a cyanate ester with respect to the amount of a basic compound used is shown in Table 2.

Thereafter, the reaction solution was left at rest, so that a dichloromethane phase was separated from a water phase. The obtained dichloromethane phase was washed with 2000 g of water five times. The electric conductivity of the waste water at the 5th water washing was 19 μS/cm, and thus, it was confirmed that an ionic compound to be removed was sufficiently removed by washing with water. After completion of the water washing, the dichloromethane phase was concentrated under reduced pressure, and the solvent was then replaced with a 2-butanone solution five times, to obtain 1150 g of a 2-butanone solution containing 50% by mass of a cyanate ester compound of interest. The concentration of hydrolyzable chlorine in the obtained cyanate ester compound was 2160 ppm, the total chlorine was 4500 ppm, gelatinization time 1 was 27 minutes, and gelatinization time 2 was 9.5 minutes. These results are shown in Table 4. In addition, conditions for the cyanation step are shown in Table 5, and the content of a method of using a cyanogen halide is shown in Table 6.

Comparative Example 3

The synthesis of cyanogen chloride and a post-treatment were carried out in the same manner as that of Example 11, with the exception that 3650 g of a 11.0%-by-mass aqueous solution of hydrogen cyanide (hydrogen cyanide: 400 g (14.8 mol) and water: 3250 g) and 1100 g (15.5 mol) of chlorine (manufactured by Fujiox Co., Ltd.) were used (in which the amount of a hydrogen cyanide was 0.9550 moles with respect to chlorine molecules). 40 g of the reaction solution obtained at the terminal point of the reaction of synthesizing cyanogen chloride was added to a water/dichloromethane solution (15 g/10 g) cooled to 5° C., which had been prepared in advance, and the obtained mixture was then subjected to an extraction operation. As a result, the water phase was colorless and the dichloromethane phase was yellow, and thus, it was confirmed that unreacted chlorine molecules were present (the inversion percentage of the chlorine was less than 99.9%). Moreover, unreacted hydrogen cyanide was not detected in this reaction solution at the reaction terminal point. The reaction solution was defined as solution 28. These results are shown in Table 1.

Comparative Example 4

Cyanate ester was synthesized in the same manner as that of Example 12 with the exception that the solution 28 obtained in Comparative Example 3 was used. After completion of the supply of the solution 22 and the solution 23, the degree of reaction progress was 97.9%. The degree of reaction progress in the production of a cyanate ester with respect to the amount of a basic compound used is shown in Table 2.

The concentration of total chlorine in the obtained cyanate ester compound was 793 ppm. These results are shown in Table 4. In addition, conditions for the cyanation step are shown in Table 5, and the content of a method of using a cyanogen halide is shown in Table 6.

Example 13

464.0 g (6.54 mol) of chlorine (manufactured by Fujiox Co., Ltd.) was blown into 3436.1 g of a 5.4%-by-mass aqueous solution of hydrogen cyanide (hydrogen cyanide: 186.1 g (6.89 mol) and water: 3250 g) under stirring, while keeping the liquid temperature at −5° C. to 0° C., over 6 hours. The amount of the hydrogen cyanide used was set at 1.0533 moles with respect to chlorine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted chlorine molecules disappeared (the inversion percentage of the chlorine was 99.9% or more). In addition, the ratio (A):(A)+(B) in the solution at the reaction terminal point was 0.01891:1. While the liquid temperature was kept at −5° C. to 0° C., 983.8 g of dichloromethane and 1580 g of water were added to the present reaction solution, and the obtained solution was defined as solution 29. These results are shown in Table 1.

Example 14

1050 g (4.52 mol relative to OH group) of 1-naphthol aralkyl resin (manufactured by Nippon Steel & Sumikin Chemical Co., Ltd.) and 686 g (6.78 mol) of triethylamine (in an amount of 1.5 moles based on 1 mole of hydroxy group of the hydroxy group-substituted aromatic compound) were dissolved in 5775 g of dichloromethane, and the obtained solution was defined as solution 30. The solution 30 was added dropwise to the solution 29 (in which the amount of a cyanogen chloride was 1.37 moles based on 1 mole of hydroxy group of the hydroxy group-substituted aromatic compound) (cyanogen halide solution f) under stirring, while keeping the liquid temperature at −4° C. to −2° C., over 1.8 hours. After dropwise addition of the solution 30, the degree of reaction progress was 85.6%, and the dicyan concentration was 0.069% by mass. After completion of the dropwise addition of the solution 30, the reaction solution was stirred at the same temperature as described above for 30 minutes, and a solution prepared by dissolving 247 g (2.44 mol) of triethylamine (in an amount of 0.54 moles based on 1 mole of hydroxy group of the hydroxy group-substituted aromatic compound) in 247 g of dichloromethane (solution 31) was added dropwise to the reaction solution over 38 minutes. After dropwise addition of the solution 31, the degree of reaction progress was 98.7%, and the dicyan concentration was 0.087% by mass. After completion of the dropwise addition of the solution 31, the reaction solution was stirred at the same temperature as described above for 30 minutes. The pH of the reaction solution during the reaction was 0.63 or less. The degree of reaction progress in the production of a cyanate ester with respect to the amount of a basic compound used is shown in Table 2, and the concentration of dicyan as a by-product with respect to the amount of a basic compound used is shown in Table 3.

Thereafter, the reaction solution was left at rest, so that a dichloromethane phase was separated from a water phase. The obtained dichloromethane phase was washed with 3000 kg of water six times. The electric conductivity of the waste water at the 6th water washing was 25 μS/cm, and thus, it was confirmed that an ionic compound to be removed was sufficiently removed by washing with water. After completion of the water washing, the dichloromethane phase was concentrated under reduced pressure, and the solvent was then replaced with a 2-butanone solution five times, to obtain 2323 g of a 2-butanone solution containing 50% by mass of a cyanate ester compound of interest. The concentration of hydrolyzable chlorine in the obtained cyanate ester compound was 21 ppm. These results are shown in Table 4. In addition, conditions for the cyanation step are shown in Table 5, and the content of a method of using a cyanogen halide is shown in Table 6.

Example 15

507.2 g (7.15 mol) of chlorine (manufactured by Fujiox Co., Ltd.) was blown into 3608.4 g of a 5.5%-by-mass aqueous solution of hydrogen cyanide (hydrogen cyanide: 197.4 g (7.31 mol) and water: 3411 g) under stirring, while keeping the liquid temperature at −5° C. to 0° C., over 6 hours. The amount of the hydrogen cyanide used was set at 1.0221 moles with respect to chlorine molecules. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted chlorine molecules disappeared (the inversion percentage of the chlorine was 99.9% or more). In addition, the ratio (A):(A)+(B) in the solution at the reaction terminal point was 0.04509:1. While the liquid temperature was kept at −5° C. to 0° C., 1029.5 g of dichloromethane and 1580.1 g of water were added to the present reaction solution, and the obtained solution was defined as solution 32. These results are shown in Table 1.

Example 16

1050 g (4.55 mol relative to OH group) of 1-naphthol aralkyl resin (manufactured by Nippon Steel & Sumikin Chemical Co., Ltd.) and 690.8 g (6.83 mol) of triethylamine (in an amount of 1.5 moles based on 1 mole of hydroxy group of the hydroxy group-substituted aromatic compound) were dissolved in 5775 g of dichloromethane, and the obtained solution was defined as solution 33. The solution 33 was added dropwise to the solution 32 (in which the amount of a cyanogen chloride was 1.51 moles based on 1 mole of hydroxy group of the hydroxy group-substituted aromatic compound) (cyanogen halide solution f) under stirring, while keeping the liquid temperature at −4° C. to −2° C., over 1.8 hours. After dropwise addition of the solution 33, the degree of reaction progress was 86.9%, and the dicyan concentration was 0.174% by mass. After completion of the dropwise addition of the solution 33, the reaction solution was stirred at the same temperature as described above for 30 minutes, and a solution prepared by dissolving 276.3 g (2.73 mol) of triethylamine (in an amount of 0.6 moles based on 1 mole of hydroxy group of the hydroxy group-substituted aromatic compound) in 276.3 g of dichloromethane (solution 34) was added dropwise to the reaction solution over 42 minutes. After dropwise addition of the solution 34, the degree of reaction progress was 98.5%, and the dicyan concentration was 0.217% by mass. After completion of the dropwise addition of the solution 34, the reaction solution was stirred at the same temperature as described above for 30 minutes. The pH of the reaction solution during the reaction was 0.55 or less. The degree of reaction progress in the production of a cyanate ester with respect to the amount of a basic compound used is shown in Table 2, and the concentration of dicyan as a by-product with respect to the amount of a basic compound used is shown in Table 3.

Thereafter, the reaction solution was left at rest, so that a dichloromethane phase was separated from a water phase. The obtained dichloromethane phase was washed with 3000 g of water six times. The electric conductivity of the waste water at the 6th water washing was 26 μS/cm, and thus, it was confirmed that an ionic compound to be removed was sufficiently removed by washing with water. After completion of the water washing, the dichloromethane phase was concentrated under reduced pressure, and the solvent was then replaced with a 2-butanone solution five times, to obtain 2325 g of a 2-butanone solution containing 50% by mass of a cyanate ester compound of interest. The concentration of hydrolyzable chlorine in the obtained cyanate ester compound was 25 ppm. These results are shown in Table 4. In addition, conditions for the cyanation step are shown in Table 5, and the content of a method of using a cyanogen halide is shown in Table 6.

Example 17

40 g (0.17 mol relative to OH group) of 1-naphthol aralkyl resin (manufactured by Nippon Steel & Sumikin Chemical Co., Ltd.) and 26.4 g (0.26 mol) of triethylamine (in an amount of 1.5 moles based on 1 mole of hydroxy group of the hydroxy group-substituted aromatic compound) were dissolved in 240 g of dichloromethane, and the obtained solution was defined as solution 35. 26.4 g of a 36%-by-mass aqueous solution of hydrochloric acid and 163.7 g of water were added to the solution 19 obtained in Example 9 (in which the amount of a cyanogen chloride was 1.5 moles based on 1 mole of hydroxy group of the hydroxy group-substituted aromatic compound), and the obtained solution was defined as solution 36 (cyanogen halide solution i). The solution 35 was added dropwise to the solution 36 under stirring, while keeping the liquid temperature at −7° C. to −2° C., over 14 minutes. After dropwise addition of the solution 35, the degree of reaction progress was 87.2%, and the dicyan concentration was 0.014% by mass. After completion of the dropwise addition of the solution 35, the reaction solution was stirred at the same temperature as described above for 30 minutes, and a solution prepared by dissolving 5.3 g (0.052 mol) of triethylamine (in an amount of 0.3 moles based on 1 mole of hydroxy group of the hydroxy group-substituted aromatic compound) in 5.3 g of dichloromethane (solution 36) was added dropwise to the reaction solution over 10 seconds. After dropwise addition of the solution 36, the degree of reaction progress was 99.2%, and the dicyan concentration was 0.015% by mass. The degree of reaction progress in the production of a cyanate ester with respect to the amount of a basic compound used is shown in Table 2, and the concentration of dicyan as a by-product with respect to the amount of a basic compound used is shown in Table 3. Moreover, conditions for the cyanation step are shown in Table 5, and the content of a method of using a cyanogen halide is shown in Table 6.

Example 18

473.7 g (6.68 mol) of chlorine (manufactured by Fujiox Co., Ltd.) was blown into 3586.4 g of a 5.2%-by-mass aqueous solution of hydrogen cyanide (hydrogen cyanide: 184.9 g (6.85 mol) and water: 3401.5 g) under stirring, while keeping the liquid temperature at −5° C. to 0° C., over 6 hours. The amount of the hydrogen cyanide used was set at 1.0251 moles with respect to chlorine molecules. The pH of the reaction solution was less than 7. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that unreacted chlorine molecules disappeared (the inversion percentage of the chlorine was 99.9% or more). In addition, the ratio (A):(A)+(B) in the solution at the reaction terminal point was 0.00335:1. While the liquid temperature was kept at 0° C. to 5° C., 998 g of dichloromethane and 1580.1 g of water were added to the present reaction solution, and then, the mixed solution was stirred and mixed. The reaction mixture was left at rest, so that a dichloromethane phase was physically separated from a water phase, to obtain a dichloromethane solution containing 23.3% cyanogen chloride. The obtained solution was defined as solution 37. These results are shown in Table 1.

Example 19

26.4 g of a 36%-by-mass aqueous solution of hydrochloric acid, 147.5 g of water, and 16.7 g of a 1.5% hydrogen cyanide solution were added to 68.8 g of the solution 37 (in which the amount of a cyanogen chloride was 1.5 moles based on 1 mole of hydroxy group of the hydroxy group-substituted aromatic compound), and the obtained solution was defined as solution 38 (wherein, at this stage, the ratio (A):(A)+(B) was 0.03351:1) (cyanogen halide solution i). The solution 35 obtained in Example 17 was added dropwise to the solution 38 under stirring, while keeping the liquid temperature at –7° C. to –1° C., over 15 minutes. After the dropwise addition of the solution 35, the degree of reaction progress was 79.9%, and the dicyan concentration was 0.124% by mass. After completion of the dropwise addition of the solution 35, the reaction solution was stirred at the same temperature as described above for 30 minutes, and a solution prepared by dissolving 7 g (0.07 mol) of triethylamine (in an amount of 0.4 moles based on 1 mole of hydroxy group of the hydroxy group-substituted aromatic compound) in 7 g of dichloromethane (solution 39) was added dropwise to the reaction solution over 20 seconds. After dropwise addition of the solution 39, the degree of reaction progress was 99.1%, and the dicyan concentration was 0.144% by mass. The degree of reaction progress in the production of a cyanate ester with respect to the amount of a basic compound used is shown in Table 2, and the concentration of dicyan as a by-product with respect to the amount of a basic compound used is shown in Table 3. Moreover, conditions for the cyanation step are shown in Table 5, and the content of a method of using a cyanogen halide is shown in Table 6.

Example 20

40 g (0.17 mol) of 1-naphthol aralkyl resin (manufactured by Nippon Steel & Sumikin Chemical Co., Ltd.) and 26.1 g (0.26 mol) of triethylamine (in an amount of 1.5 moles based on 1 mole of hydroxy group of the hydroxy group-substituted aromatic compound) were dissolved in 240 g of dichloromethane, and the obtained solution was defined as solution 40. 26.1 g of a 36%-by-mass aqueous solution of hydrochloric acid, 139.5 g of water, and 22.5 g of a 1.43%-by-mass hydrogen cyanide solution were added to the solution 37 obtained in Example 18 (in which the amount of a cyanogen chloride was 1.5 moles based on 1 mole of hydroxy group of the hydroxy group-substituted aromatic compound), and the obtained solution was defined as solution 41 (wherein, at this stage, the ratio (A):(A)+(B) was 0.04440:1) (cyanogen halide solution i). The solution 40 was added dropwise to the solution 41 under stirring, while keeping the liquid temperature at –7° C. to –2° C., over 14.5 minutes. After dropwise addition of the solution 40, the degree of reaction progress was 77.5%, and the dicyan concentration was 0.170% by mass. After completion of the dropwise addition of the solution 40, the reaction solution was stirred at the same temperature as described above for 30 minutes, and a solution prepared by dissolving 8.7 g (0.086 mol) of triethylamine (in an amount of 0.5 moles based on 1 mole of hydroxy group of the hydroxy group-substituted aromatic compound) in 8.7 g of dichloromethane (solution 42) was added dropwise to the reaction solution over 3.7 minutes. After dropwise addition of the solution 42, the degree of reaction progress was 97.4%, and the dicyan concentration was 0.196% by mass. After completion of the dropwise addition of the solution 42, the reaction solution was stirred at the same temperature as described above for 30 minutes, and a solution prepared by dissolving 2.6 g (0.026 mol) of triethylamine (in an amount of 0.15 moles based on 1 mole of hydroxy group of the hydroxy group-substituted aromatic compound) in 2.6 g of dichloromethane (solution 43) was added dropwise to the reaction solution over 1.7 minutes. After dropwise addition of the solution 43, the degree of reaction progress was 98.7%, and the dicyan concentration was 0.198% by mass. The degree of reaction progress in the production of a cyanate ester with respect to the amount of a basic compound used is shown in Table 2, and the concentration of dicyan as a by-product with respect to the amount of a basic compound used is shown in Table 3. Moreover, conditions for the cyanation step are shown in Table 5, and the content of a method of using a cyanogen halide is shown in Table 6.

Example 21

26.2 g of a 36%-by-mass aqueous solution of hydrochloric acid, 104.8 g of water, and 58.2 g of a 1.43%-by-mass hydrogen cyanide solution were added to the solution 37 obtained in Example 18 (in which the amount of a cyanogen chloride was 1.5 moles based on 1 mole of hydroxy group of the hydroxy group-substituted aromatic compound), and the obtained solution was defined as solution 44 (wherein, at this stage, the ratio (A):(A)+(B) was 0.10700:1) (cyanogen halide solution i). The solution 40 obtained in Example 20 was added dropwise to the solution 44 under stirring, while keeping the liquid temperature at –8° C. to –3° C., over 15 minutes. After dropwise addition of the solution 40, the degree of reaction progress was 71.6%, and the dicyan concentration was 0.384% by mass. After completion of the dropwise addition of the solution 40, the reaction solution was stirred at the same temperature as described above for 30 minutes, and a solution prepared by dissolving 8.7 g (0.086 mol) of triethylamine (in an amount of 0.5 moles based on 1 mole of hydroxy group of the hydroxy group-substituted aromatic compound) in 8.7 g of dichloromethane (solution 45) was added dropwise to the reaction solution over 4 minutes. After dropwise addition of the solution 45, the degree of reaction progress was 87.7%, and the dicyan concentration was 0.452% by mass. After completion of the dropwise addition of the solution 45, the reaction solution was stirred at the same temperature as described above for 30 minutes, and a solution prepared by dissolving 8.7 g (0.086 mol) of triethylamine (in an amount of 0.5 moles based on 1 mole of hydroxy group of the hydroxy group-substituted aromatic compound) in 8.7 g of dichloromethane (solution 46) was added dropwise to the reaction solution over 3.8 minutes. After dropwise addition of the solution 46, the degree of reaction progress was 97.3%, and the dicyan concentration was 0.482% by mass. After completion of the dropwise addition of the solution 46, the reaction solution was stirred at the same temperature as described above for 30 minutes, and a solution prepared by dissolving 2.6 g (0.026 mol) of triethylamine (in an amount of 0.15 moles based on 1 mole of hydroxy group of the hydroxy group-substituted aromatic compound) in 2.6 g of dichloromethane (solution 47) was added dropwise to the reaction solution over 1.6 minutes. After dropwise addition of the solution 47, the degree of reaction progress was 97.7%, and the dicyan concentration was 0.467% by mass. The degree of reaction progress in the production of a cyanate ester with respect to the amount of a basic compound used is shown in Table 2, and the concentration of dicyan as a by-product with respect to the amount of a basic compound used is shown in Table 3. Moreover, conditions for the cyanation step are shown in Table 5, and the content of a method of using a cyanogen halide is shown in Table 6.

Example 22

26.1 g of a 36%-by-mass aqueous solution of hydrochloric acid, 54.1 g of water, and 109.2 g of a 1.43% hydrogen cyanide solution were added to the solution 37 obtained in Example 18 (in which the amount of a cyanogen chloride was 1.5 moles based on 1 mole of hydroxy group of the hydroxy group-substituted aromatic compound), and the obtained solution was defined as solution 48 (wherein, at this stage, the ratio (A):(A)+(B) was 0.18378:1) (cyanogen halide solution i). The solution 40 obtained in Example 20 was added dropwise to the solution 48 under stirring, while keeping the liquid temperature at −7° C. to −2° C., over 14.5 minutes. After dropwise addition of the solution 40, the degree of reaction progress was 71.2%, and the dicyan concentration was 0.390% by mass. After completion of the dropwise addition of the solution 40, the reaction solution was stirred at the same temperature as described above for 30 minutes, and a solution prepared by dissolving 8.7 g (0.086 mol) of triethylamine (in an amount of 0.5 moles based on 1 mole of hydroxy group of the hydroxy group-substituted aromatic compound) in 8.7 g of dichloromethane (solution 49) was added dropwise to the reaction solution over 4 minutes. After dropwise addition of the solution 49, the degree of reaction progress was 87.0%, and the dicyan concentration was 0.458% by mass. After completion of the dropwise addition of the solution 49, the reaction solution was stirred at the same temperature as described above for 30 minutes, and a solution prepared by dissolving 8.7 g (0.086 mol) of triethylamine (in an amount of 0.5 moles based on 1 mole of hydroxy group of the hydroxy group-substituted aromatic compound) in 8.7 g of dichloromethane (solution 50) was added dropwise to the reaction solution over 3.8 minutes. After dropwise addition of the solution 50, the degree of reaction progress was 97.0%, and the dicyan concentration was 0.492% by mass. After completion of the dropwise addition of the solution 50, the reaction solution was stirred at the same temperature as described above for 30 minutes, and a solution prepared by dissolving 3.5 g (0.034 mol) of triethylamine (in an amount of 0.2 moles based on 1 mole of hydroxy group of the hydroxy group-substituted aromatic compound) in 3.5 g of dichloromethane (solution 51) was added dropwise to the reaction solution over 2 minutes. After dropwise addition of the solution 51, the degree of reaction progress was 98.5%, and the dicyan concentration was 0.497% by mass. The degree of reaction progress in the production of a cyanate ester with respect to the amount of a basic compound used is shown in Table 2, and the concentration of dicyan as a by-product with respect to the amount of a basic compound used is shown in Table 3. Moreover, conditions for the cyanation step are shown in Table 5, and the content of a method of using a cyanogen halide is shown in Table 6.

Comparative Example 5

26.4 g of a 36%-by-mass aqueous solution of hydrochloric acid and 166.8 g of a 1.5%-by-mass hydrogen cyanide solution were added to the solution 37 obtained in Example 18 (in which the amount of a cyanogen chloride was 1.5 moles based on 1 mole of hydroxy group of the hydroxy group-substituted aromatic compound), and the obtained solution was defined as solution 52 (wherein, at this stage, the ratio (A):(A)+(B) was 0.26217:1) (cyanogen halide solution i). The solution 35 obtained in Example 17 was added dropwise to the solution 52 under stirring, while keeping the liquid temperature at −7° C. to −0° C., over 14 minutes. After dropwise addition of the solution 35, the degree of reaction progress was 51.3%, and the dicyan concentration was 0.905% by mass. After completion of the dropwise addition of the solution 35, the reaction solution was stirred at the same temperature as described above for 30 minutes, and a solution prepared by dissolving 8.8 g (0.087 mol) of triethylamine (in an amount of 0.5 moles based on 1 mole of hydroxy group of the hydroxy group-substituted aromatic compound) in 8.8 g of dichloromethane (solution 53) was added dropwise to the reaction solution over 35 seconds. After dropwise addition of the solution 53, the degree of reaction progress was 65.2%, and the dicyan concentration was 1.070% by mass. After completion of the dropwise addition of the solution 53, the reaction solution was stirred at the same temperature as described above for 30 minutes, and a solution prepared by dissolving 8.8 g (0.087 mol) of triethylamine (in an amount of 0.5 moles based on 1 mole of hydroxy group of the hydroxy group-substituted aromatic compound) in 8.8 g of dichloromethane (solution 54) was added dropwise to the reaction solution over 30 seconds. After dropwise addition of the solution 54, the degree of reaction progress was 77.9%, and the dicyan concentration was 1.243% by mass. After completion of the dropwise addition of the solution 54, the reaction solution was stirred at the same temperature as described above for 30 minutes, and a solution prepared by dissolving 17.6 g (0.176 mol) of triethylamine (in an amount of 1.0 mole based on 1 mole of hydroxy group of the hydroxy group-substituted aromatic compound) in 17.6 g of dichloromethane (solution 55) was added dropwise to the reaction solution over 30 seconds. After dropwise addition of the solution 55, the degree of reaction progress was 99.1%, and the dicyan concentration was 1.579% by mass. The degree of reaction progress in the production of a cyanate ester with respect to the amount of a basic compound used is shown in Table 2, and the concentration of dicyan as a by-product with respect to the amount of a basic compound used is shown in Table 3. Moreover, conditions for the cyanation step are shown in Table 5, and the content of a method of using a cyanogen halide is shown in Table 6.

TABLE 1

Cyanogen halide-production step

| | Addition of substance Hydrogen cyanide or sodium cyanide (with respect to halogen molecule) Molar ratio | Terminal point (A) : (A) + (B) Molar ratio | Color *1 | Post-treatment | Additive |
|---|---|---|---|---|---|
| Example 1 | 1.0153 | 0.02100:1 | Colorless | Dichloromethane | — |
| Example 3 | 1.0088 | 0.02174:1 | Colorless | Dichloromethane | Water |
| Example 5 | 1.0091 | 0.00645:1 | Colorless | Chloroform | — |
| Example 7 | 1.0091 | 0.00645:1 | Colorless | Chloroform | — |
| Example 9 | 1.0336 | 0.00641:1 | Colorless | Dichloromethane | Water |
| Example 11 | 1.0768 | 0.00884:1 | Colorless | Dichloromethane | — |
| Comparative Example 1 | 0.9478 | Unreacted hydrogen cyanide is not present | Yellow | Dichloromethane | — |
| Comparative Example 3 | 0.9478 | Unreacted hydrogen cyanide is not present | Yellow | Dichloromethane | — |
| Example 13 | 1.0533 | 0.01891:1 | Colorless | Dichloromethane | Water |
| Example 15 | 1.0221 | 0.04509:1 | Colorless | Dichloromethane | Water |
| Example 18 | 1.0251 | 0.00335:1 | Colorless | Dichloromethane | Water |

*1: The color of a dichloromethane phase obtained after the reaction solution (40 g) at the terminal point was added to a water/dichloromethane solution (15 g/10 g) that had previously been prepared and cooled to 5° C., and an extraction operation was then performed on the obtained mixture.

Degree of Reaction Progress in Cyanation Step (Unit: %)

TABLE 2

| | Used amount of basic compound based on 1 mole of hydroxy group in hydroxy group-substituted aromatic compound | | | | | | | | | | | | |
|---|---|---|---|---|---|---|---|---|---|---|---|---|---|
| | 1.15 molar ratio | 1.5 molar ratio | 1.67 molar ratio | 1.8 molar ratio | 1.9 molar ratio | 2.0 molar ratio | 2.04 molar ratio | 2.1 molar ratio | 2.15 molar ratio | 2.5 molar ratio | 2.65 molar ratio | 2.7 molar ratio | 3.5 molar ratio |
| Example 2 | — | 80.6 | — | — | — | 99.5 | — | — | — | — | — | — | — |
| Example 4 | — | — | — | 37.1 | — | — | — | — | — | 95.3 | — | 99.6 | — |
| Example 6 | — | — | — | — | 98.7 | — | — | — | — | — | — | — | — |
| Example 10 | — | — | 94.9 | — | — | — | — | — | — | — | — | — | — |
| Example 12 | 98.5 | — | — | — | — | — | — | — | — | — | — | — | — |
| Comparative Example 2 | — | 83.9 | — | — | 97.7 | — | — | — | 98.8 | — | — | — | — |
| Comparative Example 4 | 97.9 | — | — | — | — | — | — | — | — | — | — | — | — |
| Example 14 | — | 85.6 | — | — | — | — | 98.7 | — | — | — | — | — | — |
| Example 16 | — | 86.9 | — | — | — | — | — | 98.5 | — | — | — | — | — |
| Example 17 | — | 87.2 | — | 99.2 | — | — | — | — | — | — | — | — | — |
| Example 19 | — | 79.9 | — | — | 99.1 | — | — | — | — | — | — | — | — |
| Example 20 | — | 77.5 | — | — | — | 97.4 | — | — | 98.7 | — | — | — | — |
| Example 21 | — | 71.6 | — | — | — | 87.7 | — | — | — | 97.3 | 97.7 | — | — |
| Example 22 | — | 71.2 | — | — | — | 87.0 | — | — | — | 97.0 | — | 98.5 | — |
| Comparative Example 5 | — | 51.3 | — | — | — | 65.2 | — | — | — | 77.9 | — | — | 99.1 |

Concentration of Dicyan in Cyanation Step (Unit: % by Mass)

TABLE 3

| | Used amount of basic compound based on 1 mole of hydroxy group in hydroxy group-substituted aromatic compound | | | | | | | | | | |
|---|---|---|---|---|---|---|---|---|---|---|---|
| | 1.5 molar ratio | 1.8 molar ratio | 1.9 molar ratio | 2.0 molar ratio | 2.04 molar ratio | 2.1 molar ratio | 2.15 molar ratio | 2.5 molar ratio | 2.65 molar ratio | 2.7 molar ratio | 3.5 molar ratio |
| Example 2 | 0.071 | — | — | 0.075 | — | — | — | — | — | — | — |
| Example 14 | 0.069 | — | — | — | 0.087 | — | — | — | — | — | — |

TABLE 3-continued

Used amount of basic compound based on 1 mole of hydroxy group in hydroxy group-substituted aromatic compound

|  | 1.5 molar ratio | 1.8 molar ratio | 1.9 molar ratio | 2.0 molar ratio | 2.04 molar ratio | 2.1 molar ratio | 2.15 molar ratio | 2.5 molar ratio | 2.65 molar ratio | 2.7 molar ratio | 3.5 molar ratio |
|---|---|---|---|---|---|---|---|---|---|---|---|
| Example 16 | 0.174 | — | — | — | — | 0.217 | — | — | — | — | — |
| Example 17 | 0.014 | 0.015 | — | — | — | — | — | — | — | — | — |
| Example 19 | 0.124 | — | 0.144 | — | — | — | — | — | — | — | — |
| Example 20 | 0.170 | — | — | 0.196 | — | — | 0.198 | — | — | — | — |
| Example 21 | 0.384 | — | — | 0.452 | — | — | — | 0.467 | 0.482 | — | — |
| Example 22 | 0.390 | — | — | 0.458 | — | — | — | 0.492 | — | 0.497 | — |
| Comparative Example 5 | 0.905 | — | — | 1.070 | — | — | — | 1.243 | — | — | 1.579 |

TABLE 4

Analysis results of obtained cyanate ester compounds

|  | Hydrolyzable halogen ppm | Total halogen ppm | Gelatinization time 1 min | Gelatinization time 2 min |
|---|---|---|---|---|
| Example 2 | 23 | 141 | 68 | 12.9 |
| Example 4 | 40 | — | — | — |
| Example 6 | 25 | — | — | — |
| Example 8 | 30 | — | — | — |
| Example 10 | 35 | — | — | — |
| Example 12 | — | 52 | — | — |
| Example 14 | 21 | — | — | — |
| Example 16 | 25 | — | — | — |
| Comparative Example 2 | 2156 | 4500 | 27 | 9.5 |
| Comparative Example 4 | — | 793 | — | — |

TABLE 5

Cyanation step
Just before the cyanation step

|  | On cyanogen halide solution side | Additive | (A) : (A) + (B) Molar ratio | Method of using cyanogen halide *2 |
|---|---|---|---|---|
| Example 2 | — | — | 0.02100:1 | e |
| Example 4 | — | — | 0.02174:1 | f |
| Example 6 | — | — | 0.00645:1 | g |
| Example 8 | Tetrahydrofuran | Tris(4-hydroxyphenyl)methane | 0.00645:1 | h |
| Example 10 | — | — | 0.00456:1 | g |
| Example 12 | — | — | 0.00658:1 | g |
| Comparative Example 2 | — | — | — | e |
| Comparative Example 4 | — | — | — | g |
| Example 14 | — | — | 0.01891:1 | f |
| Example 16 | — | — | 0.04509:1 | f |
| Example 17 | Hydrochloric acid solution | — | 0.00455:1 | i |
| Example 19 | Hydrochloric acid solution | Hydrogen cyanide solution | 0.03351:1 | i |
| Example 20 | Hydrochloric acid solution | Hydrogen cyanide solution | 0.04440:1 | i |
| Example 21 | Hydrochloric acid solution | Hydrogen cyanide solution | 0.10700:1 | i |
| Example 22 | Hydrochloric acid solution | Hydrogen cyanide solution | 0.18378:1 | i |
| Comparative Example 5 | Hydrochloric acid solution | Hydrogen cyanide solution | 0.26217:1 | i |

TABLE 6

| *2 | Method of using cyanogen halide | Solvent |
|---|---|---|
| d | Aqueous solution of cyanogen halide obtained after reaction in first step | Aqueous system |
| e | Solution obtained by adding organic solvent to d | Organic solvent/water, two-phase system |
| f | Solution obtained by adding organic solvent and water to d | Organic solvent/water, two-phase system |
| g | Cyanogen halide organic solvent solution obtained by extracting cyanogen halide from d with organic solvent | Organic solvent system |
| h | Solution obtained by adding organic solvent to g | Organic solvent system |
| i | Solution obtained by adding organic solvent + water or water to g | Organic solvent/water, two-phase system |

In Comparative Examples 1 and 3, since the reaction was carried out in the cyanogen halide-producing step, using hydrogen cyanide, the amount of which did not exceed 1 mole based on 1 mole of chlorine molecules, unreacted chlorine remained. Further, the cyanate ester compounds produced using such cyanogen halide (Comparative Examples 2 and 4) each contained halogen compounds that were hardly removed even by washing with water or the like. Thus, it was revealed that these compounds would accelerate the polymerization reaction during thermal hardening.

In Comparative Example 5, a cyanate ester compound was produced in a state in which the ratio of (A):(A)+(B) was not between 0.00009:1 and 0.2:1 immediately before the cyanation step. Thus, it was revealed that cyanogen halide was lost by the reaction of unreacted hydrogen cyanide with cyanogen halide (subgeneration of dicyan), and thus that the efficiency of the reaction of producing cyanate ester was significantly reduced (namely, the amount of a basic compound used was significantly increased).

(Measurement of Weight-Average Molecular Weight Mw of Cyanate Ester Compound)

A solution (10 μL) prepared by dissolving 1 g of a cyanate ester compound in 100 g of tetrahydrofuran (solvent) was injected into high performance liquid chromatography (manufactured by Hitachi High-Technologies Corporation, high performance liquid chromatograph LachromElite), and the analysis was then carried out. As columns, two columns of TSK gel GMH$_{HR}$-M (30 cm in length×7.8 mm in inner diameter) manufactured by Tosoh Corporation were used, and as a mobile phase, tetrahydrofuran was used. The flow rate was set at 1 mL/min., and the detector was RI. The weight-average molecular weight Mw was obtained according to a GPC method using polystyrene as a standard substance.

(Sample 1)

Synthesis of a cyanate ester compound of a phenolic resin having, as a representative composition, a polynaphthylene ether structure represented by the following general formula (26) (hereinafter also referred to as "NECN")

[Formula 42]

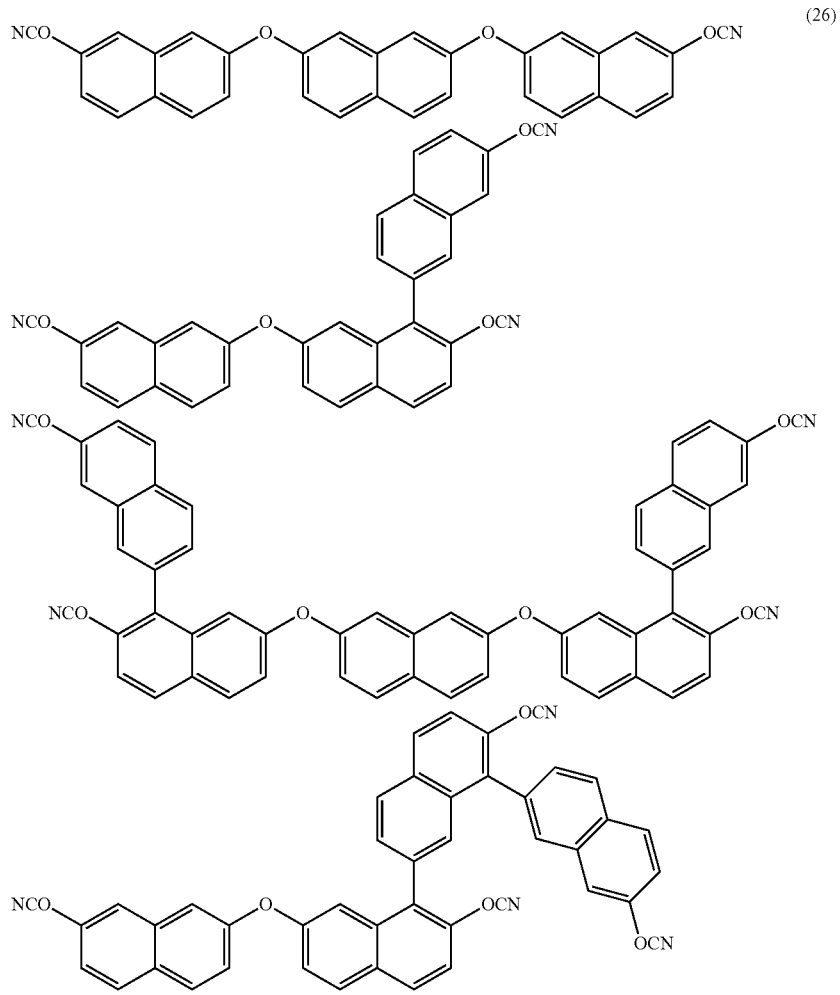

<Synthesis of Phenolic Resin Having Polynaphthylene Ether Structure>

According to the production method described in Example 5 of Japanese Patent No. 4259536, a phenolic resin having a polynaphthylene ether structure (brown solid) was obtained from 2,7-dihydroxynaphthalene. The OH value of the obtained phenolic resin was 361 mgKOH/g wherein the OH group equivalent was 155 g/eq. In addition, the weight-average molecular weight Mw was 370. The GPC chart is shown in FIG. 1.

<Synthesis of Cyanogen Halide>

368.7 g (5.20 mol) of chlorine (manufactured by Fujiox Co., Ltd.) was blown into 2791.9 g of a 5.2%-by-mass aqueous solution of hydrogen cyanide (hydrogen cyanide: 143.9 g (5.33 mol) and water: 2648 g) under stirring, while keeping the liquid temperature at −5° C. to 0° C., over 4.6 hours. Hydrogen cyanide was used in an amount of 1.0251 moles with respect to chlorine molecules. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that no unreacted chlorine molecules were present (the inversion percentage of the chlorine was 99.9% or more). In addition, the ratio (A):(A)+(B) in the solution at the reaction terminal point was 0.00335:1. While the liquid temperature was kept at 0° C. to 5° C., 753 g of dichloromethane and 1191.6 g of water were added to the solution after completion of the reaction, and the obtained solution was defined as solution 56.

<Synthesis of NECN>

380 g (2.45 mol relative to OH group) of the phenolic resin having a polynaphthylene ether structure obtained by the above described method and 372.1 g (3.68 mol) of triethylamine (in an amount of 1.5 moles based on 1 mole of hydroxy group of the phenolic resin) were dissolved in 2280 g of dichloromethane, and the obtained solution was defined as solution 57.

The solution 57 was added dropwise to the solution 56 (in which the amount of a cyanogen chloride was 2.1 moles based on 1 mole of hydroxy group of the phenolic resin) (cyanogen halide solution e) under stirring, while keeping the liquid temperature at −2° C. to −0.5° C., over 50 minutes. After completion of the dropwise addition of the solution 57, the reaction solution was stirred at the same temperature as described above for 30 minutes, and a solution prepared by dissolving 297.7 g (2.94 mol) of triethylamine (in an amount of 1.2 moles based on 1 mole of hydroxy group of the phenolic resin) in 298 g of dichloromethane (solution 58) was added dropwise to the reaction solution over 30 minutes. After completion of the dropwise addition of the solution 58, the reaction solution was stirred at the same temperature as described above for 30 minutes, and the reaction was then terminated.

Thereafter, the reaction solution was left at rest, so that a dichloromethane phase was separated from a water phase. The obtained dichloromethane phase was washed with 2000 g of water six times. The electric conductivity of the waste water at the 5th water washing was 20 μS/cm, and thus, it was confirmed that an ionic compound to be removed was sufficiently removed by washing with water.

Figure 2:
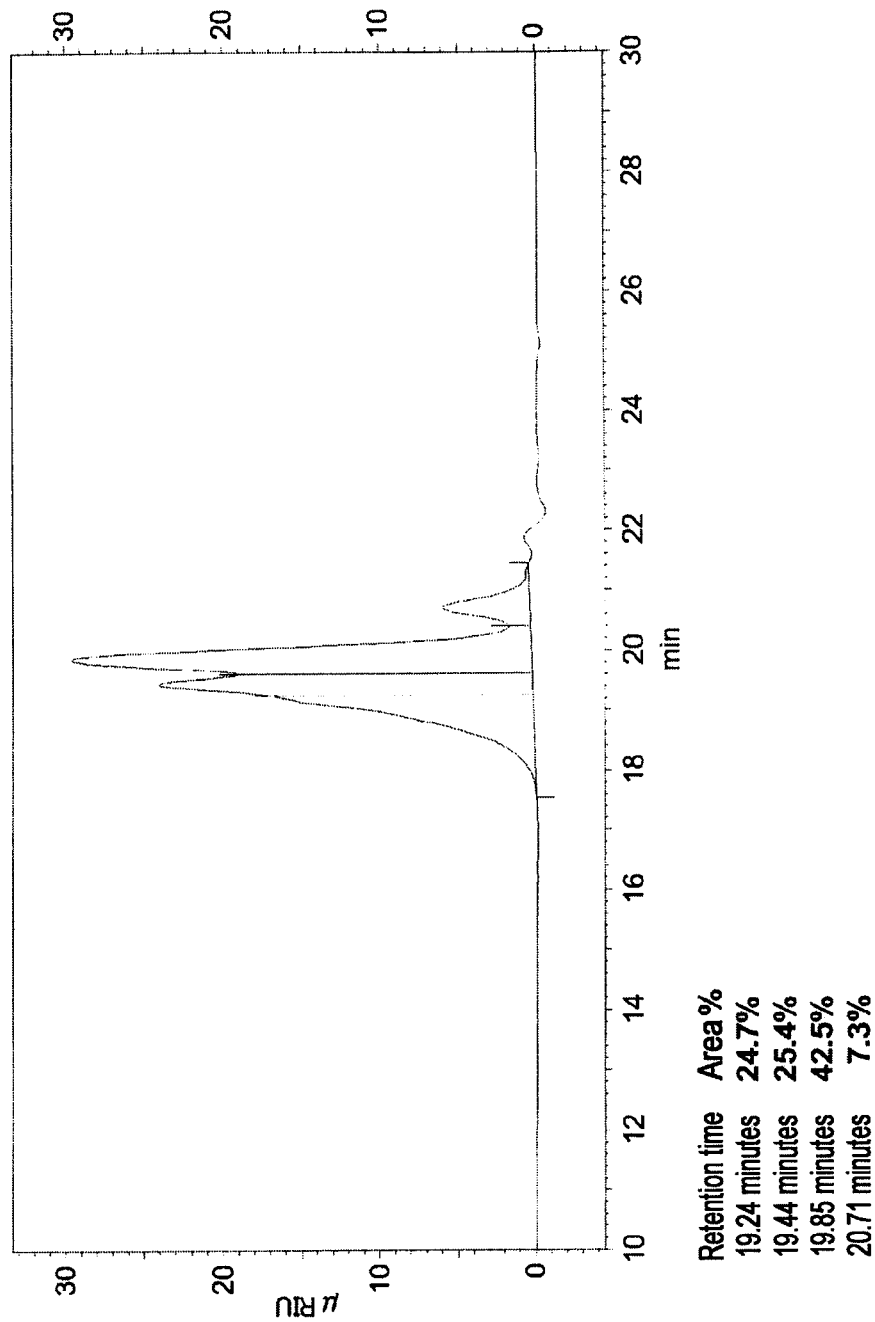
FIG. 2 shows a GPC chart of the cyanate ester compound NECN obtained in Sample 1.
Figure 3:
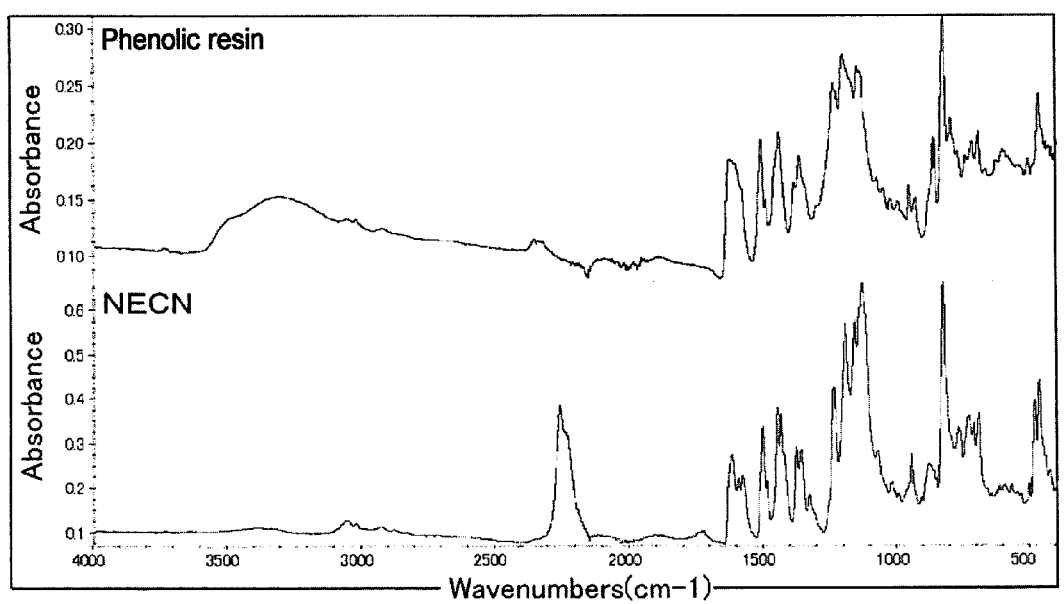
FIG. 3 shows an FT-IR chart of the phenolic resin and cyanate ester compound NECN obtained in Sample 1.

After completion of the water washing, the dichloromethane phase was concentrated under reduced pressure, and finally, it was concentrated and dried at 90° C. for 1 hour to obtain 390 g of the cyanate ester compound NECN (brown viscous product) of interest. The weight-average molecular weight Mw of the obtained cyanate ester compound NECN was 320. The GPC chart is shown in FIG. 2. In addition, the IR spectrum of NEON exhibited absorption of 2263 cm$^{-1}$ (cyanate ester group) and did not exhibit the absorption of hydroxy group. The IR chart is shown in FIG. 3.

(Sample 2)

Synthesis of a cyanate ester compound of a naphthol-modified meta-xylene glycol resin represented by the following general formula (27) (hereinafter also referred to as "SNCN-MX")

[Formula 43]

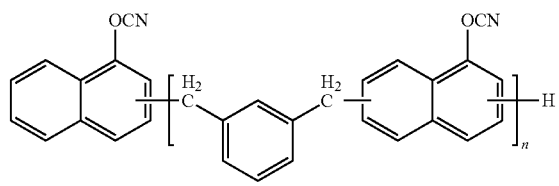

(27)

wherein n represents an integer of 1 to 50.

<Synthesis of Naphthol-Modified Meta-Xylene Glycol Resin>

Figure 4:
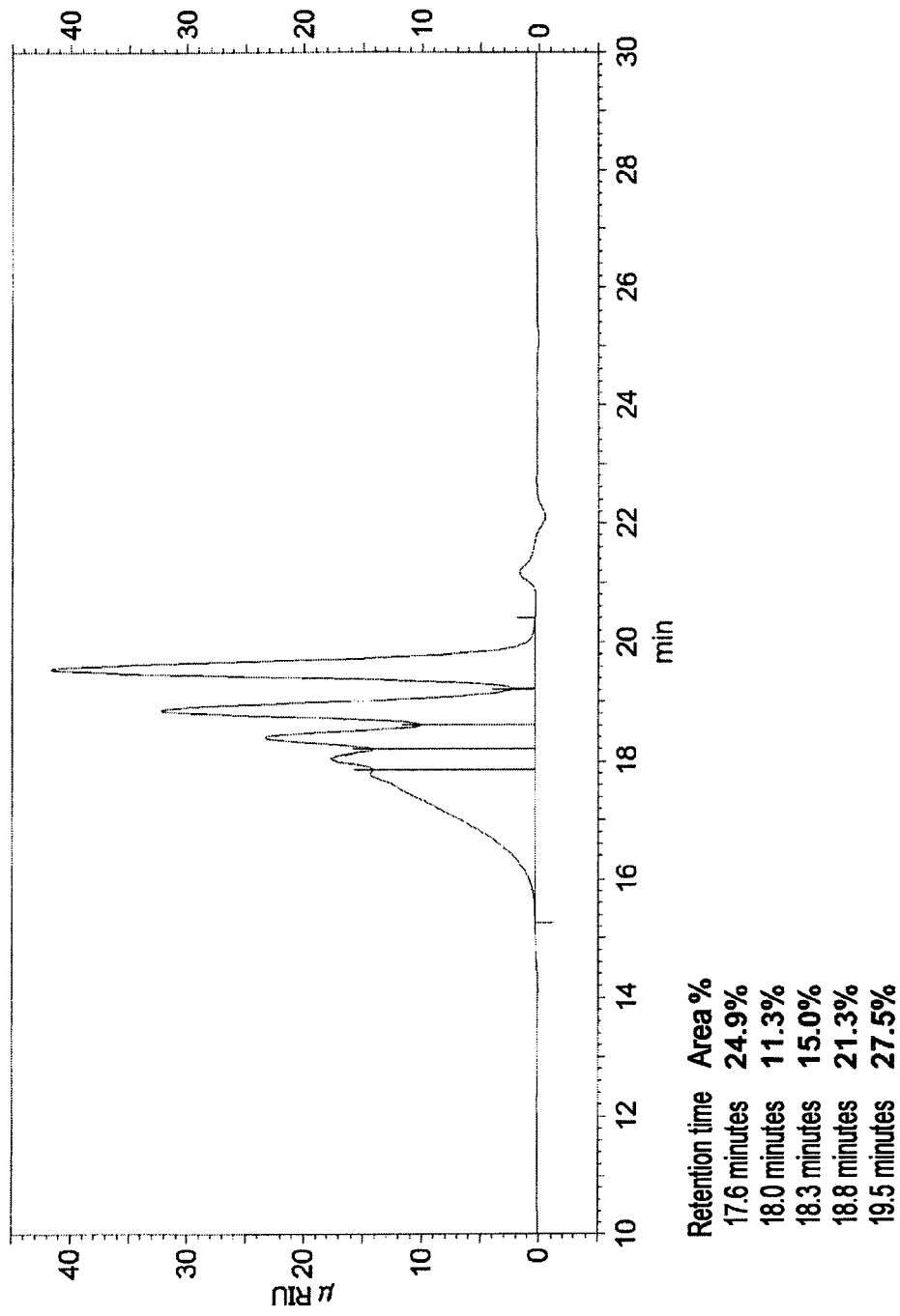
FIG. 4 shows a GPC chart of the naphthol-modified meta-xylene glycol resin obtained in Sample 2.

420.0 g (3.04 mol) of meta-xylene glycol and 876.5 g (6.08 mol) of 1-naphthol were added into a four-necked flask (internal volume: 2 L) equipped with a Liebig condenser, a thermometer and an impeller under a nitrogen current, and the obtained mixture was then melted by heating at 90° C. After that, while stirring, 260 mg (1.51 mmol) of p-toluenesulfonic acid was added to the reaction mixture, and the reaction was then carried out for 3 hours, while the temperature was increased to 170° C. Thereafter, the reaction product was neutralized and washed with water, and unreacted raw materials were then removed under reduced pressure, to obtain 945 g of a naphthol-modified meta-xylene glycol resin. The OH group equivalent of the obtained resin was 220 g/eq. In addition, the weight-average molecular weight Mw was 820. The GPC chart is shown in FIG. 4.

<Synthesis of Cyanogen Halide>

375.0 g (5.29 mol) of chlorine (manufactured by Fujiox Co., Ltd.) was blown into 2839.6 g of a 5.2%-by-mass aqueous solution of hydrogen cyanide (hydrogen cyanide: 146.4 g (5.42 mol) and water: 2693.2 g) under stirring, while keeping the liquid temperature at −5° C. to 0° C., over 4.7 hours. Hydrogen cyanide was used in an amount of 1.0251 moles with respect to chlorine molecules. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that no unreacted chlorine molecules were present (the inversion percentage of the chlorine was 99.9% or more). In addition, the ratio (A):(A)+(B) in the solution at the reaction terminal point was 0.00335:1. While the liquid temperature was kept at 0° C. to 5° C., 765 g of dichloromethane and 1211.9 g of water were added to the present reaction solution, and the obtained solution was defined as solution 59.

<Synthesis of SNCN-MX>

720 g (3.27 mol relative to OH group) of the naphthol-modified meta-xylene glycol resin obtained by the above described method and 496.8 g (4.91 mol) of triethylamine (in an amount of 1.5 moles based on 1 mole of hydroxy group of the naphthol-modified meta-xylene glycol resin)

were dissolved in 3960 g of dichloromethane, and the obtained solution was defined as solution 60.

The solution 60 was added dropwise to the solution 59 (in which the amount of a cyanogen chloride was 2.1 moles based on 1 mole of hydroxy group of the naphthol-modified meta-xylene glycol resin) (cyanogen halide solution e in Table 6) under stirring, while keeping the liquid temperature at −2° C. to −0.5° C., over 75 minutes. After completion of the dropwise addition of the solution 60, the reaction solution was stirred at the same temperature as described above for 30 minutes, and a solution prepared by dissolving 132.47 g (1.31 mol) of triethylamine (in an amount of 0.4 moles based on 1 mole of hydroxy group of the naphthol-modified meta-xylene glycol resin) in 132.5 g of dichloromethane (solution 61) was added dropwise to the reaction solution over 30 minutes. After completion of the dropwise addition of the solution 61, the reaction solution was stirred at the same temperature as described above for 30 minutes, and the reaction was then terminated.

Thereafter, the reaction solution was left at rest, so that a dichloromethane phase was separated from a water phase. The obtained dichloromethane phase was washed with 2000 g of water five times. The electric conductivity of the waste water at the 5th water washing was 20 μS/cm, and thus, it was confirmed that an ionic compound to be removed was sufficiently removed by washing with water.

Figure 5:
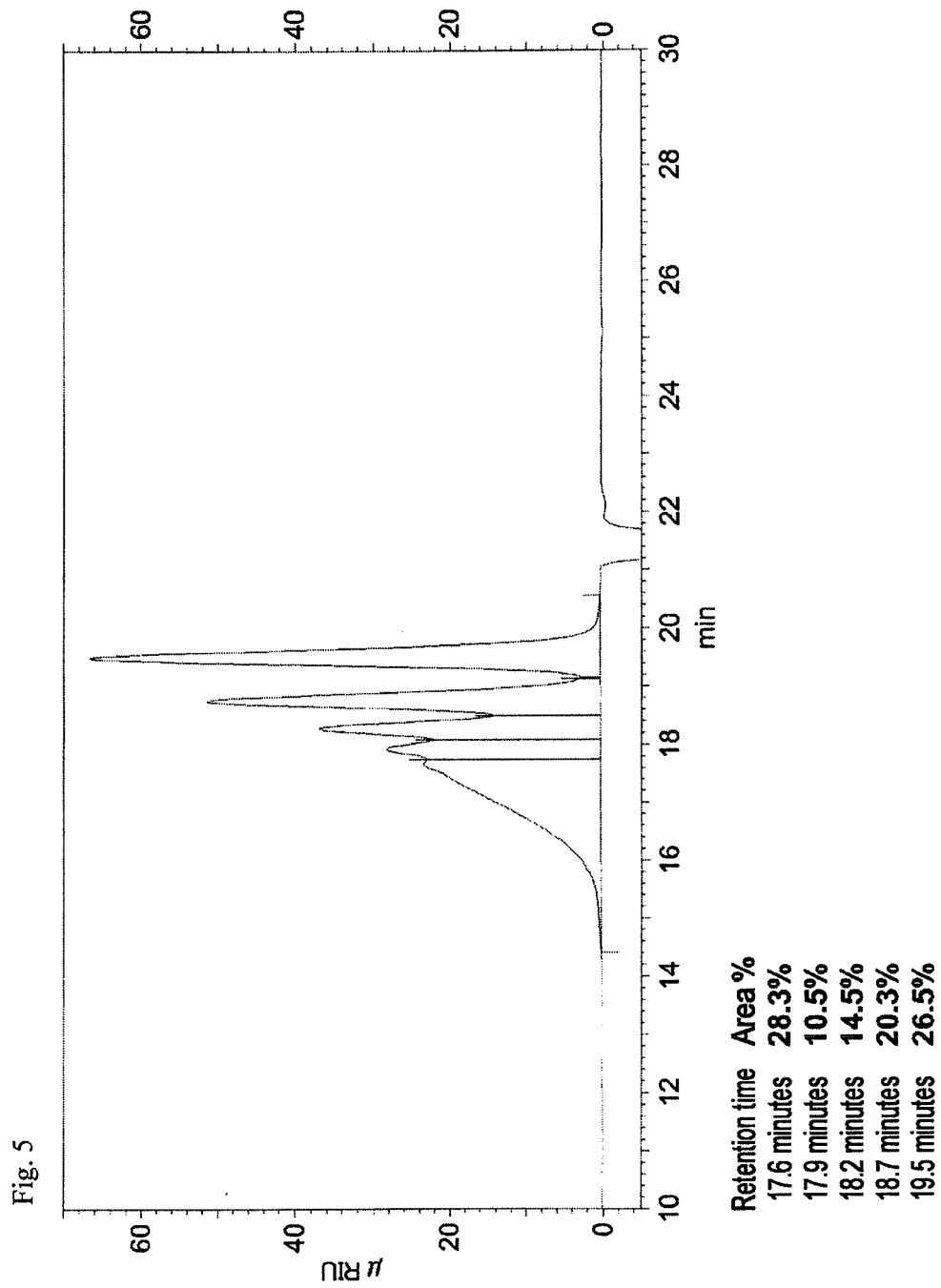
FIG. 5 shows a GPC chart of the cyanate ester compound of the naphthol-modified meta-xylene glycol resin obtained in Sample 2.
Figure 6:
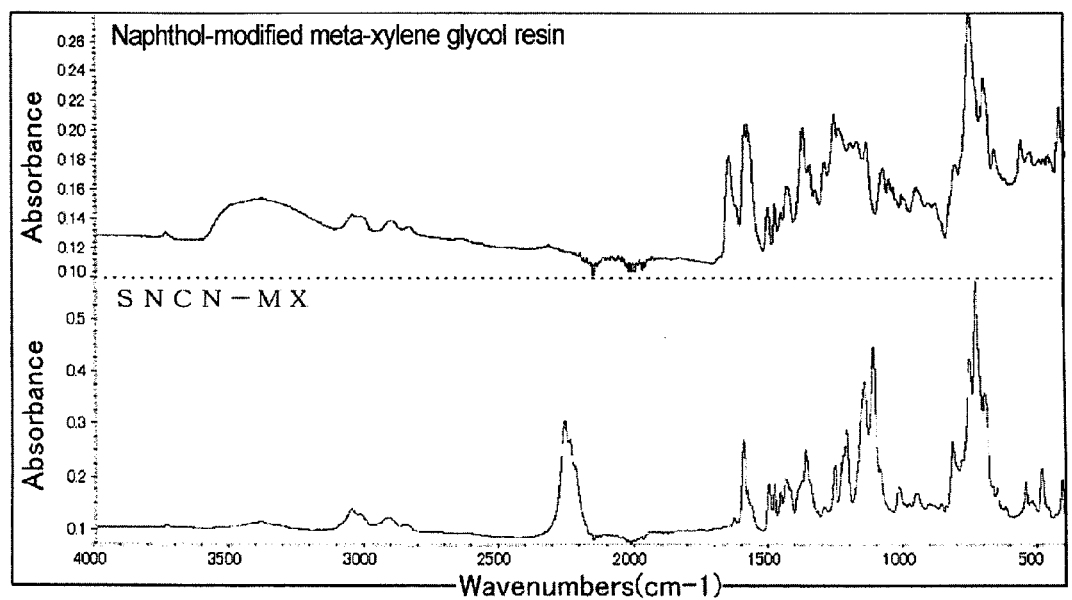
FIG. 6 shows an IR chart of the cyanate ester compound of the naphthol-modified meta-xylene glycol resin obtained in Sample 2.

After completion of the water washing, the dichloromethane phase was concentrated under reduced pressure, and finally, it was concentrated and dried at 90° C. for 1 hour to obtain 777 g of the cyanate ester compound SNCN-MX (orange viscous product) of interest. The weight-average molecular weight Mw of the obtained cyanate ester compound SNCN-MX was 1040. The GPC chart is shown in FIG. 5. In addition, the IR spectrum of SNCN-MX exhibited absorption of 2250 cm$^{-1}$ (cyanate ester group) and did not exhibit the absorption of hydroxy group. The IR chart is shown in FIG. 6.

(Sample 3)

Synthesis of 1,3-bis(4-cyanatophenyl)-5,7-dimethyladamantane (formula (28)) (hereinafter also referred to as "AMTCN")

[Formula 44]

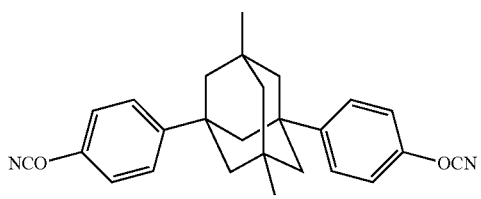

(28)

<Synthesis of 1,3-Bis(4-Hydroxyphenyl)-5,7-Dimethyladamantane (Hereinafter Also Referred to as "AMTOH")>

166.0 g (0.85 mol) of 5,7-dimethyladamantane-1,3-diol and 644.4 g (6.85 mol) of phenol were added into a reaction system under a nitrogen current, and the obtained mixture was then melted by heating at 80° C. Then, while stirring, 81.5 g (0.85 mol) of methanesulfonic acid was added to the reaction mixture. Thereafter, the temperature was increased to 100° C., and the reaction was then carried out for 4 hours. Subsequently, 600 mL of water and 300 mL of methanol were added to the reaction solution, and the obtained mixture was then cooled to 4° C. in an ice bath. The reaction mixture was stirred at the same temperature as described above for 1 hour. Thereafter, a precipitate was collected by filtration, and the obtained crystal was repeatedly washed with 500 mL of hot water at 70° C. four times. After washing, the crystal was dissolved in 1100 mL of ethyl acetate+500 mL of toluene. The thus obtained solution was washed with 500 mL of a 0.5%-by-mass NaOH aqueous solution three times, and thereafter, washing with 500 mL of water was repeatedly carried out until the pH of the water phase became neutral. After completion of the water washing, the dichloromethane phase was concentrated and dried under reduced pressure to obtain a solid. The obtained solid was dissolved in 1000 mL of ethyl acetate at 70° C. To the obtained solution, 2000 mL of heptane was added at room temperature, and the obtained mixture was then stirred for 10 minutes to obtain a precipitate. The precipitate was collected by filtration, and it was then washed with 600 mL of heptane twice. Finally, the resultant was dried at 90° C. for 14 hours, to obtain 183.5 g of 1,3-bis(4-hydroxyphenyl)-5,7-dimethyladamantane (white solid).

<Synthesis of Cyanogen Halide>

384.3 g (5.42 mol) of chlorine (manufactured by Fujiox Co., Ltd.) was blown into 2909.8 g of a 5.2%-by-mass aqueous solution of hydrogen cyanide (hydrogen cyanide: 150.0 g (5.56 mol) and water: 2759.8 g) under stirring, while keeping the liquid temperature at −5° C. to 0° C., over 4.8 hours. Hydrogen cyanide was used in an amount of 1.0251 moles with respect to chlorine molecules. The reaction solution (40 g) obtained at the reaction terminal point was added to a water/dichloromethane solution (15 g/10 g) cooled to 5° C., which had been prepared separately in advance, and the obtained mixture was then subjected to an extraction operation. As a result, both the dichloromethane phase and the water phase were colorless, and thus, it was confirmed that no unreacted chlorine molecules were present (the inversion percentage of the chlorine was 99.9% or more). In addition, the ratio (A):(A)+(B) in the solution at the reaction terminal point was 0.00335:1. While the liquid temperature was kept at 0° C. to 5° C., 784 g of dichloromethane and 1241.9 g of water were added to the present reaction solution, and the obtained solution was defined as solution 62.

<Synthesis of AMTCN>

550 g (3.16 mol relative to OH group) of the 1,3-bis(4-hydroxyphenyl)-5,7-dimethyladamantane obtained by the above described method and 319.3 g (3.16 mol) of triethylamine (in an amount of 1.0 mole based on 1 mole of hydroxy group of the AMTOH) were dissolved in 3300 g of dichloromethane, and the obtained solution was defined as solution 63.

The solution 63 was added dropwise to the solution 62 (in which the amount of a cyanogen chloride was 1.7 moles based on 1 mole of hydroxy group of the AMTOH) (cyanogen halide solution e) under stirring, while keeping the liquid temperature at −2° C. to −0.5° C., over 82 minutes. After completion of the dropwise addition of the solution 63, the reaction solution was stirred at the same temperature as described above for 30 minutes, and a solution prepared by dissolving 319.3 g (3.16 mol) of triethylamine (in an amount of 1.0 mole based on 1 mole of hydroxy group of the AMTOH) in 319.3 g of dichloromethane (solution 64) was added dropwise to the reaction solution over 42 minutes. After completion of the dropwise addition of the solution 64, the reaction solution was stirred at the same temperature as described above for 30 minutes, and the reaction was then terminated.

Thereafter, the reaction solution was left at rest, so that a dichloromethane phase was separated from a water phase.

The obtained dichloromethane phase was washed with 2000 g of 0.1 N hydrochloric acid, and then with 2000 g of water five times. The electric conductivity of the waste water at the 5th water washing was 20 μS/cm, and thus, it was confirmed that an ionic compound to be removed was sufficiently removed by washing with water.

Figure 7:
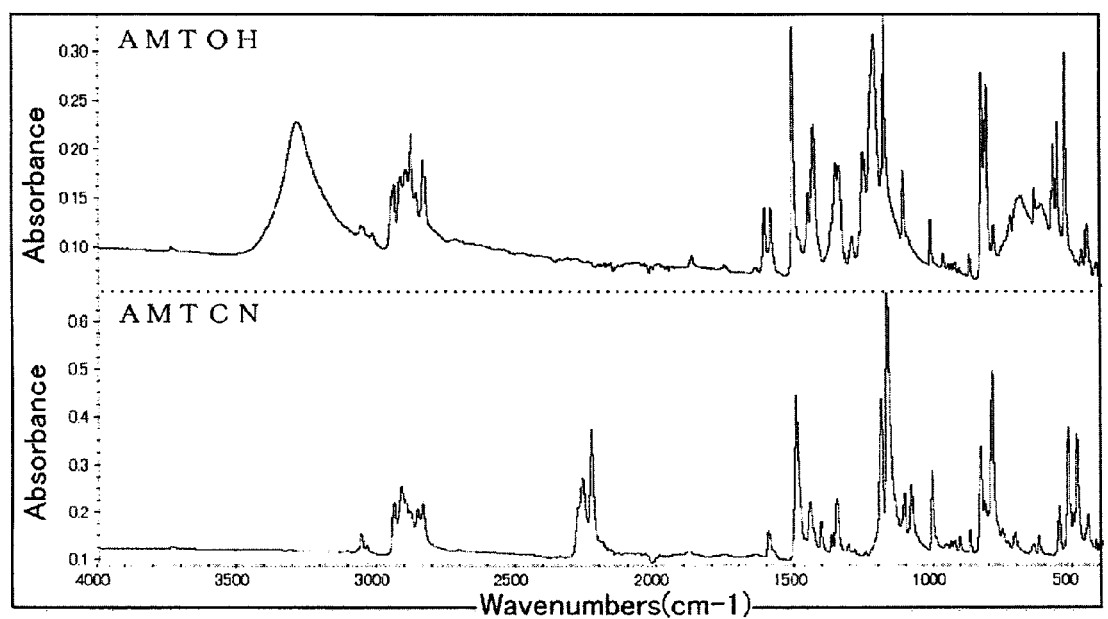
FIG. 7 shows an IR chart of the 1,3-bis(4-cyanatophenyl)-5,7-dimethyladamantane.

After completion of the water washing, the dichloromethane phase was concentrated under reduced pressure, and finally, it was concentrated and dried at 90° C. for 1 hour to obtain 436 g of the cyanate ester compound AMTCN (white crystal) of interest. The IR spectrum of the obtained cyanate ester compound AMTCN exhibited absorption of 2250 cm$^{-1}$ (cyanate ester group) and did not exhibit the absorption of hydroxy group. The IR chart is shown in FIG. 7.

(Sample 4)
<Preparation of Resin Composition and Production of Hardened Product>

100 parts by mass of the cyanate ester compound NEON obtained in Sample 1 was added into an eggplant-shaped flask, and it was then melted by heating at 150° C., followed by deaeration with a vacuum pump. Thereafter, the resultant was injected into a mold made of an aluminum plate, a copper foil and a fluorine-coated stainless steel, and the mold was then placed in an oven, so that the resin was homogenized at 150° C. Thereafter, the resulting resin was hardened by vacuum pressing at 220° C. for 90 minutes at a rate of 20 kg/cm$^2$, thereby producing a hardened product with a 100-mm square and a thickness of 1.5 mm.

(Sample 5)
A hardened product was obtained in the same manner as that of Sample 4, with the exceptions that 100 parts by mass of SNCN-MX was used instead of 100 parts by mass of NECN, and that 0.1 part by mass of zinc octylate (manufactured by Nihon Kagaku Sangyo Co., Ltd., trade mark: Nikka Octhix Zinc, metal content: 18%) was further added in Sample 4.

(Sample 6)
A hardened product was obtained in the same manner as that of Sample 4, with the exceptions that 100 parts by mass of SNCN-MX was used instead of 100 parts by mass of NECN, that 0.1 part by mass of zinc octylate (manufactured by Nihon Kagaku Sangyo Co., Ltd., trade mark: Nikka Octhix Zinc, metal content: 18%) was further added, and that the resin was heated at 220° C. for 6 hours after completion of the vacuum pressing at 220° C. for 90 minutes at 20 kg/cm$^2$ in Sample 4.

(Sample 7)
A hardened product was obtained in the same manner as that of Sample 5, with the exception that 100 parts by mass of AMTCN was used instead of 100 parts by mass of SNCN-MX in Sample 5.

(Sample 8)
A hardened product was obtained in the same manner as that of Sample 6, with the exception that 100 parts by mass of AMTCN was used instead of 100 parts by mass of SNCN-MX in Sample 6.

(Sample 9)
A hardened product was obtained in the same manner as that of Sample 4, with the exception that 100 parts by mass of 2,2-bis(4-cyanatophenyl)propane (manufactured by Mitsubishi Gas Chemical Company, Inc., trade name: skylex) was used instead of 100 parts by mass of NECN in Sample 4.

(Sample 10)
A hardened product was obtained in the same manner as that of Sample 4, with the exceptions that 100 parts by mass of 2,2-bis(4-cyanatophenyl)propane (manufactured by Mitsubishi Gas Chemical Company, Inc., trade name: skylex) was used instead of 100 parts by mass of NECN, and that the resin was heated at 220° C. for 6 hours after completion of the vacuum pressing at 220° C. for 90 minutes at 20 kg/cm$^2$ in Sample 4.

(Sample 11)
A hardened product was obtained in the same manner as that of Sample 4, with the exceptions that 100 parts by mass of 2,2-bis(4-cyanatophenyl)propane (manufactured by Mitsubishi Gas Chemical Company, Inc., trade name: skylex) was used instead of 100 parts by mass of NECN, and that 0.05 parts by mass of zinc octylate (manufactured by Nihon Kagaku Sangyo Co., Ltd., trade mark: Nikka Octhix Zinc, metal content: 18%) was further added in Sample 4.

(Sample 12)
A hardened product was obtained in the same manner as that of Sample 4, with the exceptions that 100 parts by mass of 2,2-bis(4-cyanatophenyl)propane (manufactured by Mitsubishi Gas Chemical Company, Inc., trade name: skylex) was used instead of 100 parts by mass of NECN, that 0.05 parts by mass of zinc octylate (manufactured by Nihon Kagaku Sangyo Co., Ltd., trade mark: Nikka Octhix Zinc, metal content: 18%) was further added, and that the resin was heated at 220° C. for 6 hours after completion of the vacuum pressing at 220° C. for 90 minutes at 20 kg/cm$^2$ in Sample 4.

<Evaluation of Hardened Products>
The properties of individual hardened products obtained as described above were evaluated by the following method.

Glass transition temperature (Tg): In accordance with JIS-K7244-3 (JIS C6481), a dynamic viscoelasticity was measured using a dynamic viscoelasticity measurement device (manufactured by TA Instruments Japan, Q800), at an initiation temperature of 30° C., at a termination temperature of 400° C., at a temperature increase rate of 10° C./min, and at a measurement frequency of 10 Hz. A maximum value of a loss elastic modulus (E") obtained upon the measurement was defined as a glass transition temperature.

Coefficiency of thermal expansion: In accordance with JIS-K-7197-2012 (JIS C6481), thermo-mechanical analysis was carried out in an expansion/compression mode, employing a thermo-mechanical analyzer (manufactured by SII NanoTechnology Inc., TMA/SS6100), using a test piece of 5 mm×5 mm×1.5 mm, at an initiation temperature of 30° C., at a termination temperature of 330° C., at a temperature increase rate of 10° C./min, and at a load of 0.05 N (49 mN). The average amount of thermal expansion per ° C. was measured in a range of 60° C. to 120° C.

A weight reduction percentage (%): In accordance with JIS-K7120-1987, a weight was measured employing a thermal gravimetric-differential thermal analyzer (manufactured by SII NanoTechnology Inc., TG/DTA6200), using a test piece of 3 mm×3 mm×1.5 mm, at an initiation temperature of 30° C., at a termination temperature of 550° C., at a temperature increase rate of 10° C./min, and in a nitrogen atmosphere. A weight reduction percentage at 500° C. was calculated according to the following formula:

$$\text{Weight reduction percentage (\%)} = (I-J)/I \times 100$$

In the above formula, I indicates the weight at the initiation temperature, and J indicates the weight at 500° C.

Herein, the term "flame retardance" is used in the present invention to mean that a large amount of residue is present upon thermal decomposition, namely, that the weight reduction percentage is low.

The evaluation results are shown in Table 7.

As is apparent from Table 7, it was confirmed that a hardened product of a resin composition comprising a cyanated product of the phenolic resin having a polynaphthylene ether structure of the present invention has a relatively low coefficient of thermal expansion, and that it has excellent flame retardance and heat resistance.

Hirayama Manufacturing Corp., PC-3) at 121° C. at a pressure of 2 atm for 3 and 4 hours. Thereafter, the test piece was immersed in a solder at 260° C. for 60 seconds. Thereafter, a change in the appearance was observed by visual inspection. (The number of blisters/the number of tests)

TABLE 7

| | | | Sample 4 | Sample 5 | Sample 6 | Sample 7 | Sample 8 | Sample 9 | Sample 10 | Sample 11 | Sample 12 |
|---|---|---|---|---|---|---|---|---|---|---|---|
| Composition | NECN | Part by mass | 100 | 0 | 0 | 0 | 0 | 0 | 0 | 0 | 0 |
| | SNCN-MX | | 0 | 100 | 100 | 0 | 0 | 0 | 0 | 0 | 0 |
| | AMTCN | | 0 | 0 | 0 | 100 | 100 | 0 | 0 | 0 | 0 |
| | 2,2-Bis(4-cyanatophenyl)propane | | 0 | 0 | 0 | 0 | 0 | 100 | 100 | 100 | 100 |
| | Zinc octylate | | 0 | 0.1 | 0.1 | 0.1 | 0.1 | 0 | 0 | 0.05 | 0.05 |
| Hardening conditions | Vacuum pressing | 220° C. 90 minutes | Yes | Yes | Yes | Yes | Yes | Yes | Yes | Yes | Yes |
| | Heating | 220° C. 6 hours | No | No | Yes | No | Yes | No | Yes | No | Yes |
| Physical properties of hardened products | Tg | ° C. | 374 | 280 | 283 | 323 | >400 | 196 | 307 | 298 | 311 |
| | Coefficiency of thermal expansion | ppm/° C. | 49 | 42 | 39 | 51 | 49 | 59 | 53 | 56 | 50 |
| | Weight reduction percentage | % | 23 | 25 | 25 | 10 | 13 | 41 | 41 | 40 | 41 |

(Sample 13)

50 parts by mass of the NECN obtained in Sample 1, 50 parts by mass of biphenyl aralkyl-based epoxy resin (NC-3000-FH, manufactured by Nippon Kayaku Co., Ltd.), 100 parts by mass of fusion silica (SC2050MB, manufactured by Admatechs), and 0.04 parts by mass of zinc octylate (manufactured by Nihon Kagaku Sangyo Co., Ltd.) were blended to obtain a varnish. This varnish was diluted with methyl ethyl ketone, and an E-glass woven fabric having a thickness of 0.1 mm was then impregnated and coated with this varnish. The resulting product was dried by heating at 150° C. for 5 minutes, to obtain a prepreg containing 50% by mass of resin.

The thus obtained eight prepreg pieces were laminated on one another, and electrolytic copper foils (JTC-LPZ, manufactured by JX Nippon Mining & Metals Corporation) each having a thickness of 12 jam were disposed on both sides of the obtained prepreg product. The obtained product was subjected to lamination molding at a pressure of 30 kg f/cm2, at a temperature of 220° C. for 120 minutes, to obtain a metal foil clad laminate in which the thickness of an insulating layer was 0.8 mm. Using the obtained metal foil clad laminate, a glass transition temperature (Tg), a water absorption rate, heat resistance upon moisture absorption, and flame retardance were evaluated. The results are shown in Table 8.

(Measurement Methods and Evaluation Methods)

1) Glass transition temperature (Tg): In accordance with JIS C6481, a glass transition temperature was measured by a DMA method using a dynamic viscoelasticity analyzer (manufactured by TA Instruments Japan).

2) Water absorption rate: In accordance with JIS C648, a sample with a size of 30 mm×30 mm was treated using a pressure cooker tester (manufactured by Hirayama Manufacturing Corp., PC-3) at 121° C. at a pressure of 2 atm for 1, 3, and 5 hours. Thereafter a water absorption rate was measured.

3) Heat resistance upon moisture absorption: A test piece prepared by removing the entire copper foil, other than a half of one surface of a sample of 50 mm×50 mm, by etching was treated using a pressure cooker tester (manufactured by 4) Flame retardance: The copper foil was completely removed from a sample of 13 mm×130 mm by etching, to obtain a test piece. Using this test piece, a flame retardance test was carried out according to a UL94 vertical test method (n=5).

(Sample 14)

A metal foil clad laminate with a thickness of 0.8 mm was obtained in the same manner as that of Sample 13, with the exceptions that 50 parts by mass of a bisphenol A-based cyanate ester compound (CA210, manufactured by Mitsubishi Gas Chemical Company, Inc.) was used instead of 50 parts by mass of NEON, and that 0.03 parts by mass of zinc octylate was used in Sample 13. The evaluation results of the obtained metal foil clad laminate are shown in Table 8.

(Sample 15)

A metal foil clad laminate with a thickness of 0.8 mm was obtained in the same manner as that of Sample 13, with the exceptions that 50 parts by mass of a phenol novolac-based cyanate ester compound (Primaset PT-30, manufactured by Lonza Japan) was used instead of 50 parts by mass of NEON, and that, during the impregnation and coating treatment, the product was dried by heating at 165° C. for 4 minutes in Sample 13. The evaluation results of the obtained metal foil clad laminate are shown in Table 8.

TABLE 8

| | | Sample 13 | Sample 14 | Sample 15 |
|---|---|---|---|---|
| Glass transition temperature (° C.) | | 265 | 262 | 294 |
| Water absorption rate (%) | After treatment for 1 hour | 0.17 | 0.21 | 0.28 |
| | After treatment for 3 hours | 0.28 | 0.35 | 0.44 |
| | After treatment for 5 hours | 0.33 | 0.38 | 0.52 |
| Heat resistance upon moisture absorption | After treatment for 3 hours | 0/4 | 2/4 | 1/4 |
| | After treatment for 4 hours | 0/4 | 1/4 | 1/4 |
| Fire retardance | | V-0 | V-1 | V-1 |

As is apparent from Table 8, it was confirmed that a prepreg, a printed wiring board and the like, which do not only have excellent flame retardance but are also excellent in terms of low water-absorbing property, heat resistance upon moisture absorption and heat resistance, can be realized with the use of the resin composition of the present invention.

The present application is based on a Japanese patent application filed with the Japan Patent Office on Oct. 26, 2012 (Japanese Patent Application No. 2012-236302), a Japanese patent application filed with the Japan Patent Office on Jan. 8, 2013 (Japanese Patent Application No. 2013-001002), a Japanese patent application filed with the Japan Patent Office on Mar. 4, 2013 (Japanese Patent Application No. 2013-041491), and a Japanese patent application filed with the Japan Patent Office on Mar. 22, 2013 (Japanese Patent Application No. 2013-059992); and the disclosure of which is hereby incorporated by reference.

INDUSTRIAL APPLICABILITY

As described above, the resin composition of the present invention can be widely and effectively used, for example, as an electrical insulating material, a semiconductor plastic package, a sealing material, an adhesive, a laminating material, a resist, a build-up laminating material, etc. for various intended uses such as electrical and electronic materials, machine tool materials, and aviation materials. In particular, the present resin composition can be particularly effectively used as a raw material for printed wiring boards that are applicable to high integration and/or densification of recent information terminal devices or communication devices. Moreover, the laminate and metal-clad laminate of the present invention, etc. do not only have high flame retardance, but they also have excellent performance in terms of low water-absorbing property, heat resistance upon moisture absorption and heat resistance. Accordingly, the industrial practicability of the present resin composition is extremely high.

The invention claimed is:

1. A method for producing a cyanogen halide, which comprises contacting a halogen molecule with an aqueous solution containing hydrogen cyanide and/or a metal cyanide, so that the hydrogen cyanide and/or the metal cyanide is allowed to react with the halogen molecule in a reaction solution to obtain the cyanogen halide, wherein
more than 1 mole of the hydrogen cyanide or the metal cyanide is present per 1 mole of the halogen molecule, and when an amount of the hydrogen cyanide or metal cyanide that is unreacted is defined as mole (A) and an amount of the cyanogen halide that is generated is defined as mole (B), the reaction is terminated in a state in which (A):(A)+(B) is between 0.00009:1 and 0.2:1, wherein a pH of the reaction solution is less than 7, and a reaction temperature is −10° C. to 5° C.

2. The method for producing the cyanogen halide according to claim 1, wherein the hydrogen cyanide has previously been obtained by a reaction of a metal cyanide with an acid.

3. The method for producing the cyanogen halide according to claim 1, wherein a total content of the hydrogen cyanide and/or the metal cyanide in the aqueous solution is 2% to 20% by mass based on 100% by mass of the aqueous solution.

4. The method for producing the cyanogen halide according to claim 1, further comprising an extraction extracting the obtained cyanogen halide with an organic solvent.

5. A method for producing a cyanate ester compound, which comprises cyanation allowing the cyanogen halide obtained by the method for producing the cyanogen halide according to claim 1 to react with a hydroxy-substituted aromatic compound in the presence of a basic compound in a reaction solution, to obtain a cyanate ester compound.

6. The method for producing the cyanate ester compound according to claim 5, wherein, in the cyanation, a solution containing the cyanogen halide and the hydroxy-substituted aromatic compound is contacted with a solution containing the basic compound.

7. The method for producing the cyanate ester compound according to claim 6, wherein the solution containing the cyanogen halide comprises an organic solvent.

8. The method for producing the cyanate ester compound according to claim 6, wherein the solution containing the cyanogen halide comprises a mixture of water and an organic solvent.

9. The method for producing the cyanate ester compound according to claim 6, wherein the solution containing the basic compound comprises an organic solvent.

10. The method for producing the cyanate ester compound according to claim 6, wherein the solution containing the basic compound comprises water.

11. The method for producing the cyanate ester compound according to claim 5, wherein, in the cyanation, a solution containing the cyanogen halide is contacted with a solution containing the basic compound and the hydroxy-substituted aromatic compound.

12. The method for producing the cyanate ester compound according to claim 5, wherein, in the cyanation, a pH of the reaction solution is less than 7.

13. The method for producing the cyanate ester compound according to claim 5, wherein, in the cyanation, 0.5 to 5 moles of the cyanogen halide is present per 1 mole of the hydroxy group of the hydroxy-substituted aromatic compound.

14. The method for producing the cyanate ester compound according to claim 5, wherein the hydroxy-substituted aromatic compound is at least one selected from the group consisting of a phenolic resin having a polynaphthylene ether structure, a compound represented by the following general formula (1), a naphthol aralkyl resin, and a phenolic resin having an adamantane structure:

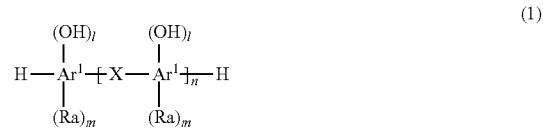

(1)

wherein $Ar^1$ each independently represent a phenylene group optionally having a substituent, a naphthylene group optionally having a substituent, or a biphenylene group optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; m represents the number of Ra bonded to Ar¹, wherein it is an integer of 4-1 when Ar¹ represents a phenylene group, it is an integer of 6-1 when Ar¹ represents a naphthylene group, and it is an integer of 8-1 when Ar¹ represents a biphenylene group; n represents an average number of repetitions, which is an integer of 0 to 50; and X each independently represent a single bond, a divalent organic group containing 1 to 50 carbon atoms wherein a hydrogen atom may be optionally replaced by a heteroatom, a divalent organic group containing 1 to 10 nitrogen atoms, a carbonyl group (—CO—), a carboxy group (—C(=O)O—), a carbonyl dioxide group (—OC(=O)O—), a sulfonyl group (—SO₂—), or a divalent sulfur atom or a divalent oxygen atom.

15. The method for producing the cyanate ester compound according to claim 14, wherein X in the above general formula (1) is a divalent linking group selected from the group consisting of a divalent organic group represented by the following general formula (2):

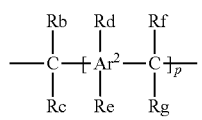

(2)

wherein Ar² each independently represent a phenylene group optionally having a substituent, a naphthylene group optionally having a substituent, or a biphenylene group optionally having a substituent; Rb, Rc, Rf, and Rg each independently represent a hydrogen atom, an alkyl group containing 1 to 6 carbon atoms and optionally having a substituent, or an aryl group containing 6 to 12 carbon atoms and optionally having a substituent; Rd and Re each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, or a hydroxy group; and p represents an integer of 0 to 5, and divalent groups represented by the following general formulae (2a), (2b), (2c), (2d), (2e), (2f), (2g), (2h), (2i), and (2j):

—O— (2a)

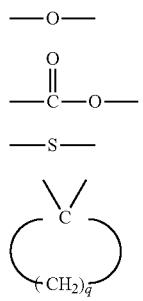

(2b)

(2c)

(2d)

(2e)

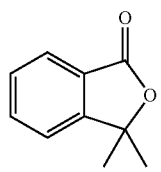

-continued

(2f)

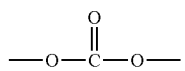

(2g)

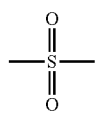

(2h)

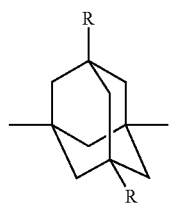

(2i)

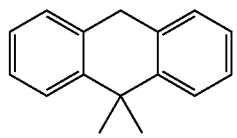

(2j)

wherein, in the formula (2d), q represents an integer of 4 to 7, and in the formula (2i), R each independently represents a hydrogen atom or an alkyl group containing 1 to 6 carbon atoms and optionally having a substituent.

16. The method for producing the cyanate ester compound according to claim 14, wherein the phenolic resin having a polynaphthylene ether structure is obtained by subjecting a polyhydric hydroxynaphthalene compound having two or more phenolic hydroxy groups in one molecule to a dehydration condensation reaction in the presence of a basic catalyst.

17. The method for producing the cyanate ester compound according to claim 14, wherein the phenolic resin having a polynaphthylene ether structure comprises a compound represented by the following general formula (3):

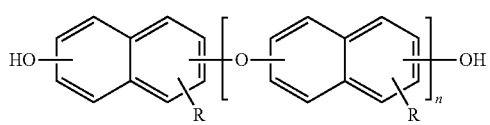

(3)

wherein R each independently represents a hydrogen atom, an aryl group and an alkyl group, or the following general formula (4); and n represents an integer of 1 to 20:

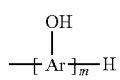

(4)

wherein Ar each independently represent an aryl group; and m represents an integer of 1 or 2.

18. The method for producing the cyanate ester compound according to claim 14, wherein the naphthol aralkyl resin comprises a resin represented by the following formula (19):

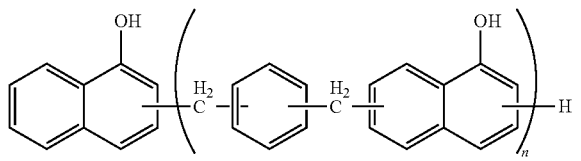

(19)

wherein n represents an integer of 1 to 50.

19. The method for producing the cyanate ester compound according to claim 14, wherein the phenolic resin having an adamantane structure comprises a resin represented by the following formula (20):

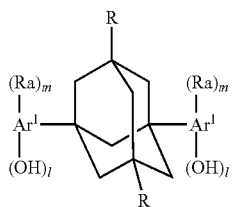

(20)

wherein $Ar^1$ each independently represent a phenylene group optionally having a substituent, a naphthylene group optionally having a substituent, or a biphenylene group optionally having a substituent; R each independently represent a hydrogen atom or an alkyl group containing 1 to 6 carbon atoms and optionally having a substituent; Ra each independently represent a hydrogen atom, an alkyl group containing 1 to 6 carbon atoms and optionally having a substituent, an aryl group containing 6 to 12 carbon atoms and optionally having a substituent, an alkoxy group containing 1 to 4 carbon atoms and optionally having a substituent, an aralkyl group optionally having a substituent, in which an alkyl group containing 1 to 6 carbon atoms is bonded to an aryl group containing 6 to 12 carbon atoms, or an alkylaryl group optionally having a substituent, in which an alkyl group containing 1 to 6 carbon atoms is bonded to an aryl group containing 6 to 12 carbon atoms; l represents the number of hydroxy groups bonded to $Ar^1$, which is an integer of 1 to 3; and m represents the number of Ra bonded to $Ar^1$, wherein it is an integer of 5-1 when $Ar^1$ represents a phenylene group, it is an integer of 7-1 when $Ar^1$ represents a naphthylene group, and it is an integer of 9-1 when $Ar^1$ represents a biphenylene group.

\* \* \* \* \*